US012227562B2

(12) United States Patent
Miller et al.

(10) Patent No.: US 12,227,562 B2
(45) Date of Patent: Feb. 18, 2025

(54) COMPOSITIONS AND METHODS TO TREAT VIRAL INFECTION AND CO-MORBIDITIES

(71) Applicants: The Regents of the University of California, Oakland, CA (US); The George Washington University, Washington D.C., DC (US); Baker Heart and Diabetes Research Institute, Melbourne (AU)

(72) Inventors: Yury Miller, San Diego, CA (US); Michael Bukrinsky, Washington D.C., DC (US); Dmitri Sviridov, Melbourne (AU)

(73) Assignees: The Regents of the University of California, Oakland, CA (US); The George Washington University, Washington D.C., DC (US); Baker Heart and Diabetes Research Institute., Melbourne (AU)

( * ) Notice: Subject to any disclaimer, the term of this patent is extended or adjusted under 35 U.S.C. 154(b) by 61 days.

(21) Appl. No.: 17/544,416

(22) Filed: Dec. 7, 2021

(65) Prior Publication Data

US 2022/0177559 A1    Jun. 9, 2022

Related U.S. Application Data

(60) Provisional application No. 63/122,203, filed on Dec. 7, 2020.

(51) Int. Cl.
| | |
|---|---|
| *C07K 16/18* | (2006.01) |
| *A61P 31/18* | (2006.01) |
| *B82Y 5/00* | (2011.01) |
| *A61K 39/00* | (2006.01) |

(52) U.S. Cl.
CPC ............. *C07K 16/18* (2013.01); *A61P 31/18* (2018.01); *A61K 2039/505* (2013.01); *B82Y 5/00* (2013.01)

(58) Field of Classification Search
None
See application file for complete search history.

(56) References Cited

U.S. PATENT DOCUMENTS

2016/0115211 A1* 4/2016 Miller ................. A61P 29/00
424/139.1

OTHER PUBLICATIONS

Dubrovsky, et al. mBio. Jan. 21, 2020;11(1):e02956-19. doi: 10.1128/mBio.02956-19. Erratum in: mBio. Mar. 17, 2020;11(2): PMID: 31964734; PMCID: PMC6974568.. (Year: 2020).*
Choi SH, et al. Intracellular AIBP (Apolipoprotein A-I Binding Protein) Regulates Oxidized LDL (Low-Density Lipoprotein)-Induced Mitophagy in Macrophages. Arterioscler Thromb Vasc Biol. Feb. 2021;41(2):e82-e96. doi: 10.1161/ATVBAHA. 120. 315485. Epub Dec. 24, 2020. PMID: 33356389. (Year: 2020).*
Song, Y., J. Liu, K. Zhao, L. Gao, and J. Zhao. 2021. Cholesterol-induced toxicity: An integrated view of the role of cholesterol in multiple diseases. Cell metabolism 33: 1911-1925.
Vona, R., E. Iessi, and P. Matarrese. 2021. Role of Cholesterol and Lipid Rafts in Cancer Signaling: A Promising Therapeutic Opportunity? Front Cell Dev Biol 9: 622908.
Sorice, M., R. Misasi, G. Riitano, V. Manganelli, S. Martellucci, A. Longo, T. Garofalo, and V. Mattei. 2020. Targeting Lipid Rafts as a Strategy Against Coronavirus. Frontiers in cell and developmental biology 8: 618296.
Ono, A. 2010. Relationships between plasma membrane microdomains and HIV-1 assembly. Biol Cell 102: 335-350.
Waheed, A. A., and E. O. Freed. 2009. Lipids and membrane microdomains in HIV-1 replication. Virus Res 143: 162-176.
Sviridov, D., N. Mukhamedova, and Y. I. Miller. 2020. Lipid rafts as a therapeutic target. J. Lipid Res. 61: 687-695.
Maselli, A., M. Pierdominici, C. Vitale, and E. Ortona. 2015. Membrane lipid rafts and estrogenic signalling: a functional role in the modulation of cell homeostasis. Apoptosis 20: 671-678.
Sebastiao, A. M., M. Colino-Oliveira, N. Assaife-Lopes, R. B. Dias, and J. A. Ribeiro. 2013. Lipid rafts, synaptic transmission and plasticity: impact in age-related neurodegenerative diseases. Neuropharmacology 64: 97-107.
Bukrinsky, M. I., N. Mukhamedova, and D. Sviridov. 2020. Lipid rafts and pathogens: the art of deception and exploitation. J. Lipid Res. 61: 601-610.
Kocar, E., T. Rezen, and D. Rozman. 2021. Cholesterol, lipoproteins, and COVID-19: Basic concepts and clinical applications. Biochim Biophys Acta Mol Cell Biol Lipids 1866: 158849.
Sviridov, D., N. Mukhamedova, A. A. Makarov, A. Adzhubei, and M. Bukrinsky. 2020. Comorbidities of HIV infection: role of Nef-induced impairment of cholesterol metabolism and lipid raft functionality. AIDS 34: 1-13.
Wu, Y., Y. Liu, E. Gulbins, and H. Grassme. 2021. The Anti-Infectious Role of Sphingosine in Microbial Diseases. Cells 110.
Fang, L., and Y. I. Miller. 2019. Regulation of lipid rafts, angiogenesis and inflammation by AIBP. Curr. Opin. Lipidol. 30: 218-223.
Vahedian-Azimi, A., S. M. Mohammadi, F. Heidari Beni, M. Banach, P. C. Guest, T. Jamialahmadi, and A. Sahebkar. 2021. Improved COVID-19 ICU admission and mortality outcomes following treatment with statins: a systematic review and meta-analysis. Arch Med Sci 17: 579-595.

(Continued)

*Primary Examiner* — Benjamin P Blumel
*Assistant Examiner* — Jeffrey Mark Sifford
(74) *Attorney, Agent, or Firm* — Gregory P. Einhorn; Greer, Burns & Crain, Ltd.

(57) ABSTRACT

In alternative embodiments, provided are compositions, including products of manufacture and kits, and methods, for preventing or slowing the spread of a viral infection, wherein optionally the viral infection is a coronavirus infection, optionally a COVID-19 infection or variant thereof, or a human immunodeficiency virus (HIV) infection, preventing or decreasing coronavirus or HIV-co-morbidities in an individual, or inhibiting, or slowing the rate of, coronavirus (optionally COVID-19) or HIV replication in vitro and in vivo.

16 Claims, 35 Drawing Sheets
(33 of 35 Drawing Sheet(s) Filed in Color)

Specification includes a Sequence Listing.

(56) References Cited

OTHER PUBLICATIONS

Durstenfeld, M. S., and P. Y. Hsue. 2021. Mechanisms and primary prevention of atherosclerotic cardiovascular disease among people living with HIV. Curr Opin HIV AIDS 16: 177-185.
Vartak, R., M. Patki, S. Menon, J. Jablonski, S. Mediouni, Y. Fu, S. T. Valente, B. Billack, and K. Patel. 2020. beta-cyclodextrin polymer/Soluplus(R) encapsulated Ebselen ternary complex (EbetapolySol) as a potential therapy for vaginal candidiasis and pre-exposure prophylactic for HIV. Int J Pharm 589: 119863.
Jicsinszky, L., K. Martina, and G. Cravotto. 2021. Cyclodextrins in the antiviral therapy. J Drug Deliv Sci Technol 64: 102589.
Woller, S. A., S. H. Choi, E. J. An, H. Low, D. A. Schneider, R. Ramachandran, J. Kim, Y. S. Bae, D. Sviridov, M. Corr, T. L. Yaksh, and Y. I. Miller. 2018. Inhibition of Neuroinflammation by AIBP: Spinal Effects upon Facilitated Pain States. Cell Rep 23: 2667-2677.
Schneider, D. A., S. H. Choi, C. Agatisa-Boyle, L. Zhu, J. Kim, J. Pattison, D. D. Sears, P. Gordts, L. Fang, and Y. I. Miller. 2018. AIBP protects against metabolic abnormalities and atherosclerosis. J Lipid Res 59: 854-863.
Fang, L., S. H. Choi, J. S. Baek, C. Liu, F. Almazan, F. Ulrich, P. Wiesner, A. Taleb, E. Deer, J. Pattison, J. Torres-Vazquez, A. C. Li, and Y. I. Miller. 2013. Control of angiogenesis by AIBP-mediated cholesterol efflux. Nature 498: 118-122.
Choi, S. H., A. M. Wallace, D. A. Schneider, E. Burg, J. Kim, E. Alekseeva, N. D. Ubags, C. D. Cool, L. Fang, B. T. Suratt, and Y. I. Miller. 2018. AIBP augments cholesterol efflux from alveolar macrophages to surfactant and reduces acute lung inflammation. JCI Insight 3: e120519.
Manes, S., G. del Real, and A. C. Martinez. 2003. Pathogens: raft hijackers. Nat Rev Immunol 3: 557-568.
Schneider, D. A., S.-H. Choi, C. Agatisa-Boyle, L. Zhu, J. Kim, J. Pattison, D. D. Sears, P. L. S. M. Gordts, L. Fang, and Y. I. Miller. 2018. AIBP protects against metabolic abnormalities and atherosclerosis. J. Lipid Res. 59: 854-863.
Nalbandian, A., K. Sehgal, A. Gupta, M. V. Madhavan, C. McGroder, J. S. Stevens, J. R. Cook, A. S. Nordvig, D. Shalev, T. S. Sehrawat, N. Ahluwalia, B. Bikdeli, D. Dietz, C. Der-Nigoghossian, N. Liyanage-Don, G. F. Rosner, E. J. Bernstein, S. Mohan, A. A. Beckley, D. S. Seres, T. K. Choueiri, N. Uriel, J. C. Ausiello, D. Accili, D. E. Freedberg, M. Baldwin, A. Schwartz, D. Brodie, C. K. Garcia, M. S. V. Elkind, J. M. Connors, J. P. Bilezikian, D. W. Landry, and E. Y. Wan. 2021. Post-acute COVID-19 syndrome. Nature Medicine 27: 601-615.

\* cited by examiner

Days post infection

COMPOSITIONS AND METHODS TO TREAT VIRAL INFECTION AND CO-MORBIDITIES

RELATED APPLICATIONS

This U.S. Utility Patent Application claims the benefit of priority under 35 U.S.C. § 119(e) of U.S. Provisional Application Ser. No. 63/122,203 filed Dec. 7, 2020. The aforementioned application is expressly incorporated herein by reference in its entirety and for all purposes.

STATEMENT AS TO FEDERALLY SPONSORED RESEARCH

This invention was made with government support under HL135737, HL131473, P30 AI117970, P30 AI055019, NS102432, HL136275, NS104769, awarded by the National Institutes of Health. The government has certain rights in the invention.

TECHNICAL FIELD

This invention generally relates to coronavirus and human immunodeficiency biology and biological therapeutics. In alternative embodiments, provided are compositions, including products of manufacture and kits, and methods, for inhibiting, or slowing the rate of, a viral infection, wherein optionally the viral infection is a coronavirus infection, optionally a COVID-19 infection, or a human immunodeficiency virus (HIV) infection, in vitro and in vitro.

BACKGROUND

Apolipoprotein A-I binding protein (AIBP) is a secreted protein involved in regulation of lipid rafts and cholesterol efflux. AIBP has been suggested to function as a protective factor in several pathological conditions associated with increased abundance of lipid rafts, such as atherosclerosis and acute lung injury.

HIV infection and HIV components modify host and bystander cell plasma membrane (specifically, lipid rafts) in a way that promotes new HIV-cell membrane fusion, propagation of infection and promotes HIV-associated co-morbidities.

COVID-19 is the biggest global pandemic of the $21^{st}$ century and it may not be the last. Increased interactions of humans with animals amplifies chances of animal viruses "jumping" to humans, while increased density of human population and abundant international travel further contribute to the extremely fast spread of the infectious diseases around the globe. At the peak of a pandemic, public health measures provide the most effective protection against spread of the infection, but when the peak passes, it leaves behind important problems. First, it is now clear that the virus will continue to circulate in the population and mutate causing periodic outbreaks. Second, initial infection often causes an outbreak of various chronic diseases ensuing from the presence of a "suppressed" virus or as a long-term consequence of the initial exposure. Global immunization reduces the severity of the disease and frequency of outbrakes, but, as a rule, does not achieve full eradication of an infectious disease. Many viruses are resistant to vaccination through rapid mutagenesis, like influenza viruses (Altman et al., 2018), employing cell-to-cell transmission altogether bypassing exposure to antibodies, like HTLV (Omsland et al., 2018), gaining entry through the respiratory tract delaying the access of antibodies and T-cells to the site of infection, like coronaviruses (He et al., 2020), or a combination of these and yet unknown factors, such as with HIV and influenza. A solution is to develop an anti-viral medication. Ideally, such treatment should target an early stage of the viral lifecycle, be insensitive to frequent changes of viral phenotype due to mutagenesis (for example targeting host cell rather than the virus) and be safe. Preferably, this treatment should also target complications of the infection.

SUMMARY

In alternative embodiments, provided are products of manufacture for inhibiting, or slowing the rate of, coronavirus (optionally COVID-19 or a variant thereof, such as for example a delta or omicron COVID variant strain) or HIV replication in vitro and in vitro.

In alternative embodiments, provided are methods for:
preventing or slowing the spread of a viral infection, wherein optionally the viral infection is a coronavirus infection, optionally a COVID-19 or variant thereof (such as for example a delta or omicron COVID variant strain) infection, or a human immunodeficiency virus (HIV) infection,
preventing or decreasing coronavirus (optionally COVID-19 or variant thereof) or HIV-co-morbidities in an individual,
preventing or decreasing sequelae diseases, conditions or symptoms of coronavirus (optionally COVID-19 or variant thereof) or HIV, or preventing or decreasing the severity of long COVID syndrome, or
inhibiting, or slowing the rate of, coronavirus (optionally COVID-19 or variant thereof) or HIV replication in vitro and in vitro,
the method comprising:
(a)
(i) providing or having provided a protein or a composition having Apolipoprotein A-I binding protein (AIBP) activity, and
(ii) administering to an individual in need thereof the protein or the composition having Apolipoprotein A-I binding protein (AIBP) activity; or
(b) administering to an individual in need thereof a protein or a composition having Apolipoprotein A-I binding protein (AIBP) activity.

In alternative embodiments, provided are a protein or a composition having Apolipoprotein A-I binding protein (AIBP) activity for use in:
preventing or slowing the spread of a viral infection, wherein optionally the viral infection is a coronavirus infection, optionally a COVID-19 or variant, such as for example a delta or omicron COVID variant strain, infection, or a human immunodeficiency virus (HIV) infection,
preventing or decreasing coronavirus (optionally COVID-19) or HIV-co-morbidities in an individual, or
inhibiting, or slowing the rate of, coronavirus (optionally COVID-19) or HIV replication in vitro and in vitro.

In alternative embodiments, provided are uses of a protein or a composition having Apolipoprotein A-I binding protein (AIBP) activity in the manufacture of a medicament for:
preventing or slowing the spread of viral infection, optionally a coronavirus (optionally COVID-19, or variant thereof, such as for example a delta or omicron COVID variant strain) or human immunodeficiency virus (HIV) infection,
preventing or decreasing coronavirus (optionally COVID-19) or HIV-co-morbidities in an individual, or inhibiting, or slowing the rate of, coronavirus (optionally COVID-19) or HIV replication in vitro and in vitro.

In alternative embodiments, of the methods or uses as provided herein:

the individual in need is coronavirus (optionally COVID-19 or variant thereof, such as for example a delta or omicron COVID variant strain) or an HIV infected human;

the protein or the composition having Apolipoprotein A-I binding protein (AIBP) activity is an antibody or a small molecule, optionally a recombinant anti-Apolipoprotein A-I binding protein (AIBP) protein antibody or fragment thereof;

the protein or the composition having Apolipoprotein A-I binding protein (AIBP) activity is a recombinant Apolipoprotein A-I binding protein (AIBP) protein;

the protein or the composition having Apolipoprotein A-I binding protein (AIBP) activity is formulated:
(a) for administration in vitro or in vivo;
(b) for enteral or parenteral administration;
(c) as a liposome, a nanoparticle, or a nanoliposome;
(d) as a tablet, a pill, a capsule, a gel, a hydrogel, a geltab, a liquid, a powder, an emulsion, a lotion, an aerosol, a spray, a lozenge, an aqueous or a sterile or an injectable solution, an eye drop, or an implant; or
(e) for intravenous injection, subcutaneous injection, intramuscular injection, inhalation, or intravitreal injection; or the protein or the composition having Apolipoprotein A-I binding protein (AIBP) activity is formulated as or in a nanoparticle, a nanolipoparticle, a vesicle or a liposomal membrane.

In alternative embodiments, of the methods or uses as provided herein, the protein or the composition having Apolipoprotein A-I binding protein (AIBP) activity comprises a human AIBP protein, an active fragment thereof, or a nucleic acid acid encoding AIBP, or an active fragment thereof, for example, in alternative embodiments the protein or the composition having Apolipoprotein A-I binding protein (AIBP) activity comprises:

(SEQ ID NO: 10)
GGGCCGGGCCGGGCCGGGGCGCGCGCTCTGCGAGCTGGATGTCCAGGCT

GCGGGCGCTGCTGGGCCTCGGGCTGCTGGTTGCGGGCTCGCGCGTGCCGC

GGATCAAAAGCCAGACCATCGCCTGTCGCTCGGGACCCACCTGGTGGGA

CCGCAGCGGCTGAACTCGGGTGGCCGCTGGGACTCAGAGGTCATGGCGAG

CACGGTGGTGAAGTACCTGAGCCAGGAGGAGGCCCAGGCCGTGGACCAGG

AGCTATTTAACGAATACCAGTTCAGCGTGGACCAACTTATGGAACTGGCC

GGGCTGAGCTGTGCTACAGCCATCGCCAAGGCATATCCCCCCACGTCCAT

GTCCAGGAGCCCCCCTACTGTCCTGGTCATCTGTGGCCCGGGGAATAATG

GAGGAGATGGTCTGGTCTGTGCTCGACACCTCAAACTCTTTGGCTACGAG

CCAACCATCTATTACCCCAAAAGGCCTAACAAGCCCCTCTTCACTGCATT

GGTGACCCAGTGTCAGAAAATGGACATCCCTTTCCTTGGGGAAATGCCCG

CAGAGCCCATGACGATTGATGAACTGTATGAGCTGGTGGTGGATGCCATC

TTTGGCTTCAGCTTCAAGGGCGATGTTCGGGAACCGTTCCACAGCATCCT

GAGTGTCCTGAAGGGACTCACTGTGCCCATTGCCAGCATCGACATTCCCT

CAGGATGGGACGTGGAGAAGGGAAATGCTGGAGGGATCCAGCCAGACTTG

CTCATATCCCTCACAGCCCCCAAAAAATCTGCAACCCAGTTTACCGGTCG

CTACCATTACCTGGGGGGTCGTTTTGTGCCACCTGCTCTGGAGAAGAAGT

ACCAGCTGAACCTGCCACCCTACCCTGACACCGAGTGTGTCTATCGTCTG

CAGTGAGGGAAGGTGGGTGGGTATTCTTCCCAATAAAGACTTAGAGCCCC

TCTCTTCCAGAACTGTGGATTCCTGGGAGCTCCTCTGGCAATAAAAGTCA

GTGAATGGTGGAAGTCAGAGACCAACCCTGGGGATTGGGTGCCATCTCTC

TAGGGGTAACACAAAGGGCAAGAGGTTGCTATGGTATTTGGAAACAATGA

AAATGGACTGTTAGATGCCAA (SEQ ID NO: 11)
MSRLRALLGLGLLVAGSRVPRIKSQTIACRSGPTWWGPQRLNSGGRWDSE

VMASTVVKYLSQEEAQAVDQELFNEYQFSVDQLMELAGLSCATAIAKAYP

PTSMSRSPPTVLVICGPGNNGGDGLVCARHLKLFGYEPTIYYPKRPNKPL

FTALVTQCQKMDIPFLGEMPAEPMTIDELYELVVDAIFGFSFKGDVREPF

HSILSVLKGLTVPIASIDIPSGWDVEKGNAGGIQPDLLISLTAPKKSATQ

FTGRYHYLGGRFVPPALEKKYQLNLPPYPDTECVYRLQ

The details of one or more exemplary embodiments of the invention are set forth in the accompanying drawings and description below. Other features, objects, and advantages of the invention will be apparent from the figures (drawings), description, and from the claims.

All publications, patents, patent applications cited herein are hereby expressly incorporated by reference for all purposes.

DESCRIPTION OF DRAWINGS

The patent or application file contains at least one drawing executed in color. Copies of this patent or patent application publication with color drawing(s) will be provided by the Office upon request and payment of the necessary fee.

The drawings set forth herein are illustrative of exemplary embodiments provided herein and are not meant to limit the scope of the invention as encompassed by the claims.

FIG. 1A graphically illustrates data from quadruplicate wells of monocyte-derived macrophages (MDM) infected with HIV-1$_{ADA}$, and virus production was measured on day 12 post infection by RT activity in culture supernatant; bars show mean±standard deviation (SD);

FIG. 1B graphically illustrates data showing PHA-activated PBLs or MDM from one infected representative donor in triplicate wells, infected with HIV-1$_{LAI}$ or HIV-1$_{ADA}$ strains, respectively, cultured in the presence or absence of recombinant AIBP (0.2 µg/ml), and HIV replication was followed by measuring p24 in culture supernatants;

FIG. 2A graphically illustrates flow cytometry data showing PBLs from a representative donor stimulated, or not, with PHA, stained with fluorescently labeled cholera toxin B subunit, and analyzed by flow cytometry;

FIG. 2B graphically illustrates data showing representative analysis of vesicle size and concentration in exosome samples from supernatants of HEK293 T cells transfected with Nef (exNef) or empty vector (exCont) by NANO-SIGHT™ (top panels);

FIG. 2C graphically illustrates data showing vesicles analyzed by Western blotting for the exosomal marker Alix, tetraspanin CD63, cytosolic marker HSP70, and Nef;

FIG. 2D graphically illustrates data showing MDM from a representative donor treated with exNef or exCont in the presence of AIBP or BSA, and lipid rafts were analyzed as in FIG. 2A; and FIG. 2E graphically illustrates data showing lipid rafts were analyzed as in FIG. 2A and FIG. 2D, results are presented for experiments with cells from 4 different donors, as further discussed in Example 1, below.

FIG. 3A graphically illustrates data showing PBLs activated with PHA for 48 h, treated with 0.2 µg/ml recombinant AIBP (or BSA as control) for another 48 h, and exposed to BlaM-Vpr carrying HIV-1$_{NL4-3}$ in the presence or absence of recombinant AIBP, percentage of fused cells (cleaved CCF-2) was determined by flow cytometry;

FIG. 3B graphically illustrates data showing results of fusion analysis of PBLs from 4 donors as presented relative to fusion of activated PBL treated with BSA, taken as 100%;

FIG. 3C graphically illustrates data showing MDM exposed to control (exCont) or Nef exosomes (exNef) for 48 h in the presence of 0.2 µg/ml recombinant AIBP (or BSA as control), and then infected with BlaM-Vpr carrying HIV-1$_{NL(AD8)}$ in the presence or absence of recombinant AIBP, the percentage of fused cells was determined as in FIG. 3A;

FIG. 3D graphically illustrates data showing the results of fusion analysis of MDMs from 3 donors (mean±SD) are presented relative to fusion of exCont exposed cells treated with BSA, taken as 100%;

FIG. 3E illustrates an image of a Western blot for Nef (green) and p55 (red) of HEK293T cells transfected with vectors expressing Nef-positive and Nef-negative HIV-1;

FIG. 3F graphically illustrates data showing MDM exposed to exCont or exNef as in C and infected with BlaM-Vpr carrying Nef-positive or Nef-deficient HIV-1, fusion was analyzed as in FIG. 3A; and FIG. 3G graphically illustrates data from the experiment described in F, as performed with MDM from 6 donors, results are presented for each donor relative to fusion of exCont-treated MDM with HIVΔNef, as further discussed in Example 1, below.

FIG. 4A schematically illustrates a timeline of the exemplary in vivo experiment described in this figure;

FIG. 4B illustrates an image of a Western blot analysis of livers from hu-mice infected with AAV and AAV-AIBP;

FIG. 4C graphically illustrates data showing viral load analysis of hu-mice by a 2-way ANOVA;

FIG. 4D graphically illustrates data showing an analysis of human CD4+ cells in hu-mice;

FIG. 4E illustrates an image of a Western blot for AIBP and GAPDH of livers from hu-mice infected with HIV-1 and AAV-AIBP (#1, 2, 3), and hu-mice infected with HIV-1 and empty AAV (#7, 8, 9);

FIG. 4C graphically illustrates data showing quantitation of the blot in FIG. 4E.

FIG. 5A graphically illustrates data showing PHA-activated PBMCs from donors with HLA-B*35, HLA-B*57, and non-B*35, B*57 genotypes infected with HIV-1$_{LAI}$ and incubated in the presence or absence of recombinant AIBP, virus replication was followed by RT activity, and results are presented for donors B*35/55 (B*35), B*51/57 (B*57), and B*27/38 (non-B*35, B*57);

FIG. 5B graphically illustrates data from experiments performed as in FIG. 5A with cells from 3 donors of each genotype;

FIG. 5B graphically illustrates data showing results (mean±SD) presented relative to cells from non-B*35,57 donor (taken as 100%) at the time point corresponding to the peak of infection (day 5 p.i.);

FIG. 5C graphically illustrates data PHA-activated PBMCs from HLA-B*35 or non-B*35 donors infected with T/F strain pCH185.c/K3016 and cultured in the presence or absence of 0.2 µg/ml recombinant AIBP or BSA, virus replication was followed by RT activity;

FIG. 5D illustrates images of Western blots showing PHA-activated PBMCs from HLA-B*35 and non-B*35 donors treated with AIBP-targeting (siRNA$^{AIBP}$) or control (siRNA$^{Cont}$) Accell siRNA, and AIBP abundance was measured by PROTEINSIMPLE™ Western blotting (left panel), normalized against total protein, and presented relative to non-B*35 cells treated with siRNA$^{Cont}$ (right top panel), and cells were infected with HIV-1 LAI, and RT activity in culture supernatant was measured on day 4 post infection (right bottom panel);

FIG. 5E graphically illustrates data showing binding of recombinant AIBP to cells with different HLA-B genotype was analyzed by flow cytometry using anti-His antibody (top panel), Bottom panel shows quantitation of AIBP binding to cells from 4 different donors each of genotypes B*35 and non-B*35, B*57 and 3 donors of B*57 genotype;

FIG. 5F illustrates fluorescent microscopy images showing binding of recombinant AIBP to cells with HLA-B*35 and HLA-B*57 genotype, analyzed using ALEXA FLUOR555® conjugated CTB for lipid rafts (red), FITC-conjugated anti-His antibody for AIBP (green), and DAPI for nuclei (blue);

FIG. 5G graphically illustrates data showing quantification of MFI on 108 cells with HLA-B*35 and 159, with HLA-B*57 genotype using VOLOCITY™ software, as further discussed in Example 1, below.

FIG. 6A illustrates a flow cytometry data graph defining sizing gates with MEGAMIX™ beads; and FIG. 6B illustrates a flow cytometry EV visualization, where exCont and exNef EVs were labeled with the lipophilic tracer BODIPY (Invitrogen, Life Technologies, CA) and visualized with a LSRII (Becton Dickinson) as BODIPY-positive events thresholding on BODIPY (or 5,5-Difluoro-5H-4λ5-dipyrrolo[1,2-c:2',1'-f][1,3,2]diazaborinin-4-ylium-5-uide) fluorescence, Left column: Gating strategy for flow analysis of BODIPY-labeled EVs isolated from mock- (upper panel) or Nef-transfected (lower panel) HEK293T cells, and a singlet gate was defined by plotting fluorescence height versus fluorescence width, and the gate excludes events with a high width and high height that represent aggregates: right column illustrates EV sizing as defined by MEGAMIX™ plus SSC beads gates (as in FIG. 6A), as further discussed in Example 1, below.

FIG. 8A illustrates flow cytometry data showing gating for unactivated PBL;

FIG. 8B illustrates flow cytometry data showing gating for activated PBL; and

FIG. 8C illustrates flow cytometry data showing gating for MDM, as further discussed in Example 1, below.

FIG. 9A illustrates flow cytometry data showing gating for PBL;

FIG. 9B illustrates flow cytometry data showing gating for MDM; and

FIG. 9C illustrates flow cytometry data showing gating for MDM, as further discussed in Example 1, below.

FIG. 10A illustrates flow cytometry data where MDM were treated with control exosomes for 48 h in the presence of 0.2 µg/ml recombinant AFP or AIBP (both proteins expressed from baculovirus vector) and then infected with BlaM-Vpr carrying HIV-1 NL(AD8) in the presence of AFP, AIBP, or 1 µg/ml T-20. Percentage of fused cells (cleaved CCF-2) was determined by flow cytometry;

FIG. 10B illustrates flow cytometry gating strategy; and

FIG. 10C graphically illustrates data from the fusion analysis, which was performed as described in FIG. 10A, with MDMs from 3 donors, as further discussed in Example 1, below.

DETAILED DESCRIPTION

Figure 1A:
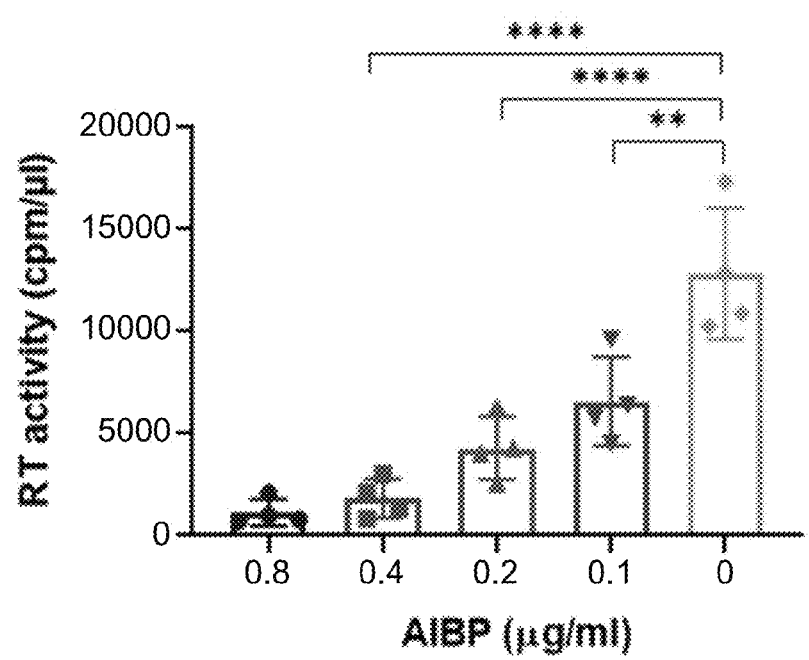
FIG. 1A-B illustrate data showing that AIBP inhibits HIV-1 replication.

In alternative embodiments, provided are compositions, including products of manufacture and kits, and methods, for inhibiting, or slowing the rate of, coronavirus (optionally COVID-19 or variant thereof, such as for example a delta or omicron COVID variant strain) or HIV replication in vitro and in vitro.

In alternative embodiments, provided are compositions and methods using AIBP to potently inhibit coronavirus (optionally COVID-19 or variant thereof, such as for example a delta or omicron COVID variant strain) or HIV replication in vitro and in vitro.

It was demonstrated that AIBP can potently inhibit HIV replication in vitro in HIV-infected humanized mice. AIBP inhibited virus-cell fusion, and this effect depended on lipid raft activation by Nef. Cells from donors with the HLA-B*35 genotype, associated with rapid progression of HIV disease, bound less AIBP than the cells from slow progressing HLA-B*57 donors, and were not protected by AIBP from rapid HIV replication. These results demonstrate that AIBP is an anti-HIV factor that can be used a potential anti-HIV biologic agent.

We have discovered that AIBP selectively targets cells affected by a coronavirus or an HIV or HIV-associated proteins and reverses pathological changes, thereby preventing spread of a coronavirus, or an HIV infection, and coronavirus- and/or HIV-comorbidities.

As described in Example 1, below, we investigated whether the dependence of HIV on lipid rafts and the ability of AIBP to reduce the abundance of lipid rafts translates into inhibition of HIV replication. We found that AIBP inhibits HIV replication both in vitro and in vivo and reverses the pro-infectious effects of Nef-containing extracellular vesicles. New therapeutic approaches aimed at inhibition of HIV infection and HIV-associated co-morbidities via stimulation of AIBP production are provided herein.

Formulations and Pharmaceutical Compositions

In alternative embodiments, provided are pharmaceutical formulations or compositions comprising a protein or a composition having Apolipoprotein A-I binding protein (AIBP) activity. In alternative embodiments, provided are pharmaceutical formulations or compositions for use in in vivo, in vitro or ex vivo methods to treat, prevent, reverse and/or ameliorate coronavirus (optionally COVID-19 or variant thereof, such as for example a delta or omicron COVID variant strain) or HIV.

In alternative embodiments, the pharmaceutical compositions used to practice methods as provided herein can be administered parenterally, topically, orally or by local administration, such as by aerosol or transdermally. These pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, for example, the latest edition of Remington's Pharmaceutical Sciences, Maack Publishing Co., Easton PA ("Remington's"). For example, in alternative embodiments, compositions used to practice methods as provided herein (comprising, for example, AIBP polypeptides) are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers used to practice methods as provided herein can be in forms such as tablets, pills, powders, capsules, liquids, gels, syrups, slurries, suspensions, etc., suitable for in vivo, in vitro or ex vivo applications.

In alternative embodiment, compounds (for example, formulations) used to practice methods as provided herein can comprise a solution of compositions (which include peptidomimetics, racemic mixtures or racemates, isomers, stereoisomers, derivatives and/or analogs of compounds AIBP) disposed in or dissolved in a pharmaceutically acceptable carrier, for example, acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice methods as provided herein are sterile and can be manufactured to be generally free of undesirable matter. In one embodiment, these solutions and formulations are sterilized by conventional, well known sterilization techniques.

The solutions and formulations used to practice methods as provided herein can comprise auxiliary substances as required to approximate physiological conditions such as pH adjusting and buffering agents, toxicity adjusting agents, for example, sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations used to practice methods as provided herein can be delivered by the use of liposomes. By using liposomes, particularly where the liposome surface carries ligands specific for target cells (for example, an injured or diseased neuronal cell or CNS tissue), or are otherwise preferentially directed to a specific tissue or organ type, one can focus the delivery of the active agent into a target cells in an in vivo, in vitro or ex vivo application.

Nanoparticles, Nanolipoparticles and Liposomes

Also provided are nanoparticles, nanolipoparticles, vesicles and liposomal membranes comprising compounds used to practice methods as provided herein.

Provided are multilayered liposomes comprising compounds used to practice methods as provided herein n, for example, as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice methods as provided herein.

Liposomes can be made using any method, for example, as described in Park, et al., U.S. Pat. Pub. No. 20070042031, including method of producing a liposome by encapsulating an active agent (for example, APOA1BP nucleic acids and polypeptides), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice methods as provided herein comprise a substituted ammonium and/or polyanions, for example, for targeting delivery of a compound (for example, a AIBP), as described for example, in U.S. Pat. Pub. No. 20070110798.

In alternative embodiments, also provided are nanoparticles comprising compounds (for example, AIBP polypeptides) used to practice methods as provided herein in the form of active agent-containing nanoparticles (for example, a secondary nanoparticle), as described, for example, in U.S. Pat. Pub. No. 20070077286. In one embodiment, provided are nanoparticles comprising a fat-soluble active agent of this invention or a fat-solubilized water-soluble active agent to act with a bivalent or trivalent metal salt.

In one embodiment, solid lipid suspensions can be used to formulate and to deliver compositions used to practice methods as provided herein to mammalian cells in vivo, in vitro or ex vivo, as described, for example, in U.S. Pat. Pub. No. 20050136121.

Delivery Vehicles

In alternative embodiments, any delivery vehicle can be used to practice the methods as provided herein, for example, to deliver compositions used to practice methods as provided herein (for example, AIBP polypeptides) to mammalian cells in vivo, in vitro or ex vivo. For example, delivery vehicles comprising polycations, cationic polymers and/or cationic peptides, such as polyethyleneimine derivatives, can be used for example as described, for example, in U.S. Pat. Pub. No. 20060083737.

In one embodiment, a dried polypeptide-surfactant complex is used to formulate a composition used to practice methods as provided herein, for example as described, for example, in U.S. Pat. Pub. No. 20040151766.

In one embodiment, a composition used to practice methods as provided herein can be applied to cells using vehicles with cell membrane-permeant peptide conjugates, for example, as described in U.S. Pat. Nos. 7,306,783; 6,589, 503. In one aspect, the composition to be delivered is conjugated to a cell membrane-permeant peptide. In one embodiment, the composition to be delivered and/or the delivery vehicle are conjugated to a transport-mediating peptide, for example, as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, for example, using any electroporation system as described for example in U.S. Pat. Nos. 7,109,034; 6,261,815; 5,874,268.

Dosaging

The pharmaceutical compositions and formulations used to practice methods as provided herein can be administered for prophylactic and/or therapeutic treatments. In alternative embodiments, therapeutic applications, compositions are administered to a subject already suffering from a coronavirus infection (for example, COVID-19 or variant thereof), or an HIV infection (a "therapeutically effective amount"). For example, in alternative embodiments, polypeptides used to practice methods as provided herein are administered to an individual in need thereof in an amount sufficient to treat, prevent, reverse and/or ameliorate HIV or a coronavirus such as COVID-19 or a variant thereof, such as for example a delta or omicron COVID variant strain.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, for example, Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, alternative exemplary pharmaceutical formulations for enteral or parenteral (for example, IM, IV or oral) administration of compositions used to practice methods as provided herein are in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods as provided herein can further comprise co-administration with other drugs or pharmaceuticals, for example, compositions for treating any neurological or neuromuscular disease, condition, infection or injury, including related inflammatory and autoimmune diseases and conditions, and the like, associated with HIV. For example, compositions used to practice methods as provided herein can be co-formulated with and/or co-administered with, fluids, antibiotics, cytokines, immunoregulatory agents, anti-inflammatory agents, pain alleviating compounds, complement activating agents, such as peptides or proteins comprising collagen-like domains or fibrinogen-like domains (for example, a ficolin), carbohydrate-binding domains, and the like and combinations thereof.

Bioisosteres of Compounds

In alternative embodiment, bioisosteres of compounds used to practice methods as provided herein, for example, polypeptides having a AIBP activity, are used. Bioisosteres used to practice methods as provided herein can comprise compounds, for example, AIBP polypeptides, comprising one or more substituent and/or group replacements with a substituent and/or group having substantially similar physical or chemical properties which produce substantially similar biological properties to compounds used to practice methods as provided herein. In one embodiment, the purpose of exchanging one bioisostere for another is to enhance the desired biological or physical properties of a compound without making significant changes in chemical structures.

For example, in one embodiment, one or more hydrogen atom(s) is replaced with one or more fluorine atom(s), for example, at a site of metabolic oxidation; this may prevent metabolism (catabolism) from taking place. Because the fluorine atom is similar in size to the hydrogen atom the overall topology of the molecule is not significantly affected, leaving the desired biological activity unaffected. However, with a blocked pathway for metabolism, the molecule may have a longer half-life or be less toxic, and the like.

Products of Manufacture and Kits

Provided are products of manufacture and kits for practicing the methods as described herein, optionally also including instructions for practicing methods as provided herein. In alternative embodiments, provided are kits comprising a pharmaceutical, a formulation, an implant or a device, comprising a protein or a composition having Apolipoprotein A-I binding protein (AIBP) activity.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1

Inhibition of HIV Replication by AIBP Targeting the Lipid Rafts

This example demonstrates that methods and compositions as provided herein using the exemplary embodiments are effective for treating HIV and other viral infections.

Apolipoprotein A-I binding protein (AIBP) is a recently identified innate anti-inflammatory factor. Here, we show that AIBP inhibited HIV replication by targeting lipid rafts and reducing virus-cell fusion. Importantly, AIBP selectively reduced rafts on cells stimulated by an inflammatory stimulus or treated with extracellular vesicles containing HIV-1 protein Nef, without affecting rafts on non-activated cells. Accordingly, fusion of monocyte-derived macrophages with HIV was sensitive to AIBP only in the presence of Nef. Silencing of endogenous AIBP significantly upregulated HIV-1 replication. Interestingly, HIV-1 replication in cells from donors with the HLA-B*35 genotype, associated with rapid progression of HIV disease, was not inhibited by AIBP. These results suggest that AIBP is an innate anti-HIV factor that targets virus-cell fusion.

Apolipoprotein A-I binding protein (AIBP) is a protein involved in regulation of lipid rafts and cholesterol efflux. AIBP has been suggested to function as a protective factor in several pathological conditions associated with increased abundance of lipid rafts, such as atherosclerosis and acute lung injury. Here, we show that exogenously added AIBP reduced the abundance of lipid rafts and inhibited HIV replication in vitro as well as in HIV-infected humanized mice, whereas knockdown of endogenous AIBP increased HIV replication. Endogenous AIBP was much more abundant in activated T cells than in monocyte-derived macrophages (MDM), and exogenous AIBP was much less effective in T cells than in MDM. AIBP inhibited virus-cell fusion, specifically targeting cells with lipid rafts mobilized by cell activation or Nef-containing exosomes. MDM-HIV fusion was sensitive to AIBP only in the presence of Nef provided by the virus or exosomes. Peripheral blood mononuclear cells from donors with the HLA-B*35 genotype, associated with rapid progression of HIV disease, bound less AIBP than the cells from donors with other HLA genotypes, and were not protected by AIBP from rapid HIV-1 replication. These results provide the first evidence for the role of Nef exosomes in regulating HIV-cell fusion by modifying lipid rafts and suggest that AIBP is an innate factor that restricts HIV replication by targeting lipid rafts.

Given the dependence of HIV on lipid rafts and the ability of AIBP to reduce the abundance of lipid rafts, in this study we investigated whether such activity of AIBP translates into inhibition of HIV replication. We found that AIBP inhibits HIV replication both in vitro and in vivo and reverses the pro-infectious effects of Nef-containing extracellular vesicles. New therapeutic approaches aimed at inhibition of HIV infection and HIV-associated co-morbidities via stimulation of AIBP production are provided herein.

Methods

Cells and HIV Infection

Peripheral blood mononuclear cells (PBMCs) were isolated from whole blood (purchased from NY Blood Bank) by Ficoll gradient centrifugation. Monocyte-derived macrophages (MDMs) were prepared from PBMCs by plastic adherence and differentiation for 7 days in the presence of 50 ng/ml M-CSF (Sigma) as previously described (29). HIV-1 ADA was used for infection of MDMs. Non-adherent cells (peripheral blood lymphocytes, PBLs) were activated or not with PHA (5 μg/ml) and IL-2 (20 U/ml) for 2 days prior to infection with HIV-1 LAI or primary transmitted/founder (T/F) virus, the CCR5-tropic strain pCH185.c/K3016 (30).

Recombinant AIBP

AIBP was produced in a baculovirus/insect cell system to allow for posttranslational modifications and to ensure endotoxin-free preparation. Human AIBP was cloned into a pAcHLT-C vector behind the polyhedrin promoter. The vector contains an N-terminal His-tag to enable purification and detection. Insect Sf9 cells were transfected with BD BACULOGOLD™ Baculovirus DNA and the AIBP vector to produce a baculovirus stock. Fresh Sf9 cells were infected with the AIBP producing baculovirus, cell pellets were collected after 3 days and His-AIBP was purified on Ni-NTA agarose column.

Protein was dialyzed against saline, and aliquots were stored at −80° C. AIBP was used at concentration of 0.2 μg/ml, unless indicated.

Analysis of AIBP Binding to Cells by Flow Cytometry

PBMC from donors with the following HLA-B genotypes were purchased from ALLCELLS INC™: B*35 positive (B*15:17:01/B*35:01:01, B*35:01:01/B*55:01:01, B*35:01:01/B*35:01:01, B*35:08:01/B*51:01:01); B*57 positive (B*07:02:01/B*57:01:01, B*51:01:01/B*57:01:01, B*40:01:02/B*57:01:01); non-B*35, B*57 (B*08:01:01/B*38:01:01, B*27:05:02/B*38:01:01, B*07:02:01/B*27:05:02, B*15:11:01/B*51:01:02). To analyze AIBP binding, PBMC were blocked with TBS containing 1% BSA for 30 min on ice and incubated with either 2 μg/ml BSA or recombinant His-tagged AIBP for 2 hours on ice. Cells were washed with PBS and incubated with 1 μg/ml FITC-conjugated anti-His polyclonal antibody (ABCAM™) and LIVE/DEAD Fixable Aqua Dead Cell Stain (Invitrogen) for 1 hour at 4° C. After washes with PBS, cells were analyzed by flow cytometry gating on live cells.

Analysis of AIBP Binding to Cells by Fluorescent Microscopy

PBMCs from HLA-B*35 and HLA-B*57 donors were incubated with His-AIBP as above and stained for bound AIBP with FITC-conjugated anti-His polyclonal antibody (ABCAM™) and for lipid rafts with Alexa Fluor 555-conjugated Cholera Toxin B subunit (CT-B). Cells were then mounted on microscopic glass slides, fixed, permeabilized with Triton X-100, and nuclei were stained with DAPI. Imaging and analysis were performed on a CELL OBSERVER SPINNING DISK™ fluorescent microscope (CARL ZEISS™) equipped with YOKOGAWA CSU X1™ spinning disk and EVOLVE DELTA EM™ CCD cameras (512×512, PHOTOMETRICS™). Plain APOCHROMAT™ 63×/1.46 oil objective lens was used to visualize the optical section close to the center of the majority of the cells. The camera exposure time for each channel and the emission and excitation parameters were kept constant across the experiments. DAPI was excited with a 405 diode laser, and the emission was recorded with 450/50 bandpass filter. FITC was excited with a 488 diode laser, and emission was recorded with 535/30 bandpass filter. To record the CT-B immunolabeling, a 561 diode laser was used for excitation, and the emission was recorded with 629/62 emission filter. Images were further enhanced using ZEN MICROSCOPE SOFTWARE™ (CARL ZEISS™). Again, an identical setting was used for all images. Final images were saved as TIFF files.

Mean fluorescence intensity (MFI) quantitation was performed on 108 individual cells with HLA-B*35 and 159 cells with HLA-B*57 genotype. To compute the cellular intensities for AIBP and CTB (lipid rafts), the original data stored as czi files (the Carl Zeiss Image Data file type) were used. In each image, taken with a 63× objective, every cell was evaluated using Volocity software. Individual cells were outlined using the freehand ROI tool and each cell's overall cellular fluorescent intensity was recorded for each channel. Mean fluorescence intensity (MFI) quantitation was performed on 108 individual cells with HLA-B*35 and 159 cells with HLA-B*57 genotype. To compute the cellular intensities for AIBP and CTB (lipid rafts), the original data stored as czi files (the Carl Zeiss Image Data file type) were used. In each image, taken with a 63× objective, every cell was evaluated using Volocity software. Individual cells were outlined using the freehand ROI tool and each cell's overall cellular fluorescent intensity was recorded for each channel. Outliers were removed using statistical software in the GraphPad Prism 8 program."

Isolation and Purification of Exosomes

Forty eight hours post transfection of HEK293T cells (purchased from ATCC) with pcDNA3.1 vector expressing Nef of HIV-1 NL4-3 (to make exNef) or with empty vector (to make exCont), medium from cell culture was collected. Exosomes were isolated by differential centrifugation, as described (31). Briefly, culture supernatants were pre-clarified by centrifugation at 500×g for 10 min at 4° C. to remove cells and cellular debris, then clarified by spinning at 2,000×g for 30 min at 4° C. to remove remaining debris and large apoptotic bodies, and exosomes were pelleted by centrifugation at 100,000×g for 75 min at 4° C. The pellet was re-suspended in exosome-free medium and frozen at −70° C. Of note, the pellet contained a mixture of extracellular vesicles with sizes from 25 to over 150 nm (FIG. S1), corresponding to exosomes, microvesicles, and other vesicles (32). However, since the majority of vesicles had the size of 150 nm characteristic to exosomes, we use the term exosomes' in this report. Total protein content in exosome samples was estimated by Bradford assay after dilution in RIPA buffer and boiling for 3 minutes; 1 μg of exosomes was used to treat 1×10$^6$ cells.

Nanoparticle Tracking Analysis of Exosomes

The size and the concentration of exosomes were determined using a NanoSight NS300 (Malvern Instruments Ltd, Malvern, UK) based on Nanoparticle tracking analysis (NTA). NTA utilizes the properties of both light scattering and Brownian motion to obtain the particle size distribution of samples in liquid suspension. Briefly, exosome samples from Nef- and mock (empty vector)-transfected HEK293T cells were diluted 1:100 in PBS and exosomes were tracked on the NanoSight NS300. The samples were loaded by means of a constant pressure syringe pump controller. Videos were recorded for 60 seconds two times, at camera level 13, and analyzed with NTA software 3.0 (Malvern instruments Ltd, Malvern, UK).

Fusion Assay

The fluorescence HIV-1 virion-based assay was used as previously described (33). The CCF2 substrate was purchased from Life Technology and added to cells at a final concentration of 1 μM. CCR5-tropic viruses used for MDMs were: 1) pNL(AD8), which carries Env of AD8 strain (34), used at 1×10$^6$ cpm of RT activity per 10$^6$ cells; 2) pBRNL4.3_92BR020.4(R5)nef−_IRES_GFP and pBRNL4.3_92BR020.4(R5)nef+_IRES_GFP (35), the Nef-negative and Nef-positive recombinant constructs, respectively, both used at $2\times10^6$ cpm of RT activity per $10^6$ cells. The CXCR4-tropic virus used for PBLs was pNL4-3 at $1\times10^6$ cpm of RT activity per $10^6$ cells. Cells were analyzed by flow cytometry, percentage of cells showing fluorescence at 450 nm reflects the percentage of cells fused with HIV.

Lipid Raft Analysis

Abundance of lipid rafts was evaluated by binding of cholera toxin subunit B (CT-B), as previously described (17). Briefly, cells were incubated for 1 h at 4° C. in serum-containing medium with FITC-CT-B conjugate (Invitrogen) (final concentration 0.5 µg/ml), fixed with 5% formaldehyde and analyzed by flow cytometry gating on live cells revealed by LIVE/DEAD Fixable Aqua Dead Cell Stain kit (Invitrogen).

AAV-AIBP

Murine AIBP was fused with fibronectin secretion sequence (FIB) at the N-terminus and 6×-His at the C-terminus (FIB-AIBP-His). FIB-AIBP-His was cloned into the pAAV-MCS vector (Agilent Technologies). AAV-293 cells (Agilent Technologies) were transfected with 20 µg each of pAAV-FIB-mAIBP-His, pAAV-DJ/8 (Cell Biolabs), and pHelper DNA (Cell Biolabs). Subsequent steps of virus harvest, purification and storage were according to published protocols (36). Viral DNA was extracted from purified virus and the number of gene copies (gc) was determined using qPCR with primers for the inverted terminal repeats (Takara Bio Inc).

AIBP Silencing in PBLs

Silencing was performed using Accell SMARTpool siRNA (4 siRNAs) and delivery mix (Dharmacon) following the manufacturer's protocol. AIBP target sequences were CGAGUGUGUCUAUCGUCUG (SEQ ID NO:1), UGACGAUUGAUGAACUGUA (SEQ ID NO:2), CUACUGUCCUGGUCAUCUG (SEQ ID NO:3), UCAGCGUGGACCAACUUAU (SEQ ID NO:4).

Western Blotting

Western blot analysis was performed on ProteinSimple Jess microfluidic capillary equipment, using manufacturer's software for band quantification. Unless indicated, loading control for quantification was total protein measured in the same capillary as the protein of interest, using ProteinSimple proprietary technology. Nef was detected using anti-Nef rabbit polyclonal antibody from NIH AIDS Reagent Program (37) followed by secondary goat anti-rabbit-Green (ProteinSimple), for p55 we used and anti-p24 mouse monoclonal (AG3.0) from NIH AIDS Reagent Program (38), followed by secondary goat anti-mouse-Red (PROTEINSIMPLE™). For AIBP detection, rabbit polyclonal anti-AIBP from Novus Biologics was used, followed by anti-rabbit-HRP from PROTEINSIMPLE™.

MTT Assay

Cell metabolic activity was measured by the MTT Assay Kit (ABCAM™) following manufacturer's instructions.

Humanized Mice

Memory CD4$^+$ T-cells were isolated from PBMCs (PERIPHERAL BLOOD LEUKO PAK™, ALLCELLS™) by negative selection (EASYSEP HUMAN MEMORY CD4$^+$ T CELL ENRICHMENT KIT™, STEMCELL TECHNOLOGIES™) following the manufacturer's instructions. Isolated memory CD4$^+$ T-cells were then engrafted into 7 to 9-week-old NOD. Cg-Prkdc$^{scid}$Il/2rg$^{tm1wjl}$/SzJ (NSG) mice (THE JACKSON LABORATORY™) at $10^7$ cells per animal via tail vein injection. Peripheral blood was collected weekly post-engraftment by tail nick to assess human cell reconstitution by flow cytometry and to measure HIV viral load (see below). Two weeks after CD4$^+$ T-cell engraftment, mice were intravenously injected with empty virus or AAV-AIBP at $1\times10^{12}$ gc/mouse, and after two more weeks were infected with 70,000 TCID$_{50}$/animal of HIV-1 ADA virus via intraperitoneal injection. Animals were sacrificed at the study conclusion, and liver samples and peripheral blood were collected.

Flow Cytometry of Cells from Hu-Mice

Peripheral blood cells from hu-mice were resuspended in a staining cocktail of anti-human CD27 (clone 0323, BIOLEGEND™), CD197 (clone G043H7, BioLegend), CD45RA (clone HI100, BD BIOSCIENCES™), CD8a (clone RPA-T8, BIOLEGEND™), CD4 (clone RPA-T4, BD BIOSCIENCES), CD3 (clone SK7, BD BIOSCIENCES™), and COUNTBRIGHT ABSOLUTE COUNTING BEADS™ (for cell quantification, THERMOFISHER™). Red blood cells were lysed in RBC LYSIS/FIXATION SOLUTION™ (BIOLEGEND™), and the remaining cells were fixed with 4% paraformaldehyde. Fixed cells were analyzed by flow cytometry on an LSRFORTESSA X-20 CELL ANALYZER™ (BD).

HIV Viral Load

Viral RNA was extracted from cell-free plasma using the QLAAMP VIRAL RNA MINI KIT™ (QIAGEN™) following the manufacturer's instructions. HIV viral RNA was quantified by qRT-PCR using the integrase single-copy assay (iSCA) (39). Reactions were performed with the AGPATH-ID ONE-STEP RT-PCR™ kit (APPLIED BIOSYSTEMS™), using 400 nM primers (forward primer: 5'-TTTGGAAAGGACCAGCAAA-3' (SEQ ID NO:5); reverse primer: 5'-CCTGCCATCTGTTTTCCA-3') (SEQ ID NO:6) and 250 nM dual-labeled probe (probe: 5'-6FAM-AAAGGTGAAGGGGCAGTAGTAATACA-TAMRA-3') (SEQ ID NO:7) targeting a highly conserved 127 base pair region of HIV integrase gene. Absolute quantifications were established by comparison to a standard curve of in vitro transcribed HIV-1 RNA standards generated by cloning the p31 region of pol from plasmid pNL4-3 containing an infectious clone of HIV-1 (GenBank ascension number: K02013). PCR was first used to generate a 418 base pair amplicon from pNL4-3 using 600 nM primers (forward primer: 5'-CCCTACAATCCCCAAAGTCA-3' (SEQ ID NO:8); reverse primer: 5'-CACAATCATCACCTGCCATC-3') (SEQ ID NO:9). The resulting amplicon was cloned into the PGEM T-EASY VECTOR™ (PROMEGA™) downstream of the T7 promoter. Plasmid containing the correct insert was linearized with SacI, and in vitro RNA synthesis was performed with a 4-hour incubation at 37° C. using the MEGASCRIPT T7 TRANSCRIPTION KIT™ THERMOFISHER™). Template DNA was degraded by treatment with RQ1 RNASE-FREE DNASE™ (PROMEGA™), and RNA was purified with the RNEASY MINI KIT™ (QIAGEN™) followed by dNTP removal (QIAGEN™). Purified RNA was quantified using spectrophotometry at 260 nm, diluted in 5 mM Tris, 1 µM DTT and 1,000 units/mL of recombinant RNasin ribonuclease inhibitor (PROMEGA™), and stored at −80° C. until use.

Statistical Analysis

The experiments were conducted in triplicates and repeated 2-5 times. Statistical significance of the differences was assessed, unless indicated otherwise) by ordinary one-way ANOVA with Tukey adjustment for multiple comparisons (when 3 or more samples were compared), or by t-test with Bonferroni-Dunn adjustment for multiple comparisons (when repeated measures of 2 samples were compared) in GRAPHPAD PRISM 8™ software package, $p<0.05$ was considered significant.

Ethics Statement

All animal procedures in this study were conducted under IACUC protocol A333 approved by The George Washington University in compliance with the Animal Welfare Act and in accordance with the principles set forth in the "Guide for the Care and Use of Laboratory Animals".

Results

AIBP Inhibits HIV Replication In Vitro

In previous studies, AIBP concentration of 0.2 µg/ml was found to be an effective dose for stimulation of cholesterol efflux from myeloid cells (5, 6, 8, 9). It is important to note that AIBP activity depends on the presence of apoA-I, so all experiments measuring functional activity of AIBP were done in the presence of 10% human serum as a source of apoA-I. To test the effect of AIBP on HIV replication, we first titrated the effect of baculovirus-expressed recombinant AIBP on MDM infection by HIV-1 ADA. Results in FIG. 1A demonstrated that at 0.2 µm/ml concentration, AIBP significantly reduced the amount of HIV-1 in the culture medium at day 12 post infection. To be consistent with previous studies, we chose this concentration for subsequent experiments.

Figure 1B:
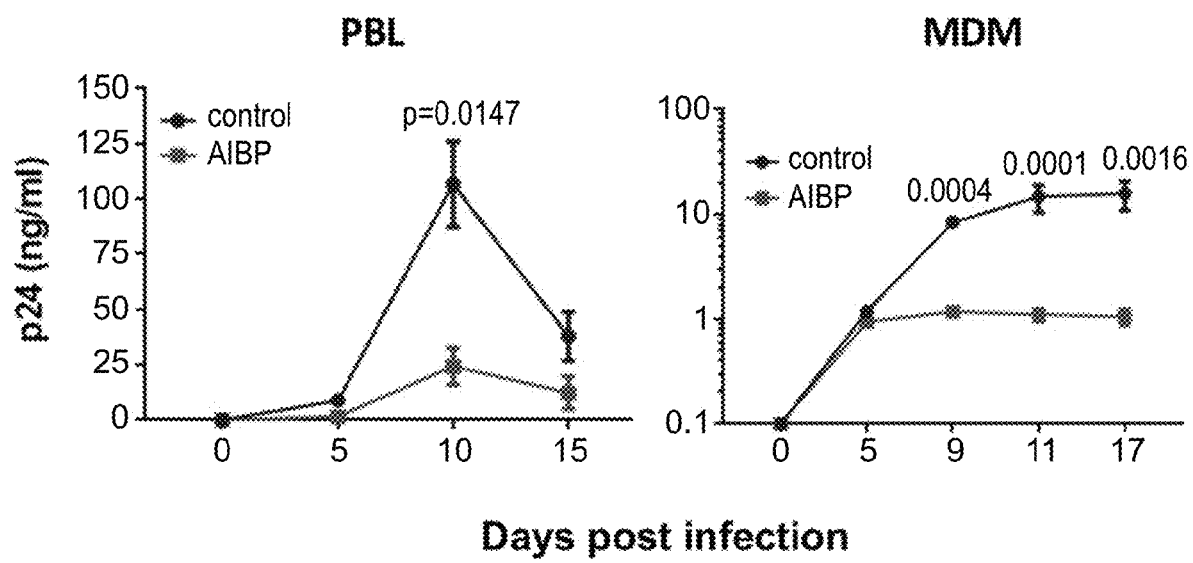
Figure 1C:
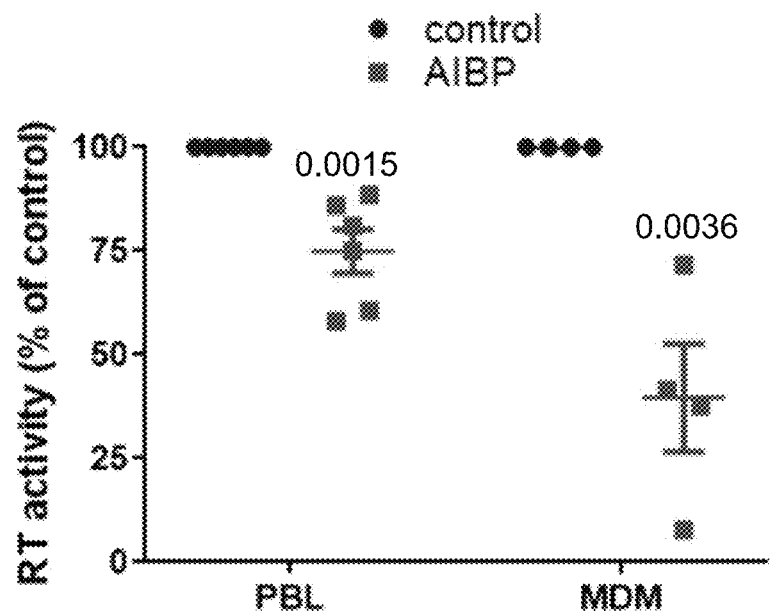
FIG. 1C graphically illustrates data from the experiment as performed as in FIG. 1B, with PHA-activated PBL from 6 donors and MDM from 4 donors, and virus replication was followed by RT activity, and results are presented for each donor at the peak of infection as percent of RT activity in AIBP-negative (control) culture.

Analysis of HIV replication kinetic in PBL and MDM cultures infected with X4 (LAI) or R5 (ADA) HIV-1 strains, respectively, demonstrated significant suppression by AIBP of HIV-1 replication in both PBLs and MDMs (FIG. 1B). As a control in the initial experiments, we used baculovirus-expressed recombinant human alpha-Fetoprotein (AFP). This protein produced no effect on HIV replication in PBLs (FIG. 1D and FIG. S2), so in most subsequent experiments BSA was used as a negative control. The mean inhibition of HIV replication by AIBP relative to cultures with no added AIBP calculated with cells from several different donors was over 50% for MDM and about 25% for PBL cultures (FIG. 1C).

Figure 1D:
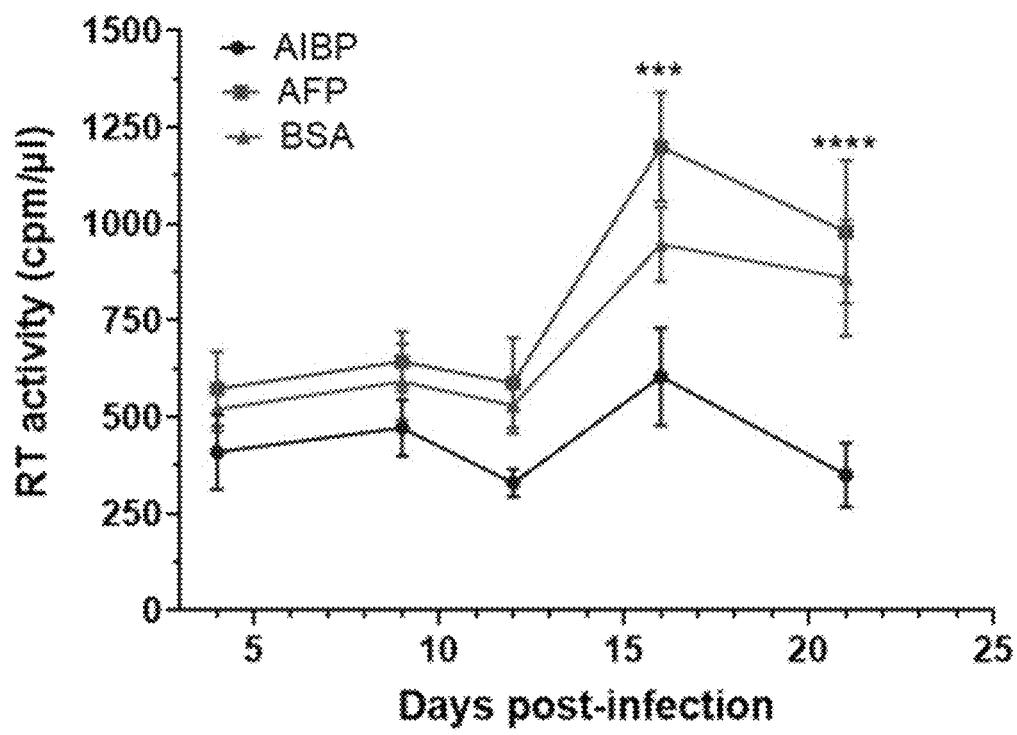
FIG. 1D graphically illustrates data from PHA-activated PBLs infected with T/F strain pCH185.c/K3016 and cultured in the presence or absence of 0.2 µg/ml recombinant AIBP (recombinant AFP was used as control), and virus replication was followed by RT activity.
Figure 1E:
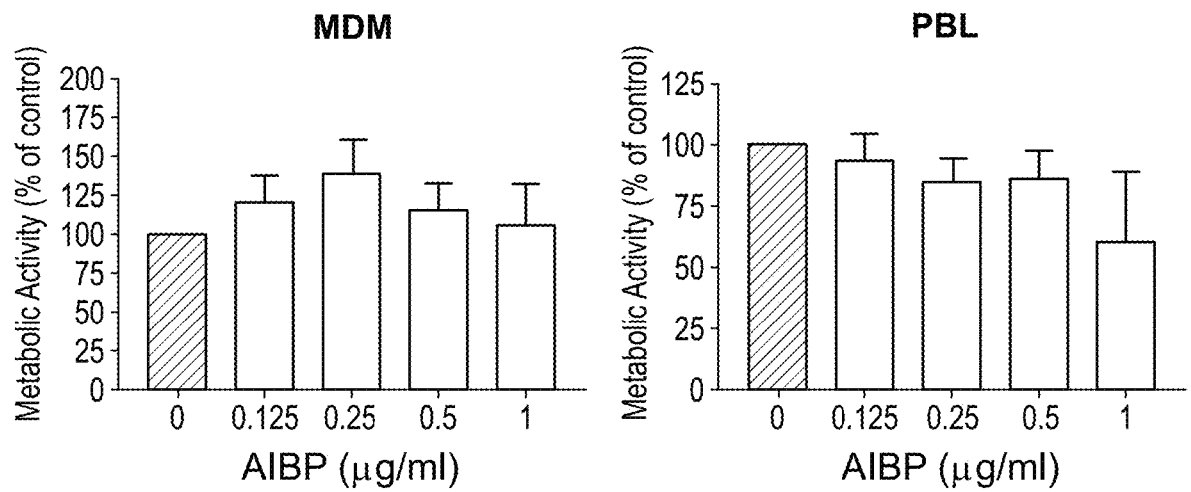
FIG. 1E graphically illustrates data showing PHA-activated PBLs and MDMs exposed to indicated concentrations of recombinant AIBP for 3 days, and cytotoxic effect of AIBP was measured by MTT assay and presented as percent of metabolic activity of AIBP-negative (control) cultures.
Figure 1F:
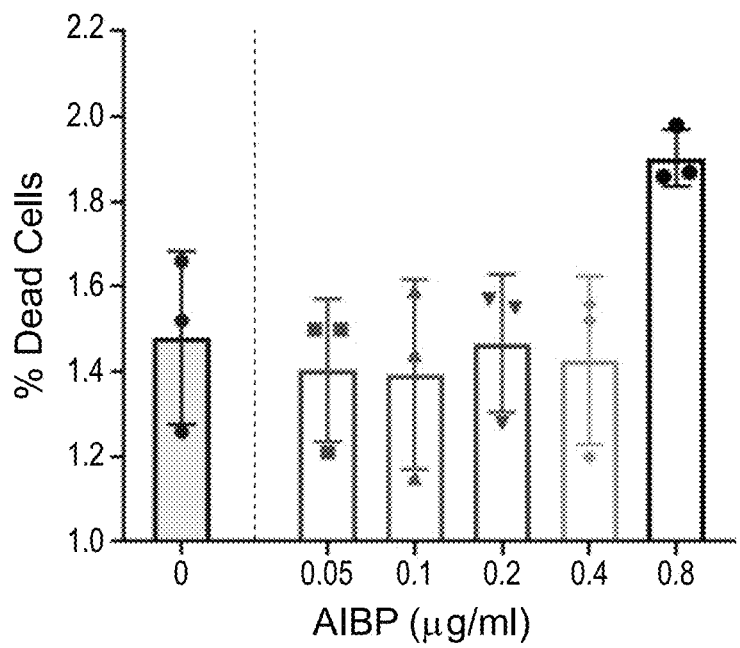
FIG. 1F graphically illustrates data showing PHA-activated PBLs treated with AIBP as in FIG. 1C, and percentage of live cells was measured by flow cytometry using LIVE/DEAD FIXABLE AQUA™ kit (INVITROGEN™)
Figure 1G:
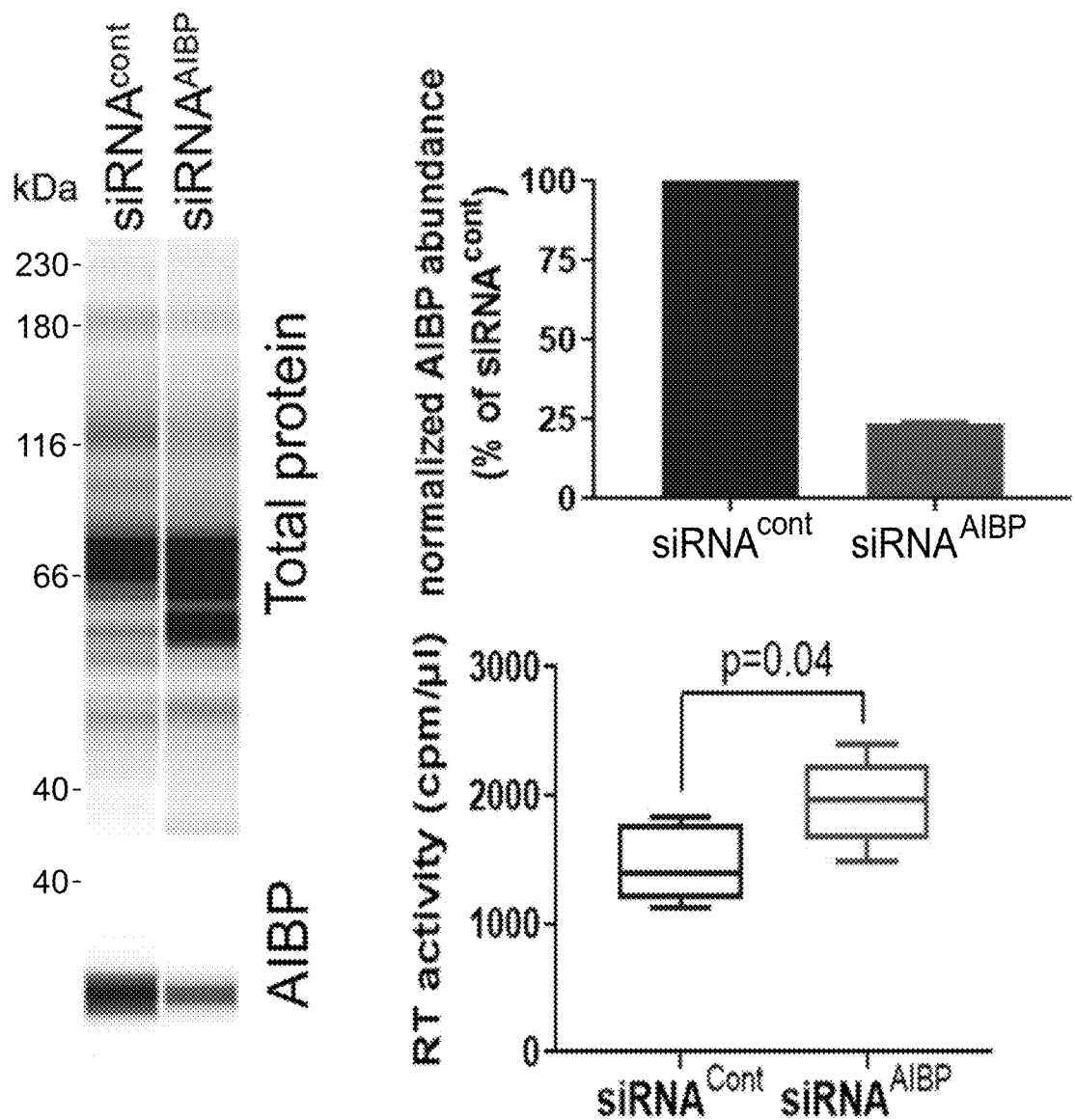
FIG. 1G graphically illustrates data showing PHA-activated PBLs treated with AIBP-targeting or control ACCELL™ siRNA for 72 hours (h), and AIBP abundance was measured by PROTEINSIMPLE™ Western blotting (left panel), normalized against total protein, and presented relative to cells treated with siRNA$^{Cont}$ (right top panel), and cells were infected in 5 wells with HIV-1$_{LAI}$, cultured for 3 days, and HIV production was measured by RT activity in culture supernatant (right bottom panel)
Figure 1H:
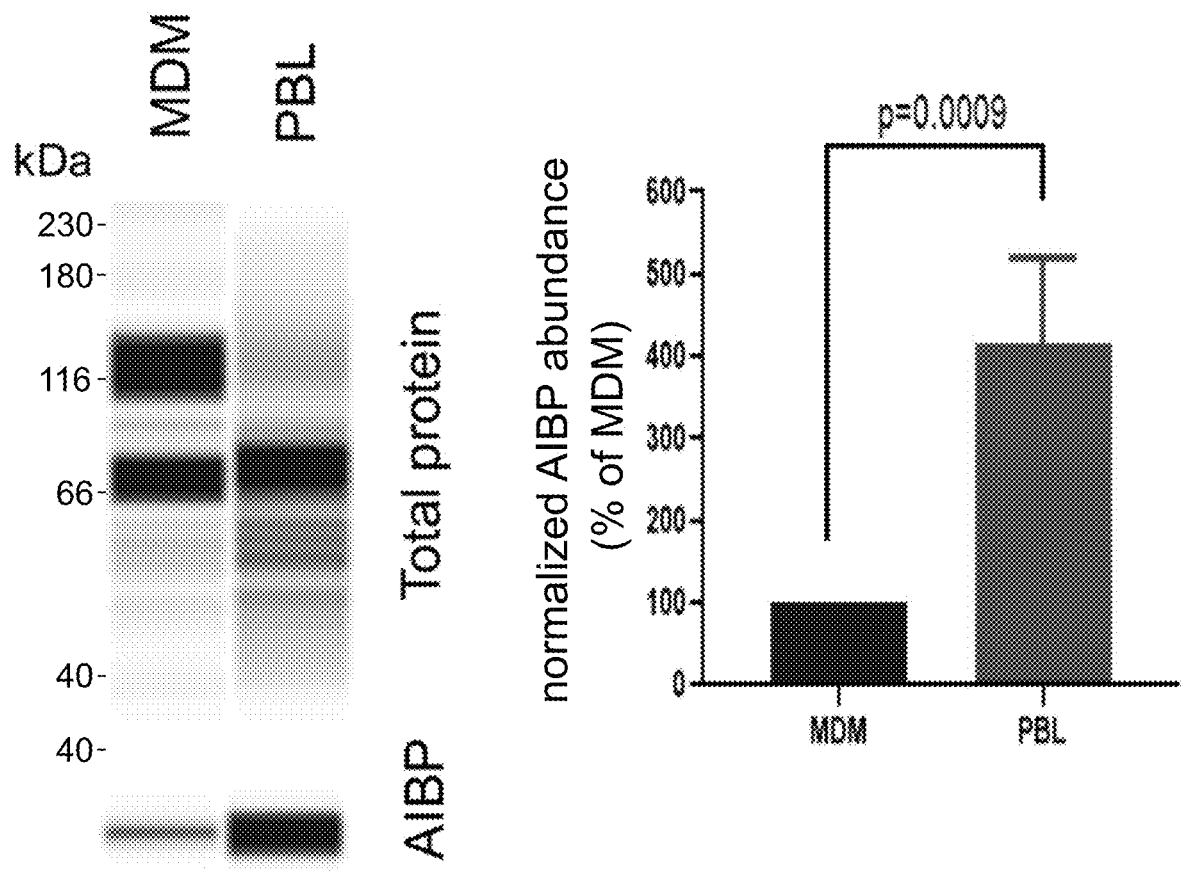
FIG. 1H graphically illustrates data showing PBLs and MDMs from the same donor analyzed in triplicate for AIBP by PROTEINSIMPLE™ Western blotting (left panel), and relative abundance of AIBP normalized against total protein is shown in the right panel, as further discussed in Example 1, below.

Laboratory-adapted HIV strains, such as R5-ADA and X4-LAI used above, are less predictive of in vivo outcomes than strains mediating transmission between HIV-positive individuals, also known as transmitted/founder (T/F) viruses, which consistently display CCR5 co-receptor tropism (40, 41). We thus tested the effect of AIBP on replication of the primary T/F virus, the CCR5-tropic strain pCH185.c/K3016 (30). This virus did not replicate in MDM, consistent with previous report (30) and ex vivo data showing that the primary targets of transmitted HIV-1 are CD4$^+$ T cells and not macrophages (42). In PBLs, AIBP noticeably suppressed replication of pCH185.c/K3016 (FIG. 1D). No toxicity of AIBP was revealed by the MTT assay (FIG. 1E), and LIVE/DEAD flow cytometry assay confirmed exclusion of necrotic and apoptotic cells (FIG. 1F). Finally, to determine whether endogenously expressed AIBP exerts an anti-HIV activity, we treated PBLs with AIBP-targeting or control siRNA prior to infection with HIV-1. This treatment reduced the abundance of AIBP by over 70% in cells treated with AIBP-specific siRNA relative to control (scrambled) siRNA (FIG. 1G, left and top right panels). HIV replication was significantly increased in cells with knocked down AIBP (FIG. 1G, bottom right panel). Of note, AIBP expression in PHA-activated PBLs was substantially higher than in MDM (FIG. 1H), explaining the difference between these cell types in the magnitude of anti-HIV activity of exogenously added AIBP. Overall, although observed inhibition was relatively modest, it provided the first evidence that AIBP can exert the anti-HIV activity. Robustness of this observation was supported by multiple HIV-1 strains susceptible to the AIBP-mediated inhibitory activity, which was reproduced with cells from multiple donors.

AIBP Targets Lipid Rafts

Figure 2A:
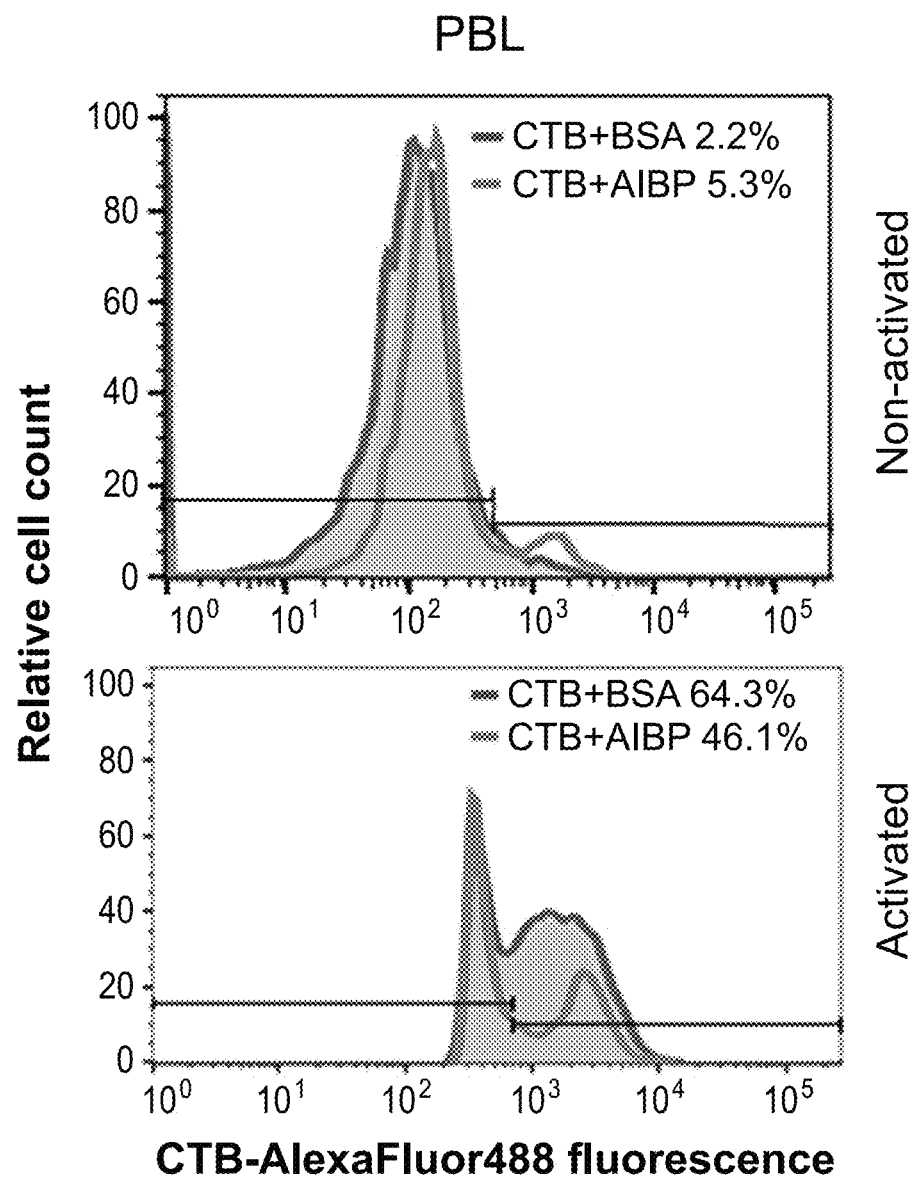
FIG. 2A-E illustrate data showing that AIBP regulates abundance of lipid rafts.
Figure 2B:
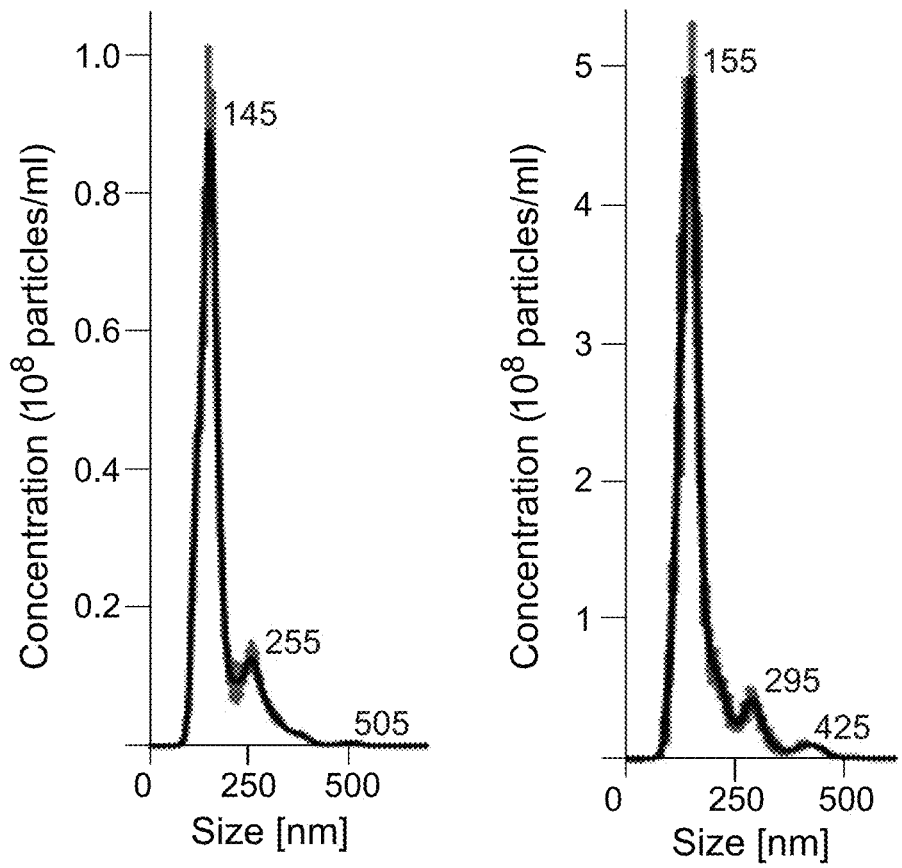
Figure 2C:
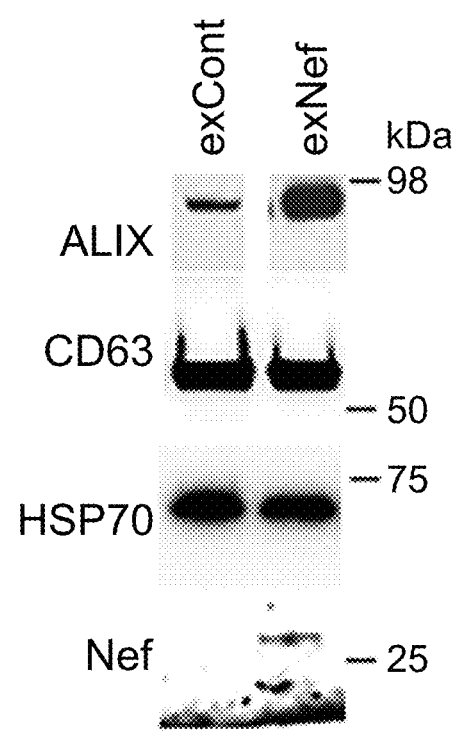
Figure 2D:
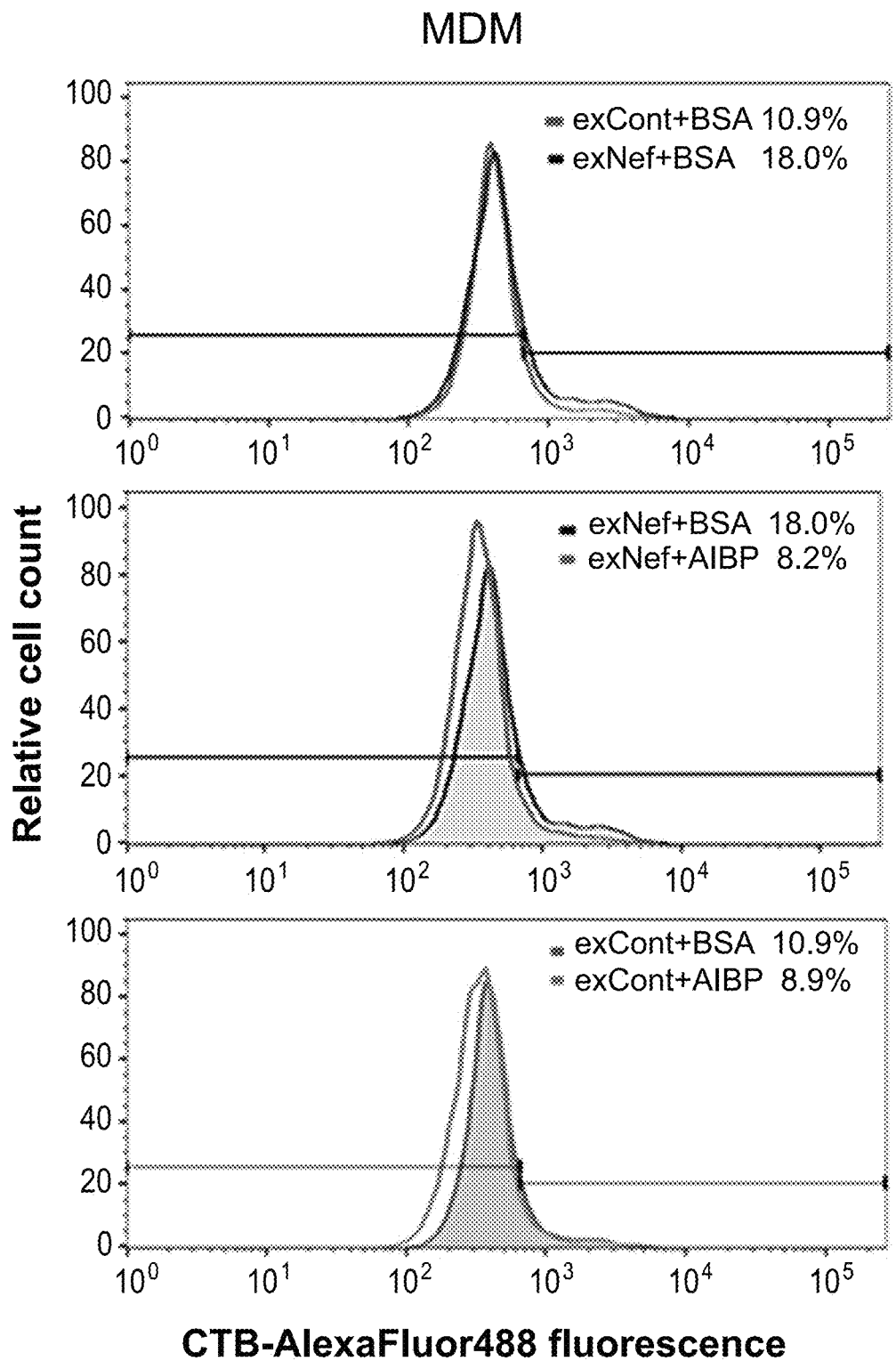
Figure 2E:
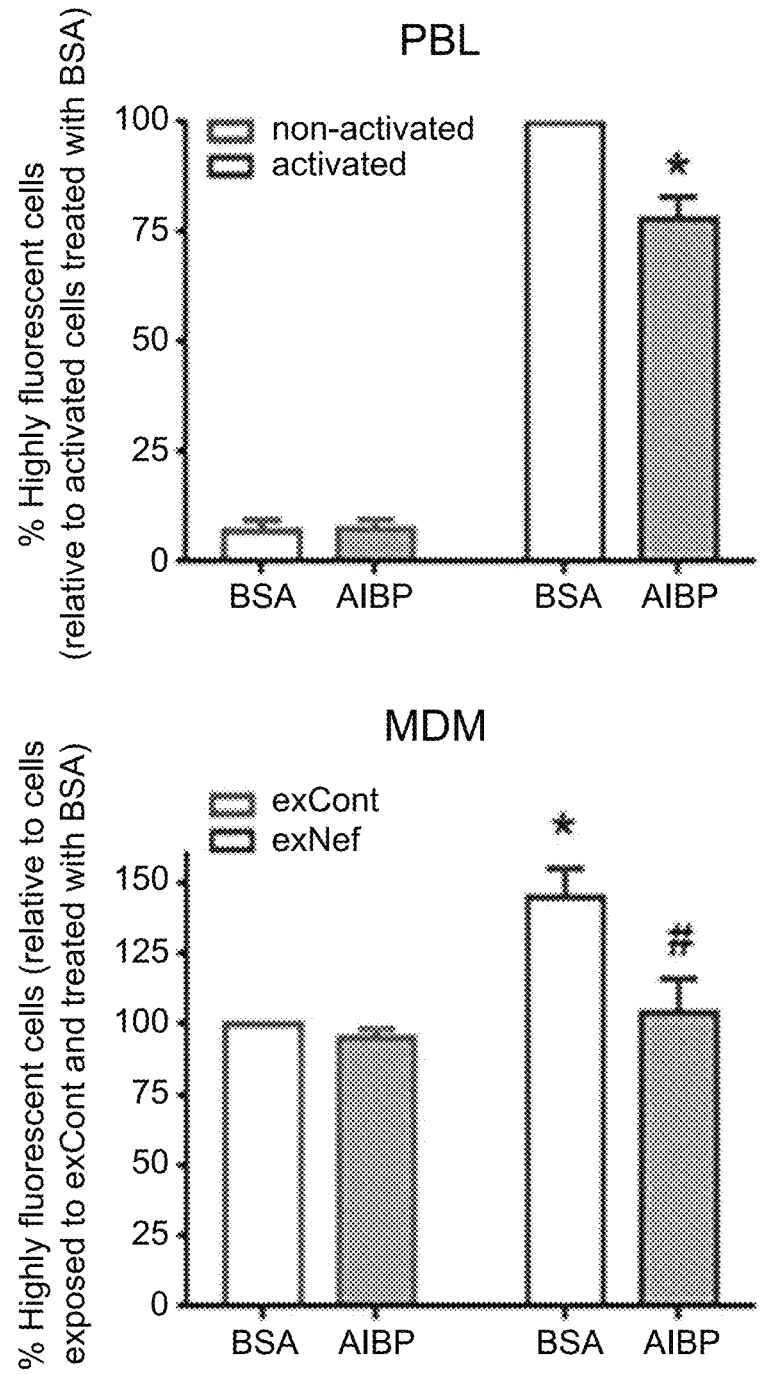

Given that AIBP reduces the abundance of lipid rafts (5), we hypothesized that the mechanism of HIV inhibition by AIBP might involve suppression of virus-cell fusion, which relies on rafts (43). Previous studies demonstrated that AIBP reduces lipid rafts on activated, but not on non-activated, macrophages, endothelial and glial cells (5, 7). Nothing has been reported about the effects of AIBP on T cells. Using fluorescently labeled cholera toxin B subunit (CTB), which specifically binds to the raft-associated ganglioside GM1 (44) and is commonly used to assess lipid raft abundance (45-47), we evaluated the effect of AIBP on lipid rafts of PBLs activated or not with PHA. In non-activated PBLs, the percentage of cells with high intensity signal was very small, suggesting a low abundance of lipid rafts (consistent with previously reported findings (48, 49)), and AIBP did not decrease the raft abundance (in fact, in this donor AIBP increased the rafts) (FIG. 2A and FIGS. S3A and B). In contrast, in PHA-activated cells the abundance of rafts was high, and was reduced by AIBP (FIG. 2A). In macrophages, AIBP has been reported to reduce rafts on LPS-stimulated cells (7). However, LPS inhibits HIV infection of macrophages by downregulating CCR5 and inducing post-entry degradation of viral RNA, therefore, increased abundance of lipid rafts in LPS-treated macrophages does not translate into increased HIV infection (50, 51). Another agent upregulating lipid rafts on macrophages is the HIV protein Nef (17). Our recent study (52) demonstrated that the same effect on lipid rafts is produced by Nef-containing exosomes (exNef). We collected exNef from supernatants of HEK293T cells transfected with Nef$_{NL4-3}$-expressing vector. Control exosomes (exCont) were collected from HEK293T cells transfected with empty vector. Of note, no difference was found between the effects on ABCA1 and lipid raft abundance by exosomes produced by cells transfected with empty vector and vector expressing GFP used as control in the previous study (52). We now analyzed the exosomes using NANOSIGHT™ (FIG. 2B). The majority of exosomes had the size of 150 nm characteristic for these vesicles (53). Consistent with this classification, the vesicles were positive for exosomal markers ALIX and tetraspanin CD63, and also carried cytoplasmic protein Hsp70 (FIG. 2C), thus fulfilling the requirements of the International Society for Extracellular Vesicles (ISEV) for exosome purity (54). Treatment of macrophages with exNef increased the percentage of highly fluorescent CTB-stained cells from 10.9% to 18.0% (FIG. 2D, top panel, and FIG. S3C). Remarkably, added recombinant AIBP reduced lipid rafts on exNef-treated macrophages to the levels observed in non-activated cells (FIG. 2D, middle panel). Statistical analysis performed with cells from 4 different donors confirmed that AIBP did not significantly change the abundance of lipid rafts on non-activated PBLs, but significantly (p=0.0088) reduced rafts on PHA-activated PBLs (FIG. 2E, left panel) and on exNef-treated MDM (p=0.0129, FIG. 2E, right panel). Of note, exNef significantly (p=0.0038) increased the abundance of lipid rafts on MDM (FIGS. 2D, top panel, and 2E, right panel). This result is consistent with our recent report (52), where we also demonstrated that the effect on lipid rafts of exNef was identical to the effect of exosomes produced by cells infected with Nef-expressing HIV-1. The effect of AIBP on lipid rafts in macrophages that were exposed to control exosomes was not significant (FIG. 2E, right panel). Together, these results are consistent with suggestion that AIBP specifically targets lipid rafts modified by inflammatory or pathological agents and reduces raft abundance to normal levels.

AIBP Inhibits Fusion Between HIV-1 and Target Cells

Figure 3A:
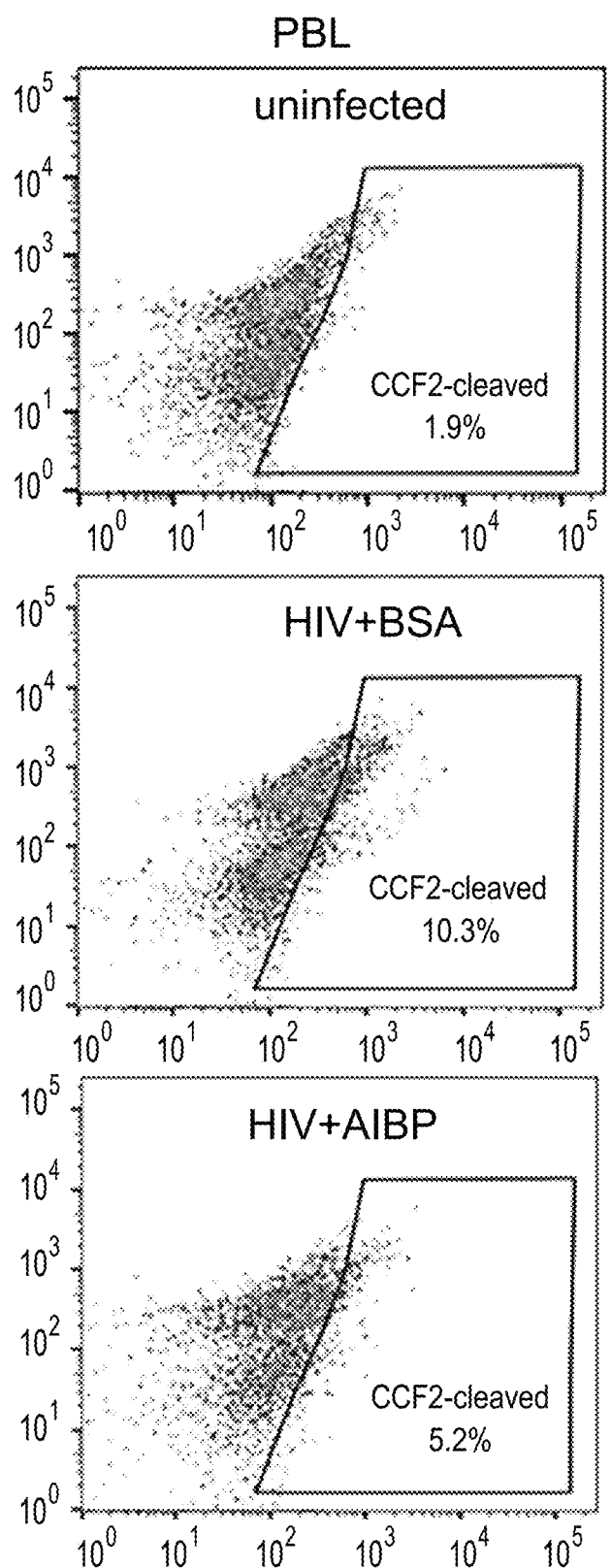
FIG. 3A-G illustrates data showing that AIBP inhibits HIV fusion with target cells.
Figure 3B:
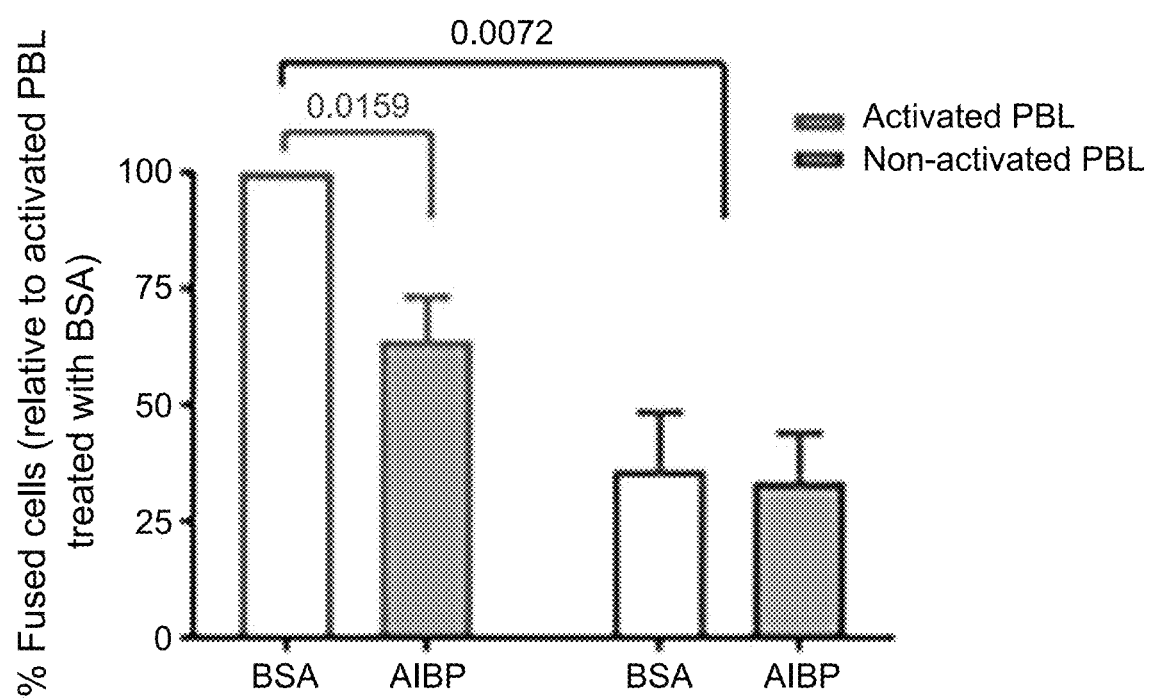
Figure 3C:
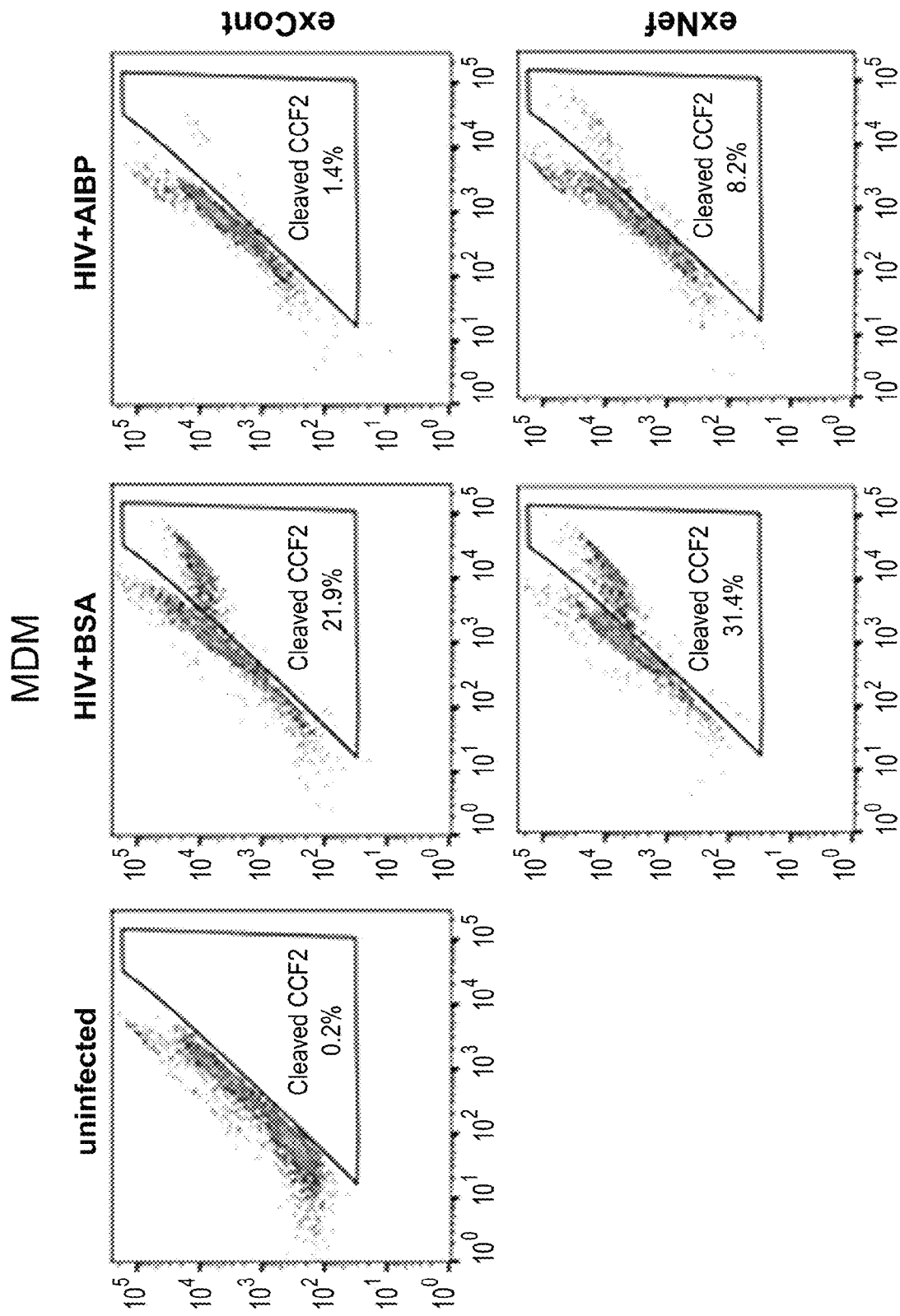
Figure 3D:
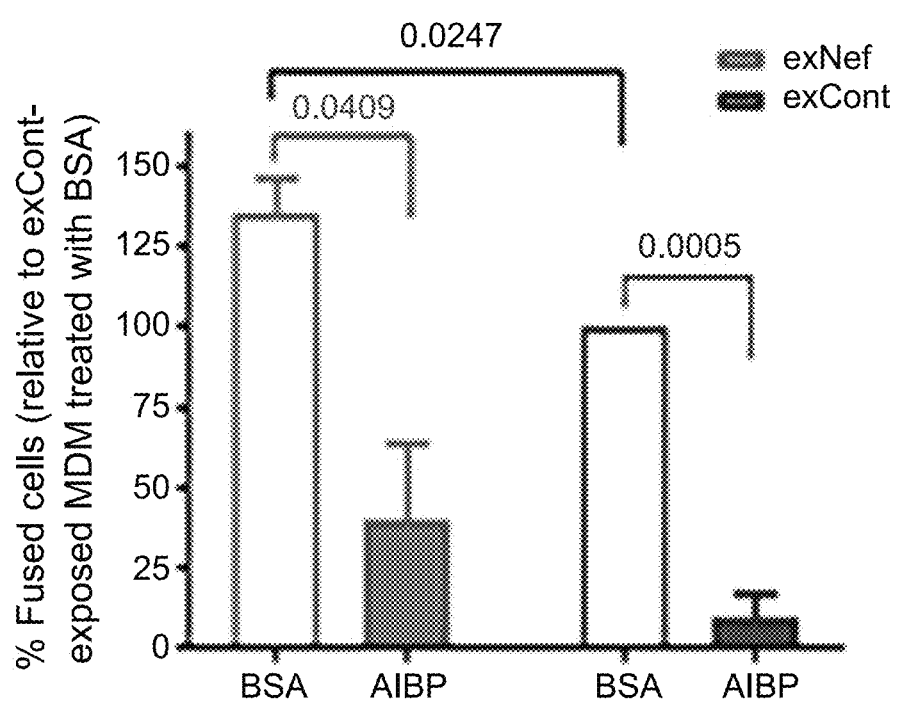

Virus-cell fusion was analyzed by fluorescent HIV-1 virion-based assay (33). For the assay with PBLs, we used the CXCR4-tropic HIV-1 NL4.3 virus containing BlaM-Vpr. This analysis demonstrated that AIBP inhibits fusion between HIV-1 and PHA-activated PBLs (FIG. 3A and FIG. S4A). The inhibitory effect was consistent between cells from different donors, was significant (p=0.0159) and averaged 40±10% inhibition (FIG. 3B). Fusion between HIV-1 and non-activated PBLs was much less effective (approximately 70% less than with PHA-activated cells) and was not inhibited by AIBP (FIG. 3B). We then analyzed the effect of AIBP on HIV-1 fusion with macrophages treated or not with exNef. For this assay, we used the CCR5-tropic HIV-1 pNL(AD8) (34). As expected, AIBP significantly (p=0.0409) inhibited fusion with HIV-1 of MDM treated with exNef (FIGS. 3C, D). Fusion with HIV-1 of MDM treated with exCont was significantly lower (p=0.0247), but, surprisingly and in seeming contradiction to the effects on lipid rafts (FIG. 2D), was also significantly suppressed by AIBP (p=0.0005, FIGS. 3C, D and FIG. S4B). This effect was consistent between the donors and averaged over 80% inhibition for cells treated with exCont and over 70% for cells treated with exNef (FIG. 3D). A possible explanation for this controversy is that Nef within HIV virions, or exNef contaminating virion preparations (55, 56) modified lipid rafts on target cells making them susceptible to AIBP. Of note, fusion inhibitor T-20 (1 µg/ml) inhibited fusion by over 90% (FIG. S5).

Figure 3E:
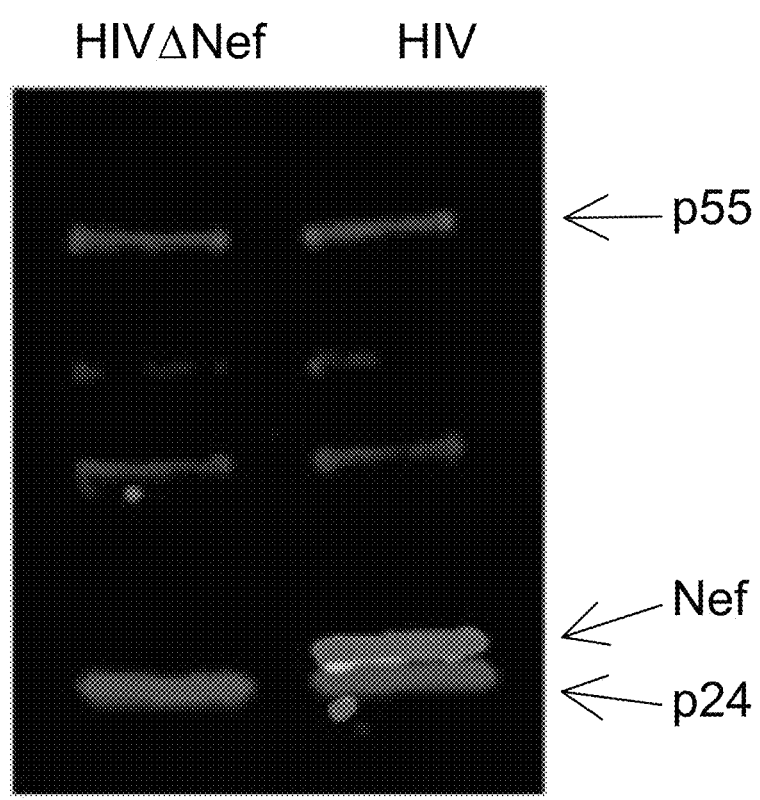
Figure 3F:
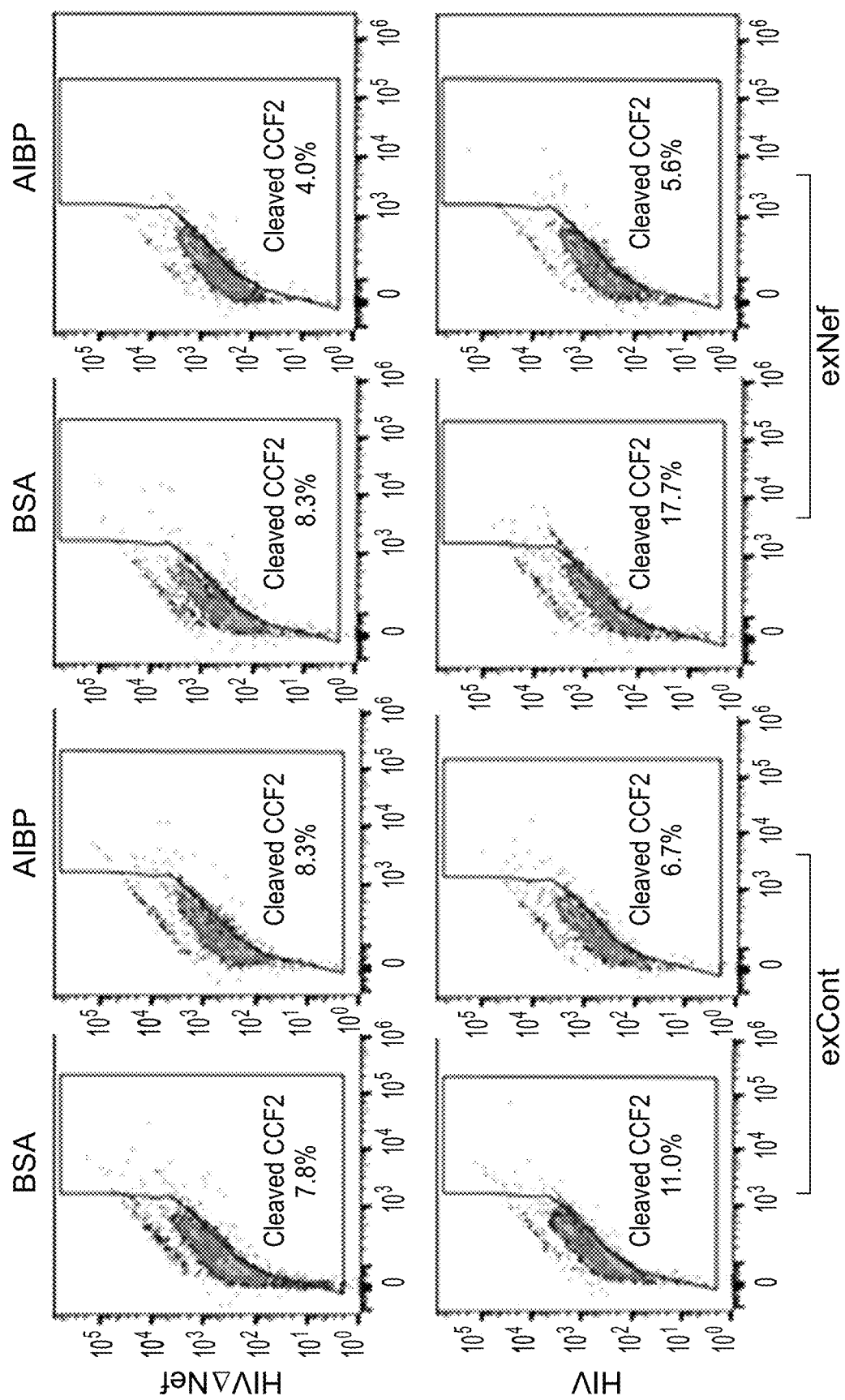
Figure 3G:
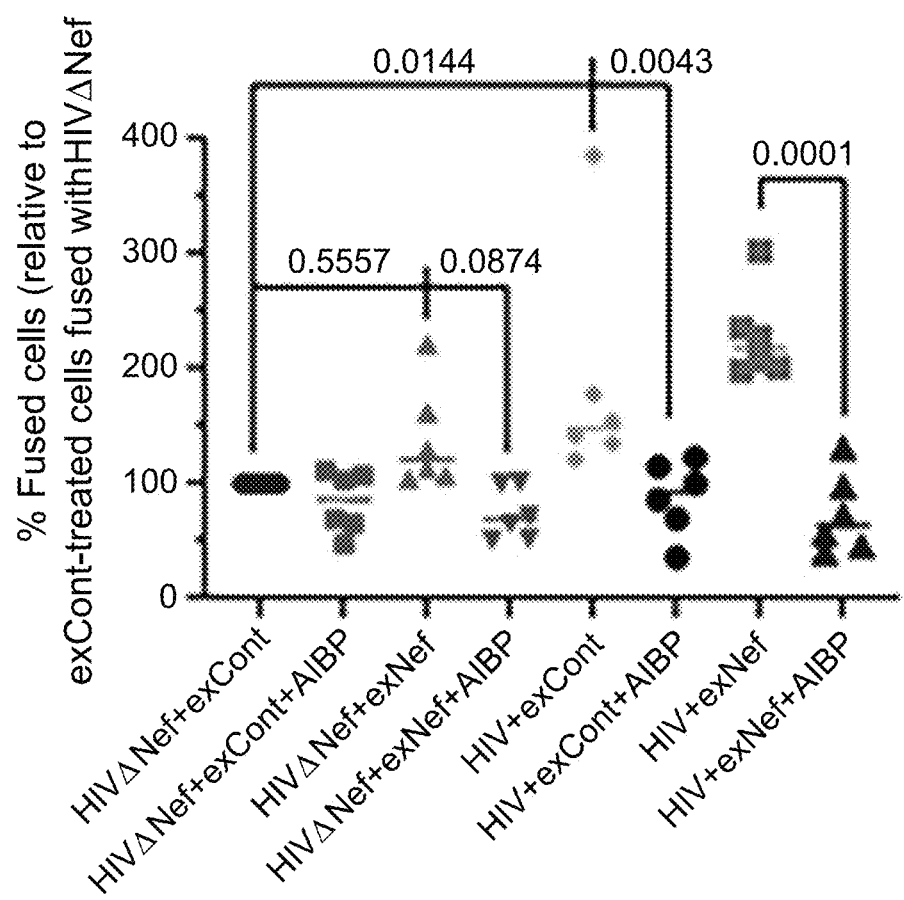

To test the possibility that Nef makes MDM-HIV fusion susceptible to AIBP-mediated inhibition, we compared the effect of AIBP on fusion between MDM, exposed to exCont or exNef, and Nef-positive (HIV) or Nef-deficient (HIVΔNef) HIV-1 (FIG. 3E). The assay was performed with the CCR5-tropic NL4-3 constructs carrying recombinant gp120 with the CCR5-targeting V3 loop (35). Consistent with results shown in FIGS. 3C and D, AIBP inhibited fusion of exCont-treated MDM with Nef-positive HIV-1 (FIG. 3F and FIG. S4C). It is important to recognize that fusion with this virus was less efficient than with pNL(AD8), which carries a full envelope of the CCR5-tropic virus (compare results in FIGS. 3F and 3C), and the observed differences were relatively small. We therefore confirmed these findings using MDM from 5 more donors (total n=6). Fusion of MDM with HIVΔNef was consistently increased by treatment with exNef relative to exCont treatment (FIG. 3G), but the difference was not significant (p=0.5557). However, fusion of MDM with Nef-positive HIV was significantly more efficient than with HIVΔNef (p=0.0144). This result appears to contradict two published reports that did not find any effect of Nef on fusion (57, 58). A likely explanation is that those studies were done with T cell lines or PHA-activated CD4+ T cells, which have high levels of lipid rafts (FIG. 2A) that are not influenced by Nef. AIBP did not affect fusion of exCont-treated MDM with HIVΔNef. However, fusion with HIVΔNef of MDM exposed to exNef trended to be reduced by AIBP, although the difference did not reach significance (p=0.0874). Fusion of MDM with Nef-positive HIV-1 was inhibited by AIBP regardless of the presence of exNef (FIG. 3G). Therefore, the effect of AIBP on HIV-1-macrophage fusion is dependent on the presence of Nef, either carried by the virus or delivered by exosomes.

Taken together, these results indicate that AIBP inhibits HIV infection by suppressing virus-cell fusion.

Anti HIV Effect of AIBP In Vivo

Figure 4A:
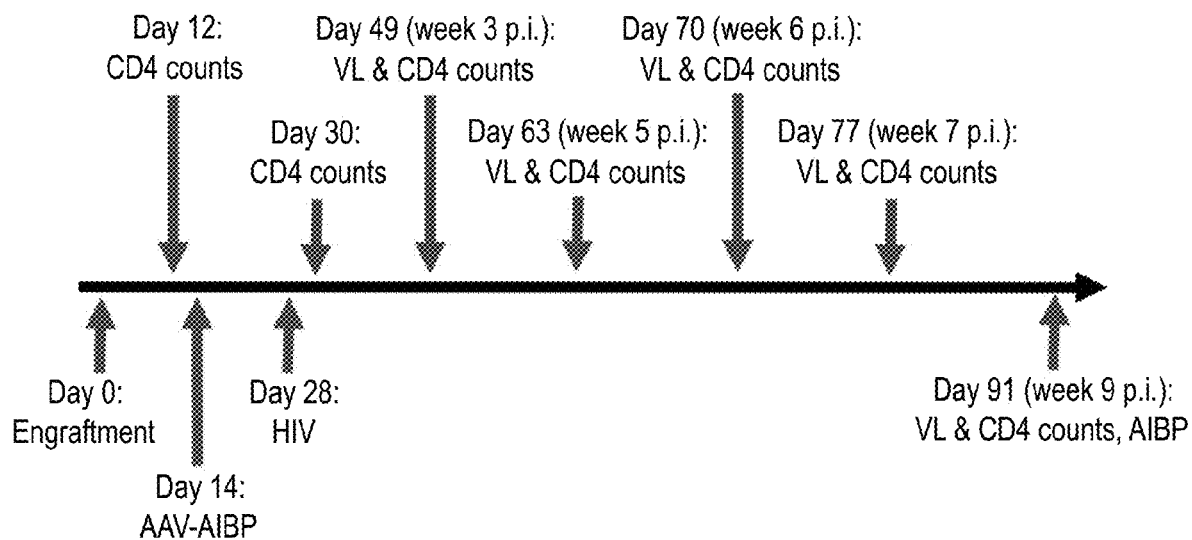
FIG. 4A-F illustrate data showing that AIBP reduces HIV load and reverses ABCA1 downregulation in liver cells.
Figure 4B:
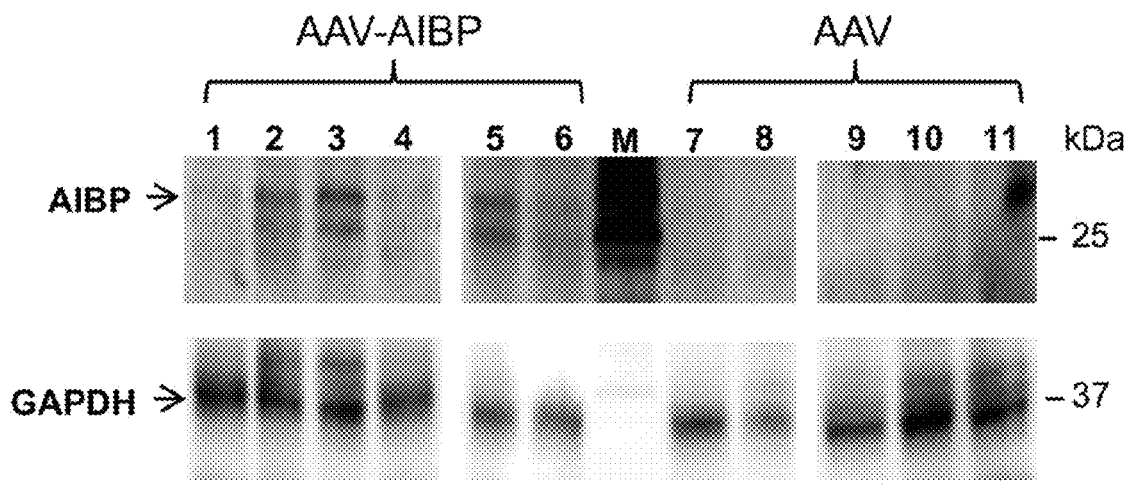
Figure 4C:
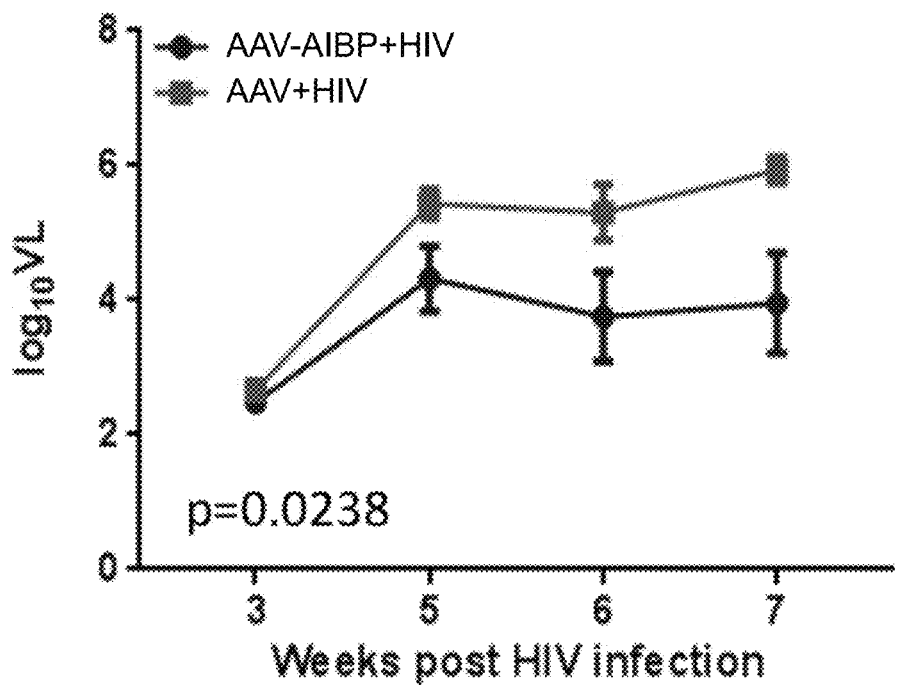
Figure 4D:
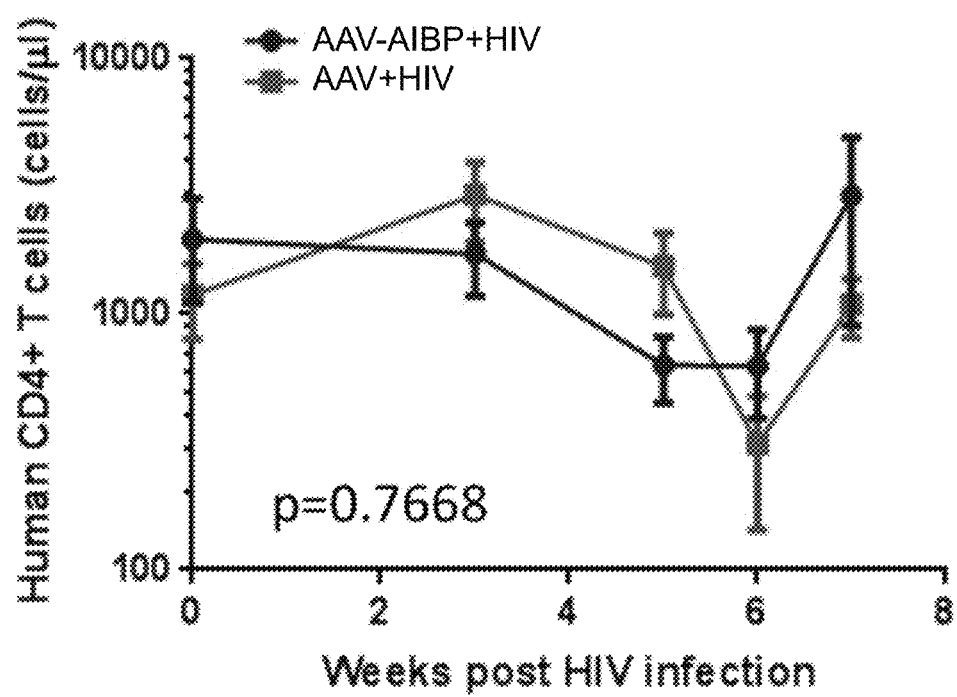
Figure 4E:
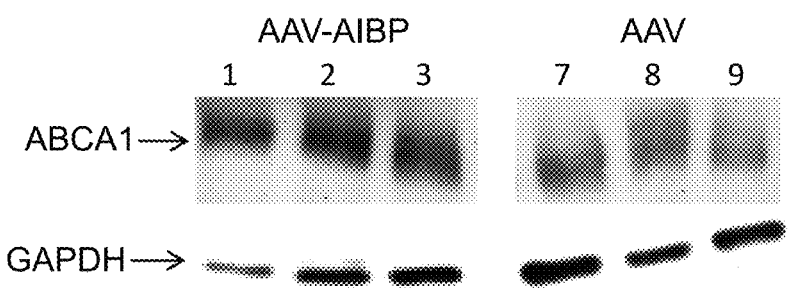
Figure 4F:
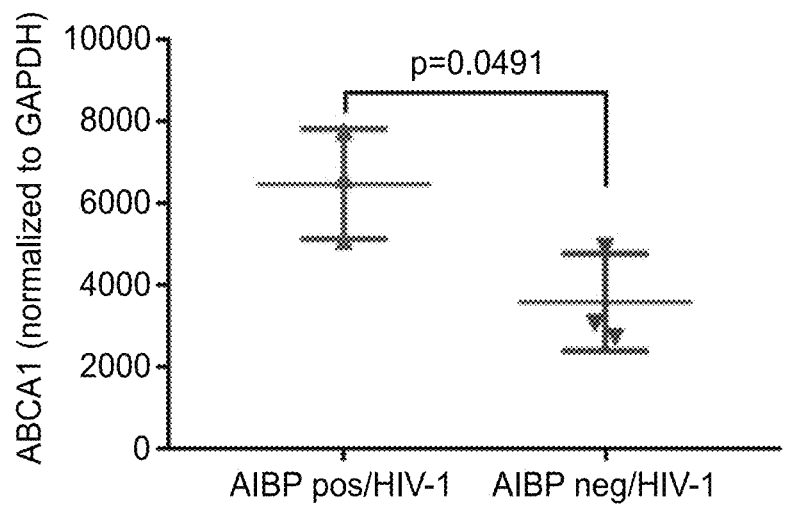
Figure 4F:
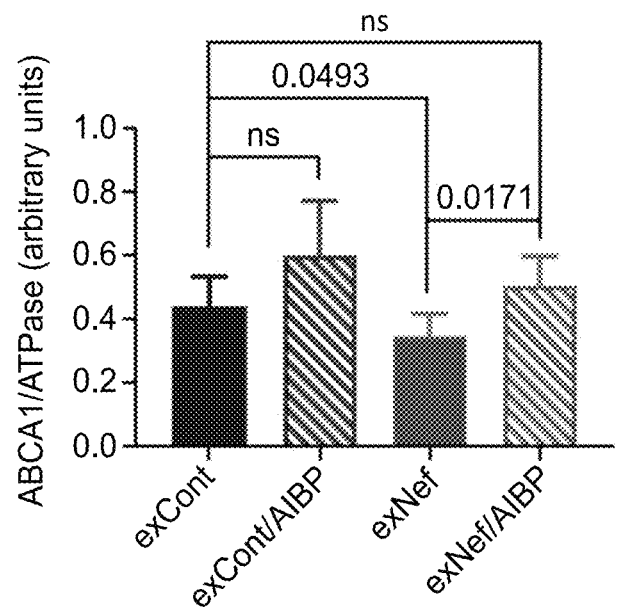
Figure 4G:
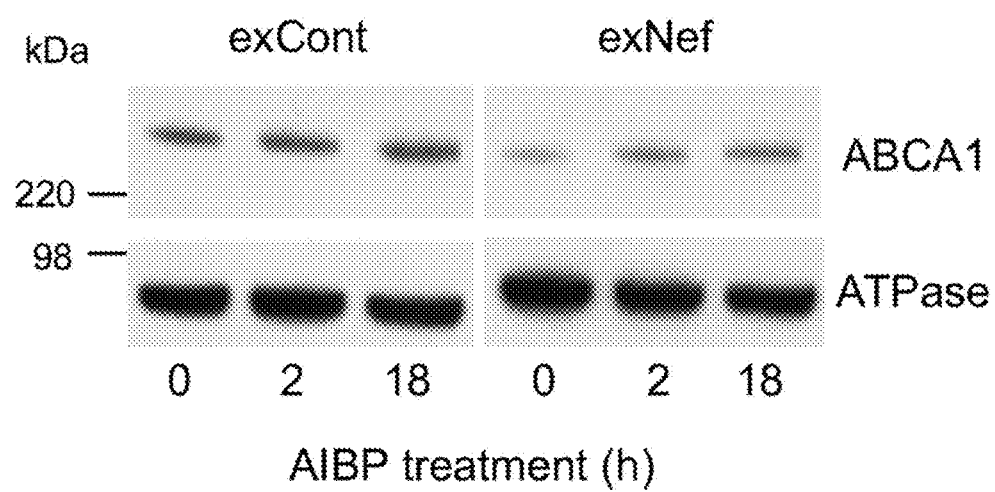
FIG. 4G illustrates an image of a Western blot showing data where HepG2 cells were treated for 48 h with exCont or exNef, and then incubated for 18 h in the presence or absence of AIBP (0.2 µg/ml), total ABCA1 and K, Na ATPase (loading control) as assayed by Western blotting (left panel), and images from 6 independent experiments were quantified by IMAGEJ™ (right panel), as further discussed in Example 1, below.

To investigate the anti-HIV effects of AIBP in the in vivo setting, we used humanized mice. Immunodeficient mice were reconstituted with human CD4+ memory T lymphocytes (Table 1). One group of hu-mice (animals #1-6) was injected intravenously with non-replicating adeno-associated viral vector expressing His-tagged AIBP. As a control, another group (animals #7-12) was injected with empty AAV. Two weeks after AAV injection, all hu-mice were infected with HIV-1 ADA using intraperitoneal injection. We used the R5 HIV-1 strain here to mimic human infections, which are transmitted almost exclusively with CCR5-tropic viruses (59). Mice were maintained for 9 weeks after HIV infection, after that period, mice were sacrificed and AIBP expression was measured by Western blotting of the liver tissue (direct detection of AIBP in blood is challenging, likely due to rapid binding of AIBP to cells (5, 7, 8)). The timeline of the experiment is presented in FIG. 4A. All hu-mice injected with AIBP-AAV expressed His-tagged AIBP in the liver (FIG. 4B). The AAV-DJ/8 vector used in this study has a mutation in the heparin binding domain, which lifts the liver restriction of AAV-DJ and expands its transduction to non-hepatic tissues (60). Detection of the His-tagged AIBP indicates that AAV-mediated expression was stable and continued throughout the duration of the experiment. Analysis of HIV-1 viral load revealed lower HIV replication in AIBP-expressing mice (FIG. 4C), and analysis by two-way ANOVA demonstrated that the difference between the groups was significant. One mouse (animal #5) in AAV-AIBP group did not get infected by HIV-1 at all, despite the fact that it was effectively reconstituted with human T cells (Table 1). No significant difference between the groups was found in the number of human CD4+ T cells (FIG. 4D). Our previous study demonstrated a reduction of ABCA1 abundance in livers of SIV-infected monkeys (18). In HIV-infected animals expressing AIBP the abundance of ABCA1 was significantly higher (p=0.0491) than in HIV-infected mice exposed to empty AAV (FIG. 4E, F). Of note, similar to observation in SIV-infected macaques (18), suppression of ABCA1 in HIV-infected untreated mice was not complete, likely due to compensatory upregulation of ABCA1 mRNA expression (13). To further evaluate this activity of AIBP, we tested whether it can protect human hepatocytes from ABCA1 downregulation induced by exNef. Human HepG2 cells were treated with exCont or exNef (equalized by protein content) for 18 h in the presence or absence of recombinant AIBP (0.2 µg/ml) and apoA-I (50 µg/ml), and ABCA1 and K,Na ATPase (loading control) were assessed by Western blotting (FIG. 4G, left panel). Bands were quantified by ImageJ and the ABCA1/ATPase ratio was calculated for 5 independent experiments (FIG. 4G, right panel). This analysis confirmed that exNef significantly downregulated ABCA1 (p=0.0493), and AIBP reversed this effect (p=0.0171). Taken together, these results indicate that AIBP not only reduces HIV replication, but also protects host cells from indirect effects of HIV infection, which are likely mediated by the factors, including exNef, released from HIV-infected cells (18).

HLA-B Genotype Influences the Anti-HIV Activity of AIBP

Figure 5A:
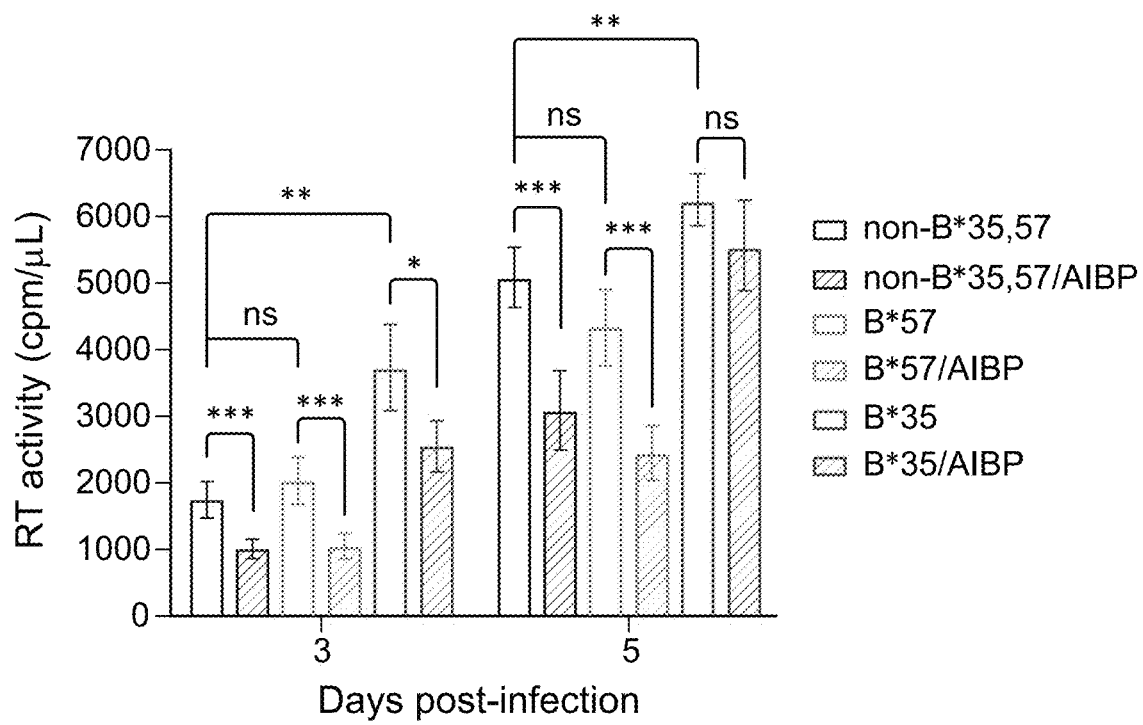
FIG. 5A-G illustrate data showing that anti-HIV effect of AIBP is reduced in cells from HLA-B*35 donors.
Figure 5B:
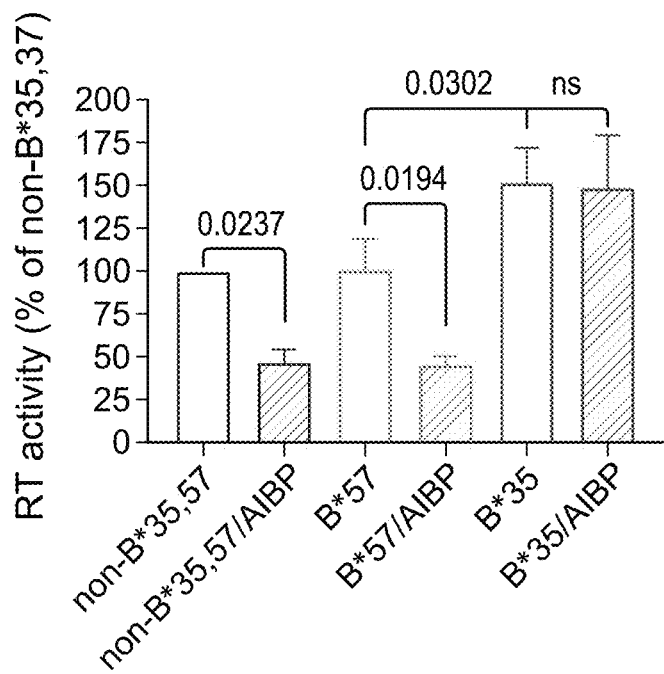
Figure 5C:
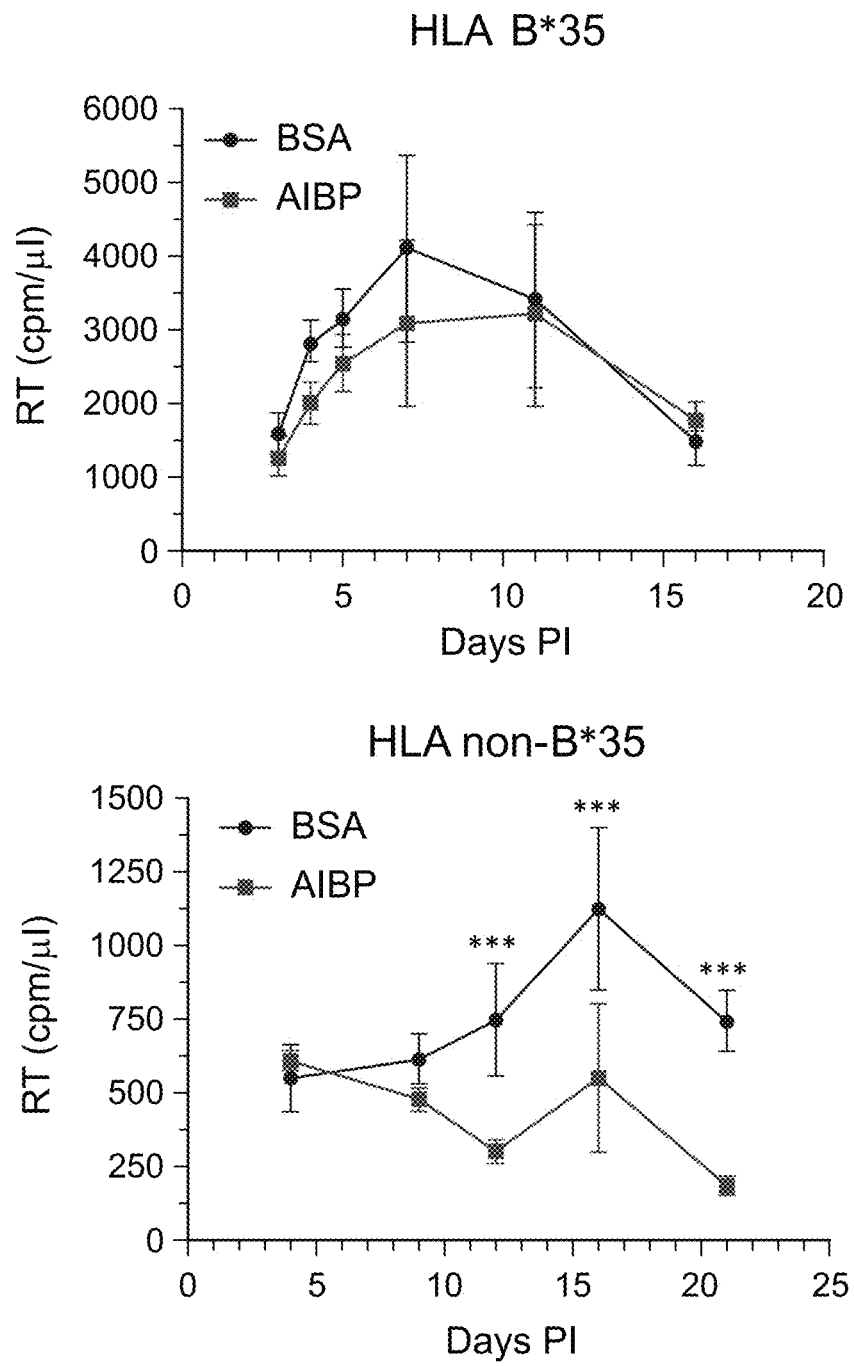
Figure 5D:
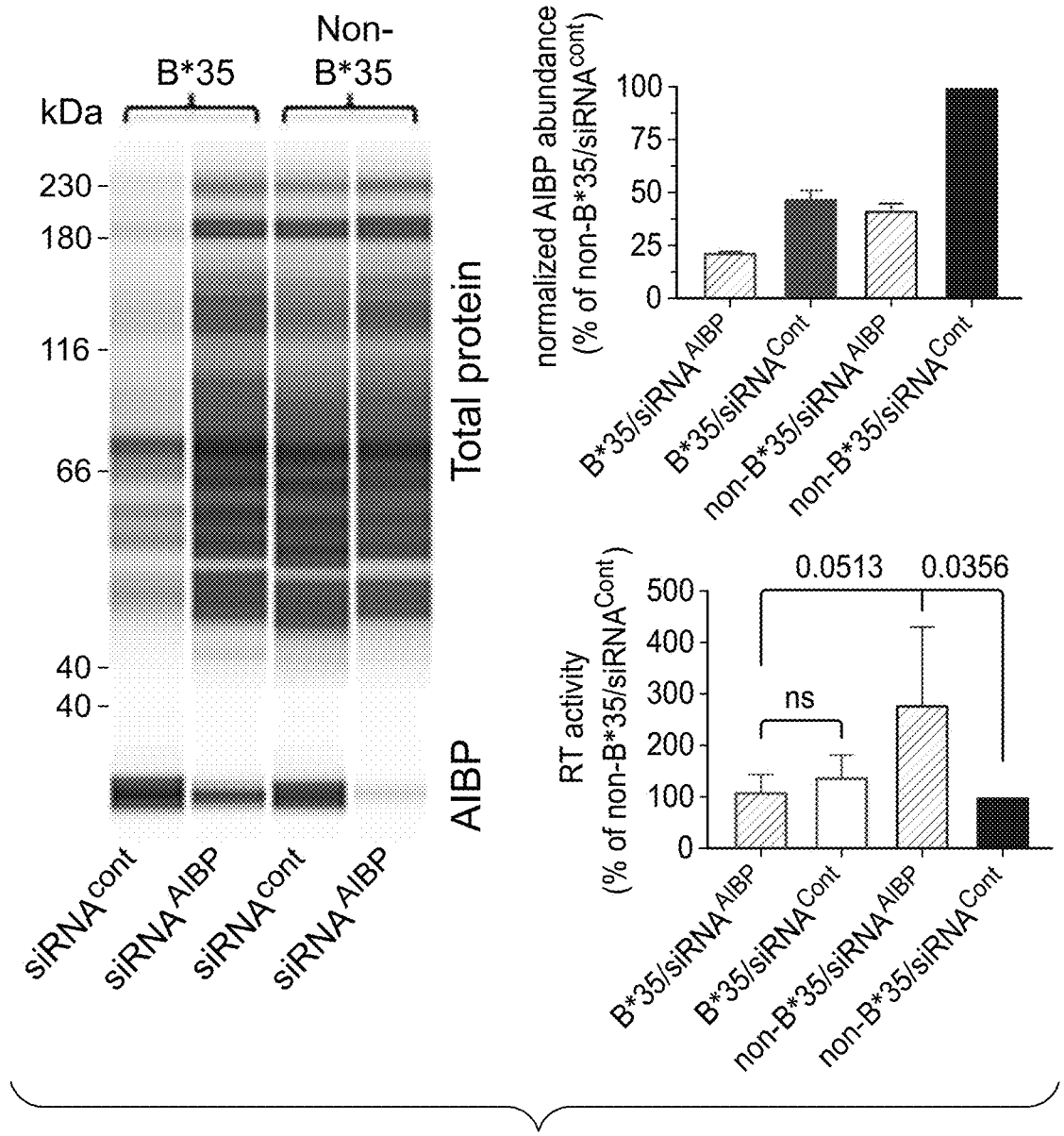
Figure 5E:
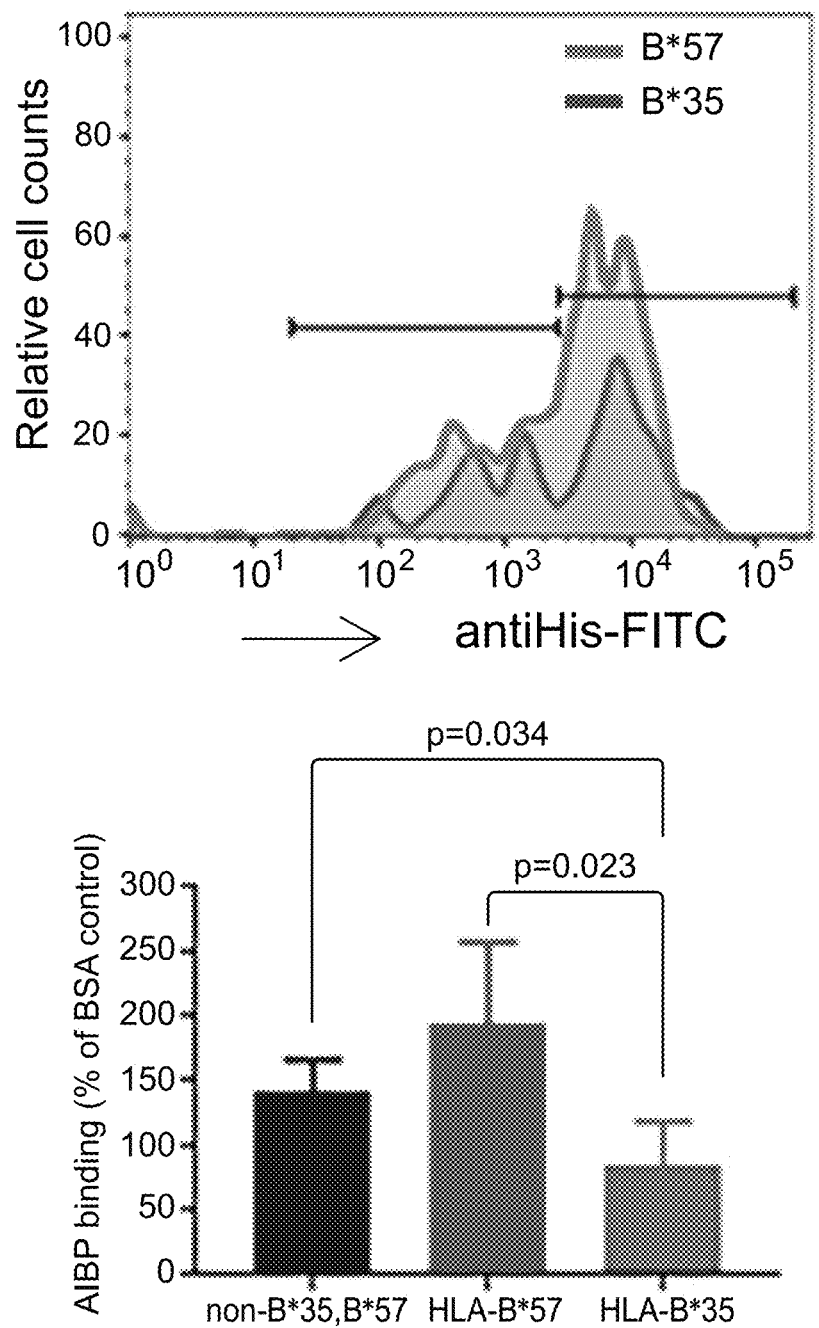
Figure 5F:
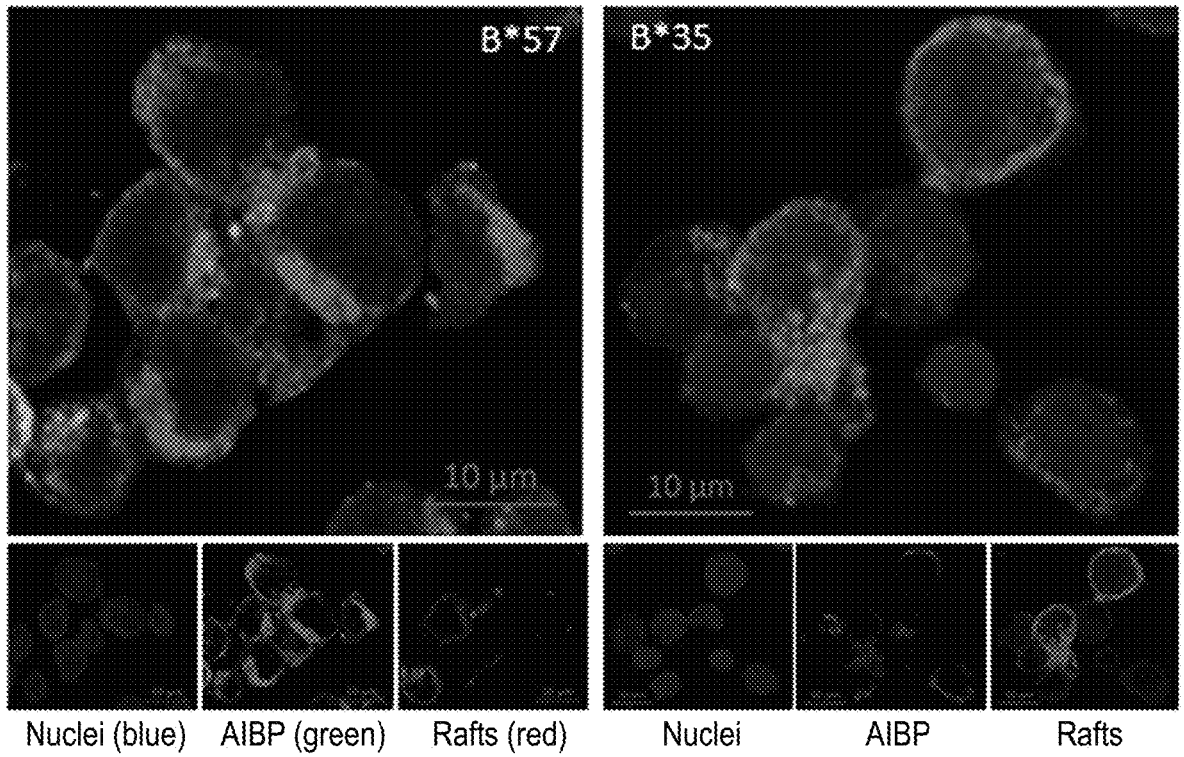
Figure 5G:
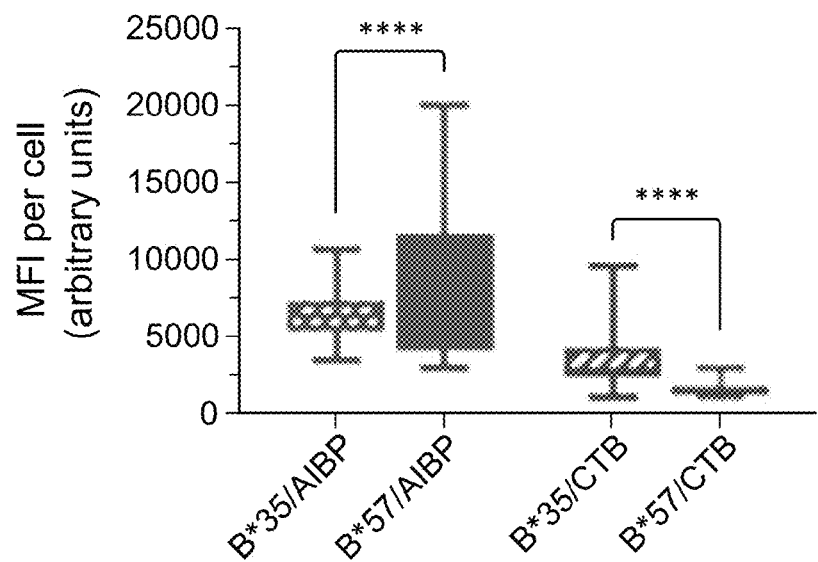

The impact of host genetic variation on susceptibility to HIV infection and progression of the disease has been well established (61). In particular, specific HLA alleles have been found to be the primary determinants of the rate of progression to AIDS (62-65). For example, the HLA-B*35 genotype has been associated with rapid progression of the disease (62), whereas the HLA-B*57 allele has been consistently associated with slower disease progression (66). This has been explained by differences between the alleles in antigenic peptide presentation (67). However, given association of MHC-I molecules with lipid rafts (68), which are regulated by AIBP, we hypothesized that HLA-B genotype may also influence HIV replication by altering the effect of AIBP. We infected PBMCs isolated from 3 donors with HLA-B*35, HLA-B*57, and non-B*35,57 genotypes with HIV-1 LAI and followed virus replication in the presence or absence of recombinant AIBP. As shown in FIG. 5A, the suppressive effect of AIBP on HIV replication was significantly smaller in cells from HLA-B*35 donors on day 3 post-infection, and completely disappeared on day 5 p.i, whereas in two other donors with non-B*35 genotype AIBP-mediated suppression was still highly significant (p<0.001). No significant differences in anti-HIV activity of AIBP were found between B*57 and non-B*35,57 donors, suggesting that relative resistance of HLA-B*57-positive people to HIV disease progression is not due to AIBP sensitivity. Importantly, HIV-1 replication in cells from HLA-B*35 donor was significantly higher than in cells from B*57 and non-B*35, 57 donors (FIG. 5A). These results were confirmed using cells from 3 donors with each of B*35, B*57, and non-B*35,57 genotypes (FIG. 5B). On day 5 post-infection, AIBP significantly downregulated HIV-1 replication in donors with non-B*35 genotype, but not in HLA-B*35 donors. HIV-1 replication in cells from B*35 donors was higher than in cells with non-B*35 genotype, although the difference was relatively small (p=0.0302). No significant differences were observed between cells with HLA-B*57 and non-B*35,57 genotypes in HIV-1 replication or susceptibility to AIBP suppression (FIG. 5B). We further extended this observation to the T/F HIV-1 strain pCH185.c/K3016 (30). Again, recombinant AIBP reduced replication of the T/F virus in cells from non-B*35 donor, but not in cells from HLA-B*35 donor (FIG. 5C). Strikingly, knockdown of endogenous AIBP significantly increased HIV-1 LAI replication in cells from non-B*35 donor, but did not affect replication in HLA-B*35 cells (FIG. 5D, bottom right panel). We next measured the binding of recombinant AIBP to cells with different HLA-B genotype. AIBP binding to cells from HLA-B*35 donors was significantly lower compared to binding to cells from HLA-B*57 donors or donors with non-B*35,57 genotype (FIGS. 5E and FIG. S6). Again, difference between B*57 and non-B*35,57 donors was not significant (FIG. 5E, bottom panel). The difference in AIBP binding is illustrated in FIG. 5F, where cells from HLA-B*35 and HLA-B*57 donors are shown, and is quantified in FIG. 5G. Cell-bound His-tagged AIBP was brightly stained on cells from HLA-B*57 donor, and much less on cells from HLA-B*35 donor (FIG. 5F). The opposite was observed with CTB staining which reflects abundance of lipid rafts: rafts were much more brightly stained on HLA-B*35 than on B*57 cells, consistent with the proposed raft-reducing activity of AIBP. Quantitation of AIBP binding demonstrated significantly reduced binding to HLA-B*35 cells, whereas lipid raft staining was significantly higher on HLA-B*35 than on HLA-B*57 cells (FIG. 5G). These results indicate that HLA-B*35 genotype impairs AIBP binding to target cells and makes cells insensitive to the anti-HIV activity of AIBP, both endogenously produced or added exogenously.

Discussion

Accumulating evidence suggests a protective, and possibly a therapeutic, role of AIBP in human diseases associated with inflammation and impairment of cholesterol metabolism, in particular in atherosclerosis (6, 69). The main finding of this study is that AIBP also exerts an anti-HIV activity. Mechanistically, AIBP decreased the abundance of lipid rafts on activated cells, reducing virus-cell fusion. Importantly, no change in the abundance of lipid rafts or fusion was observed after incubation of non-activated cells with AIBP. This result is consistent with previously reported findings and suggests that AIBP specifically targets lipid rafts on cells subjected to an inflammatory or infectious agent or factors produced by infected cells (6, 7). One such 'activating' factor could be Nef-containing exosomes (ex-Nef). Indeed, AIBP reversed the effect of exNef on the abundance of lipid rafts on MDM. Our results suggest that exNef, which are produced by HIV-infected cells even in the presence of suppressive ART (70, 71), may enhance HIV-associated pathology by manipulating lipid rafts on uninfected cells. Nef is considered the key pathogenic factor of HIV due to its profound effects on viral replication, immune system, and multiple tissues (72-74). Previous studies attributed pathogenic activity of Nef to its ability to suppress CTL response by downregulating MHW I (75), and to stimulate viral spread by downregulating CD4 (76) and SERINC3 and 5 in infected cells (77, 78). Our findings suggest another, previously unappreciated, activity of Nef: Nef exosomes increase the abundance of lipid rafts on macrophages stimulating HIV infection (this report) and potentiating lipid raft-dependent inflammatory responses (52).

Our finding that AIBP inhibits fusion of the Nef-positive virus, which does not incorporate SERINC (77, 78), but does not inhibit fusion of Nef-deficient virus, which incorporates SERINC, suggests that fusion of SERINC-positive HIV occurs via lipid rafts that are insensitive to AIBP. One suggested mechanism of SERINC5 anti-HIV activity is that it forms large oligomers, which harden the viral membrane, restrict lipid diffusion, slow the folding of the envelope for fusion, and decrease virus-cell fusion (79, 80). The slowed fusion of such virus may proceed via 'normal' lipid rafts, not affected by AIBP. However, treatment of MDM with exNef induces formation of 'pathological' rafts, increases fusion with Nef-deficient HIV, and makes fusion susceptible to AIBP inhibition. Interestingly, pre-treatment of macrophages with exNef, while increasing abundance of lipid rafts, did not increase MDM fusion with wild-type HIV, suggesting that Nef delivered by either virions or by virion-contaminating exosomes is sufficient to ensure maximal fusion. This effect of Nef on fusion contradicts conclusion of previous reports that Nef does not alter fusion (57, 58). The difference with those studies is that the effects reported here were observed with MDM, whereas cited above reports used T cell lines or PHA-activated CD4+ T cells. Our analysis demonstrated that activated T cells have high levels of lipid rafts (FIG. 2A) that were not much changed by adding exNef, and, relative to MDM, much higher levels of endogenous AIBP expression (FIG. 1H) that may mask the effect of Nef. It remains to be tested whether exNef increases the abundance of lipid rafts on non-activated T cells, and whether this increases fusion with HIV.

In this study, we used a simplified model of humanized mice, immunodeficient mice reconstituted with human memory CD4+ T lymphocytes. This model allows to avoid graft versus host reaction (81) and maintains HIV replication for several months. Lack of human myeloid cells in this model is a limitation, especially in view of the role of these cells in HIV infection (82), and their sensitivity, relative to CD4+ T lymphocytes, to agents targeting cholesterol efflux (17, 27, 83). In vitro experiments with MDM performed in this study demonstrated that AIBP potently inhibits HIV replication in these cells, so we expect that AIBP will exert an even more pronounced anti-HIV activity in a model containing a full range of HIV-susceptible cells. AAV-delivered AIBP protein was detected in liver lysates (FIG. 4B), but its levels in plasma were undetectable despite the fact that the AIBP construct was designed to produce a secreted protein. This agrees with the report that AIBP was undetectable in normal human plasma (1). In addition, AIBP was not detected in any HDL proteomic studies despite its documented binding to apoA-I and HDL (1, 5). This can be explained by the fact that secreted AIBP binds to inflammatory cells (7, 8) and to activated PBLs (FIG. 5), leading to rapid clearance from plasma of the AIBP secreted from liver and other tissues in AAV-AIBP infected mice.

The finding that HLA-B*35 genotype associated with reduced AIBP binding and decreased anti-HIV activity was serendipitous. Given that HLA association with lipid rafts has been previously suggested (68), it is likely that HLA-B*35-dependent modifications of lipid raft structure/composition may influence AIBP binding to cells, modulating its ability to reduce lipid rafts and inhibit virus-cell fusion. This may be a contributing factor to the known association of HLA-B*35 genotype with fast disease progression. This conclusion is supported by our finding that AIBP silencing did not affect HIV-1 replication in the cells with HLA-B*35 genotype, while significantly increasing virus replication in cells with other HLA genotypes. The HLA-B*35 genotype appears to stand out, as we did not find significant differences in AIBP binding or anti-HIV activity between cells of other genotypes tested in this study. It remains to be established whether other HLA genotypes associated with HIV susceptibility or control influence AIBP binding, before more elaborate mechanistic studies of HLA-mediated changes in lipid rafts are initiated. The mechanism of anti-HIV activity of AIBP is likely to involve its ability to reduce the abundance of lipid rafts. This conclusion is based on well-established capacity of AIBP to disrupt lipid rafts (1, 5, 7, 8), and the role of rafts in HIV fusion (43); concurrent effect of AIBP on rafts and HIV fusion was demonstrated in several independent experimental systems throughout this study. The mechanism behind AIBP-mediated disruption of lipid rats was not investigated in this study, but previous reports suggested that AIBP stimulates cholesterol efflux depleting rafts of cholesterol (1, 5). It may also stabilize ABCA1 (9), providing additional capacity for cholesterol efflux.

Results of this study demonstrate that AIBP is an innate anti-HIV restriction factor. Although pathways regulating endogenous AIBP expression and secretion are not well understood, existing evidence points to spatiotemporal and/or regulated pattern of AIBP secretion (1, 5, 8). Described in this study low sensitivity to AIBP-mediated anti-HIV activity of cells from HLA-B*35 donors, which are susceptible to fast progression of HIV disease, suggests the role of AIBP in controlling natural HIV infection. In this work we sought to augment the benefit of an innate AIBP protective mechanism by delivering recombinant protein or AAV-expressed AIBP to target activated host cells and make them less susceptible to HIV infection. The anti-HIV effect of such treatment, while significant, was relatively small when compared to the effects of anti-retroviral drugs (for example T-20). One potential reason is that the effect was measured on the background of endogenous AIBP. PBLs are hard to transfect and the silencing approach we used produced only a 30-50% downregulation of endogenous AIBP. Future studies with engineered AIBP-deficient cells are likely to produce more impressive results. Given that lipid rafts are used by many pathogens as an entry platform (84), AIBP may also protect against infection by other viruses and microbes. Overall, this study reveals a novel innate factor that inhibits HIV infection by targeting lipid rafts.

TABLE 1

Reconstitution of mice with human CD4+memory T cells.

| Mouse ID | Human CD4 + memory T cells (cells/μl) |
|---|---|
| 1 | 1117 |
| 2 | 990 |
| 3 | 1086 |
| 4 | 1024 |
| 5 | 6265 |
| 6 | 1342 |
| 7 | 790 |
| 8 | 611 |
| 9 | 1122 |
| 10 | 1458 |
| 11 | 235 |
| 12 | 2923 |

Cells were analyzed by flow 2 weeks after reconstitution.

Figure Legends

FIG. 1. AIBP Inhibits HIV-1 Replication.

A—Quadruplicate wells of monocyte-derived macrophages (MDM) were infected with HIV-1$_{ADA}$, and virus production was measured on day 12 post infection by RT activity in culture supernatant. Bars show mean±SD. Statistical analysis was done by Dunnett's multiple comparison test, p=0.0013, **p<0.0001. B—PHA-activated PBLs or MDM from one representative donor were infected in triplicate wells with HIV-1$_{LAI}$ or HIV-1$_{ADA}$ strains, respectively, cultured in the presence or absence of recombinant AIBP (0.2 μg/ml), and HIV replication was followed by measuring p24 in culture supernatants. Holm-Sidak adjusted p values from multiple comparison test are shown. C—Experiment was performed as in B with PHA-activated PBL from 6 donors and MDM from 4 donors. Virus replication was followed by RT activity. Results are presented for each donor at the peak of infection as percent of RT activity in AIBP-negative (control) culture. Holm-Sidak adjusted p values are shown. D—PHA-activated PBLs were infected with T/F strain pCH185.c/K3016 and cultured in the presence or absence of 0.2 μg/ml recombinant AIBP (recombinant AFP was used as control). Virus replication was followed by RT activity. Results show mean±SD (n=4). Holm-Sidak adjusted p value is shown. E. PHA-activated PBLs and MDMs were exposed to indicated concentrations of recombinant AIBP for 3 days, and cytotoxic effect of AIBP was measured by MTT assay and presented as percent of metabolic activity of AIBP-negative (control) cultures. Bars show mean±SD (n=4). F—PHA-activated PBLs were treated with AIBP as in panel C and percentage of live cells was measured by flow cytometry using LIVE/DEAD Fixable Aqua kit (Invitrogen). Bars show mean±SD (n=3). G—PHA-activated PBLs were treated with AIBP-targeting or control Accell siRNA for 72 h. AIBP abundance was measured by PROTEINSIMPLE™ Western blotting (left panel), normalized against total protein, and presented relative to cells treated with siRNA$^{Cont}$ (right top panel). Cells were infected in 5 wells with HIV-1LAI, cultured for 3 days, and HIV production was measured by RT activity in culture supernatant (right bottom panel). P value was calculated by unpaired t test (n=5). H—PBLs and MDMs from the same donor were analyzed in triplicate for AIBP by PROTEINSIMPLE™ Western blotting (left panel). Relative abundance of AIBP normalized against total protein is shown in the right panel. P value was calculated by unpaired t test (n=3).

FIG. 2. AIBP Regulates Abundance of Lipid Rafts

A—PBLs from a representative donor were stimulated or not with PHA, stained with fluorescently labeled cholera toxin B subunit, and analyzed by flow cytometry. B—Representative analysis of vesicle size and concentration in exosome samples from supernatants of HEK293 T cells transfected with Nef (exNef) or empty vector (exCont) by Nanosight (top panels). Mean±SEM of vesicle size (nm) and vesicle concentration (particles/mL) are shown in the bottom panel. C—Vesicles were analyzed by Western blotting for the exosomal marker Alix, tetraspanin CD63, cytosolic marker HSP70, and Nef. D—MDM from a representative donor were treated with exNef or exCont in the presence of AIBP or BSA, and lipid rafts were analyzed as in A. E—Lipid rafts were analyzed as in A and D. Results are presented for experiments with cells from 4 different donors. Left panel: *p=0.0088, unpaired t-test with Holm-Sidak adjustment, relative to activated PBL treated with BSA. Right panel: *p=0.0038 relative to cells treated with exCont and BSA, #p=0.0129 relative to MDM treated with exNef and BSA, ordinary one-way ANOVA with Tukey adjustment for multiple comparisons.

FIG. 3. AIBP Inhibits HIV Fusion with Target Cells.

A—PBLs from a representative donor were stimulated or not with PHA, stained with fluorescently labeled cholera toxin B subunit, and analyzed by flow cytometry. B—Representative analysis of vesicle size and concentration in exosome samples from supernatants of HEK293 T cells transfected with Nef (exNef) or empty vector (exCont) by NANOSIGHT™ (top panels). Mean±SEM of vesicle size (nm) and vesicle concentration (particles/mL) are shown in the bottom panel. C—Vesicles were analyzed by Western blotting for the exosomal marker Alix, tetraspanin CD63, cytosolic marker HSP70, and Nef. D—MDM from a representative donor were treated with exNef or exCont in the presence of AIBP or BSA, and lipid rafts were analyzed as in A. E—Lipid rafts were analyzed as in A and D. Results are presented for experiments with cells from 4 different donors. Left panel: *p=0.0088, unpaired t-test with Holm-Sidak adjustment, relative to activated PBL treated with BSA. Right panel: * p=0.0038 relative to cells treated with exCont and BSA, #p=0.0129 relative to MDM treated with exNef and BSA, ordinary one-way ANOVA with Tukey adjustment for multiple comparisons.

FIG. 4. AIBP Reduces HIV Load and Reverses ABCA1 Downregulation in Liver Cells

A—Timeline of the in vivo experiment. B—Western blot analysis of livers from hu-mice infected with AAV and AAV-AIBP. C—Viral load analysis of hu-mice. *–p=0.0238 by a 2-way ANOVA. D—Analysis of human CD4+ cells in hu-mice. No significant differences detected by 2-way ANOVA. E—Western blot for AIBP and GAPDH of livers from hu-mice infected with HIV-1 and AAV-AIBP (#1, 2, 3), and hu-mice infected with HIV-1 and empty AAV (#7, 8, 9). F—Quantitation of the blot in panel E. P value was calculated by unpaired t-test. G—HepG2 cells were treated for 48 h with exCont or exNef, and then incubated for 18 h in the presence or absence of AIBP (0.2 µg/ml). Total ABCA1 and K,Na ATPase (loading control) were assayed by Western blotting (left panel), and images from 6 independent experiments were quantified by ImageJ (right panel). Results present mean±SD. Significance was calculated by 1-way ANOVA with Tukey multiple comparisons adjustment.

FIG. 5. Anti-HIV effect of AIBP is reduced in cells from HLA-B*35 donors

A—PHA-activated PBMCs from donors with HLA-B*35, HLA-B*57, and non-B*35, B*57 genotypes were infected with HIV-1$_{LAI}$ and incubated in the presence or absence of recombinant AIBP. Virus replication was followed by RT activity. Results are presented for donors B*35/55 (B*35), B*51/57 (B*57), and B*27/38 (non-B*35, B*57). Results are presented as mean±SD of 5 replicates, *–p=0.01, –p<0.01, *–p<0.001 by multiple comparisons tests with Holm adjustment. B-Experiment was performed as in A with cells from 3 donors of each genotype. Results (mean±SD) are presented relative to cells from non-B* 35,57 donor (taken as 100%) at the time point corresponding to the peak of infection (day 5 p.i.). P values were calculated by ordinary one-way ANOVA with Tukey multiple comparisons adjustment. C—PHA-activated PBMCs from HLA-B*35 or non-B*35 donors were infected with T/F strain pCH185.c/K3016 and cultured in the presence or absence of 0.2 µg/ml recombinant AIBP or BSA. Virus replication was followed by RT activity. Results show mean±SD (n=4). Significance was calculated by multiple t-tests with Holm-Sidak correction for multiple comparisons. *** p<0.001. D—PHA-activated PBMCs from HLA-B*35 and non-B*35 donors were treated with AIBP-targeting (siRNA$^{AIBP}$) or control (siRNA$^{Cont}$) Accell siRNA. AIBP abundance was measured by PROTEINSIMPLE™ Western blotting (left panel), normalized against total protein, and presented relative to non-B*35 cells treated with siRNA$^{Cont}$ (right top panel). Cells were infected with HIV-1 LAI, and RT activity in culture supernatant was measured on day 4 post infection (right bottom panel). Results show mean±SD of 4 replicates. Ordinary one-way ANOVA with Tukey adjustment for multiple comparisons was used to calculate p values. E—Binding of recombinant AIBP to cells with different HLA-B genotype was analyzed by flow cytometry using anti-His antibody (top panel). Bottom panel—Quantitation of AIBP binding to cells from 4 different donors each of genotypes B*35 and non-B*35,B*57 and 3 donors of B*57 genotype. P values were calculated by multiple t tests, with post-hoc Holm adjustment for multiple comparisons. F—Binding of recombinant AIBP to cells with HLA-B*35 and HLA-B*57 genotype was analyzed by fluorescent microscopy using Alexa Fluor®555 conjugated CTB for lipid rafts (red), FITC-conjugated anti-His antibody for AIBP (green), and DAPI for nuclei (blue). G—Quantification of WI on 108 cells with HLA-B*35 and 159—with HLA-B*57 genotype using VOLOCITY™ software. **** p<0.0001 calculated by ANOVA with Bonferroni correction for multiple comparisons.

Supplemental Figures

Figure 6A:
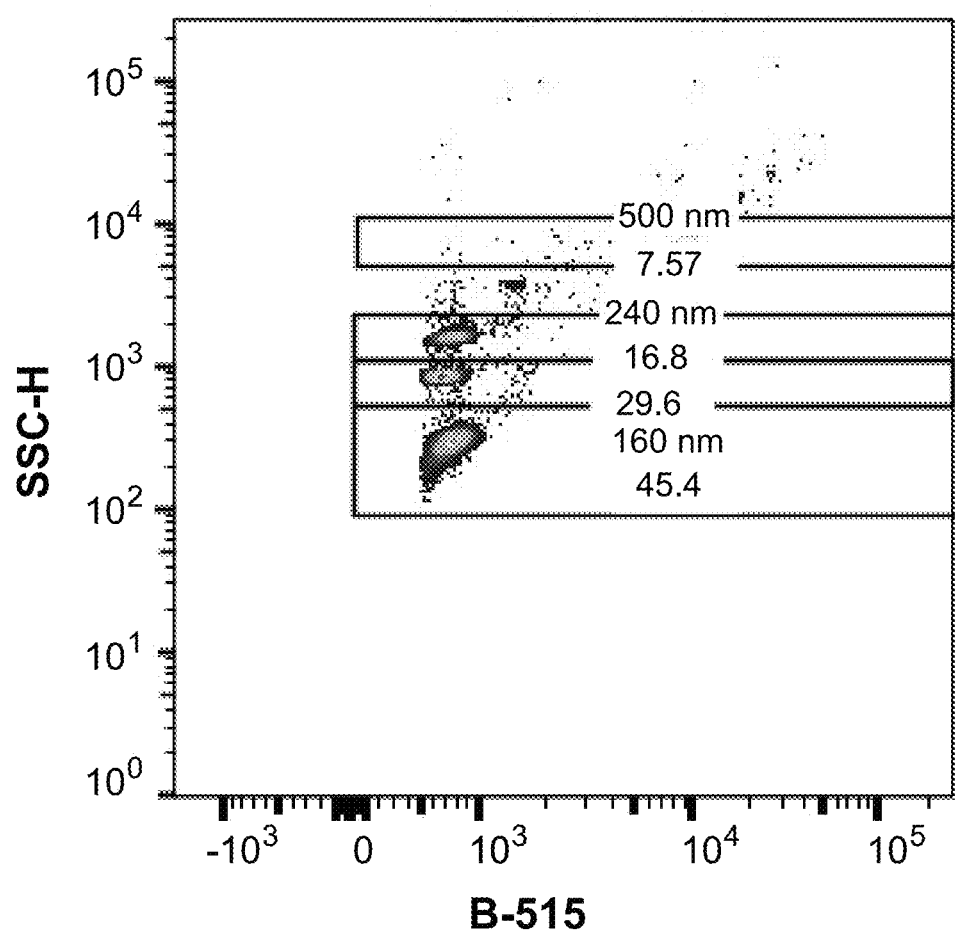
FIG. 6A-B illustrates data visualization of EVs with flow cytometry.
Figure 6B:
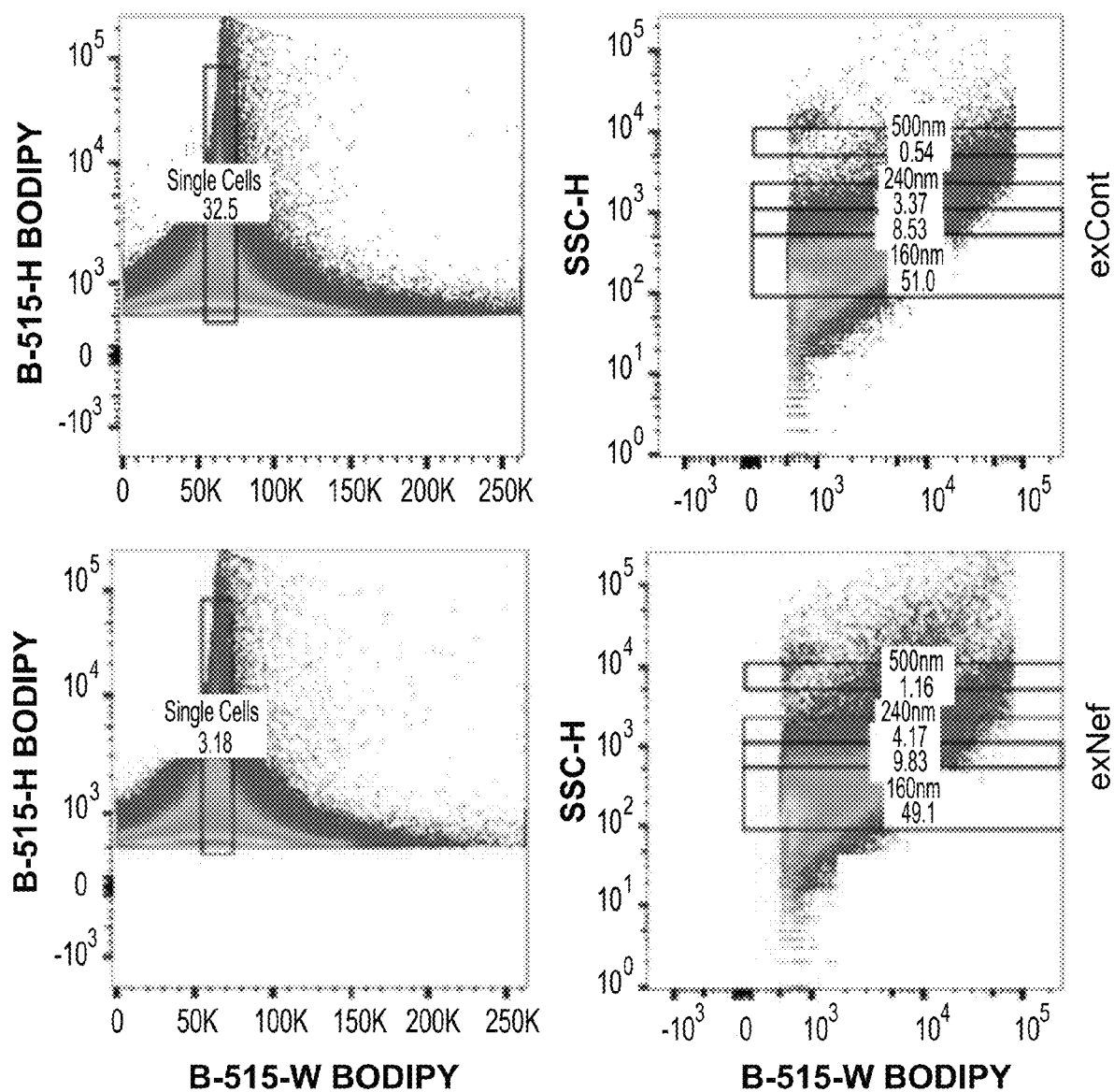

FIG. 6, or S1. Visualization of EVs with flow cytometry. A—Defining sizing gates with MEGAMIX™ beads. Fluorescent MEGAMIX™ plus SSC beads were used according to manufacturer (Cosmo Bio, Calif.). B—EV visualization with flow cytometry. exCont and exNef EVs were labeled with the lipophilic tracer BODIPY (the technical common name of 4,4-difluoro-4-bora-3a, 4a-diaza-s-indacene) (INVITROGEN™, Life Technologies, Calif.) and visualized with a LSRII (BECTON DICKINSON™) as BODIPY-positive events thresholding on BODIPY fluorescence. Left column: Gating strategy for flow analysis of BODIPY-labeled EVs isolated from mock-(upper panel) or Nef-transfected (lower panel) HEK293T cells. A singlet gate was defined by plotting fluorescence height versus fluorescence width. The gate excludes events with a high width and high height that represent aggregates. Right column: EV sizing as defined by MEGAMIX™ plus SSC beads gates (A). Results represent one of two similar experiments. On each plot, the fraction of total events in their respective gates is shown.

Figure 7:
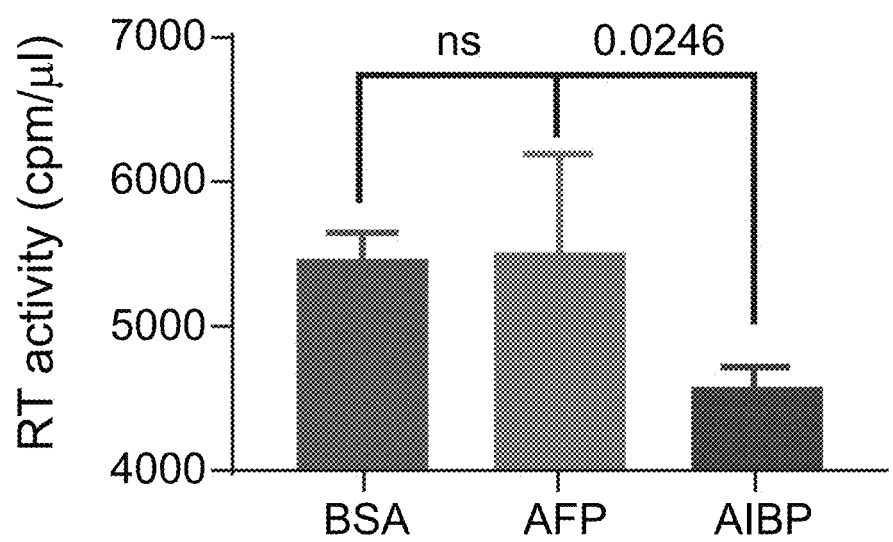
FIG. 7 graphically illustrates data showing that AIBP inhibits HIV-1 replication, where PHA-activated PBMCs were infected in quadruplicate wells with HIV-1 LAI and cultured for 5 days in the presence of 0.2 µg/ml of BSA, baculovirus-expressed alpha-fetoprotein (AFP), or baculovirus-expressed AIBP, and virus production was measured by RT activity in culture supernatant, as further discussed in Example 1, below.

FIG. 7, or S2. AIBP inhibits HIV-1 replication. PHA-activated PBMCs were infected in quadruplicate wells with HIV-1 LAI and cultured for 5 days in the presence of 0.2 µg/ml of BSA, baculovirus-expressed alpha-fetoprotein (AFP), or baculovirus-expressed AIBP. Virus production was measured by RT activity in culture supernatant. Results are presented as mean±SD, p values were calculated by ordinary one-way ANOVA with Tukey correction for multiple comparisons.

Figures 8A, 8B, 8C:
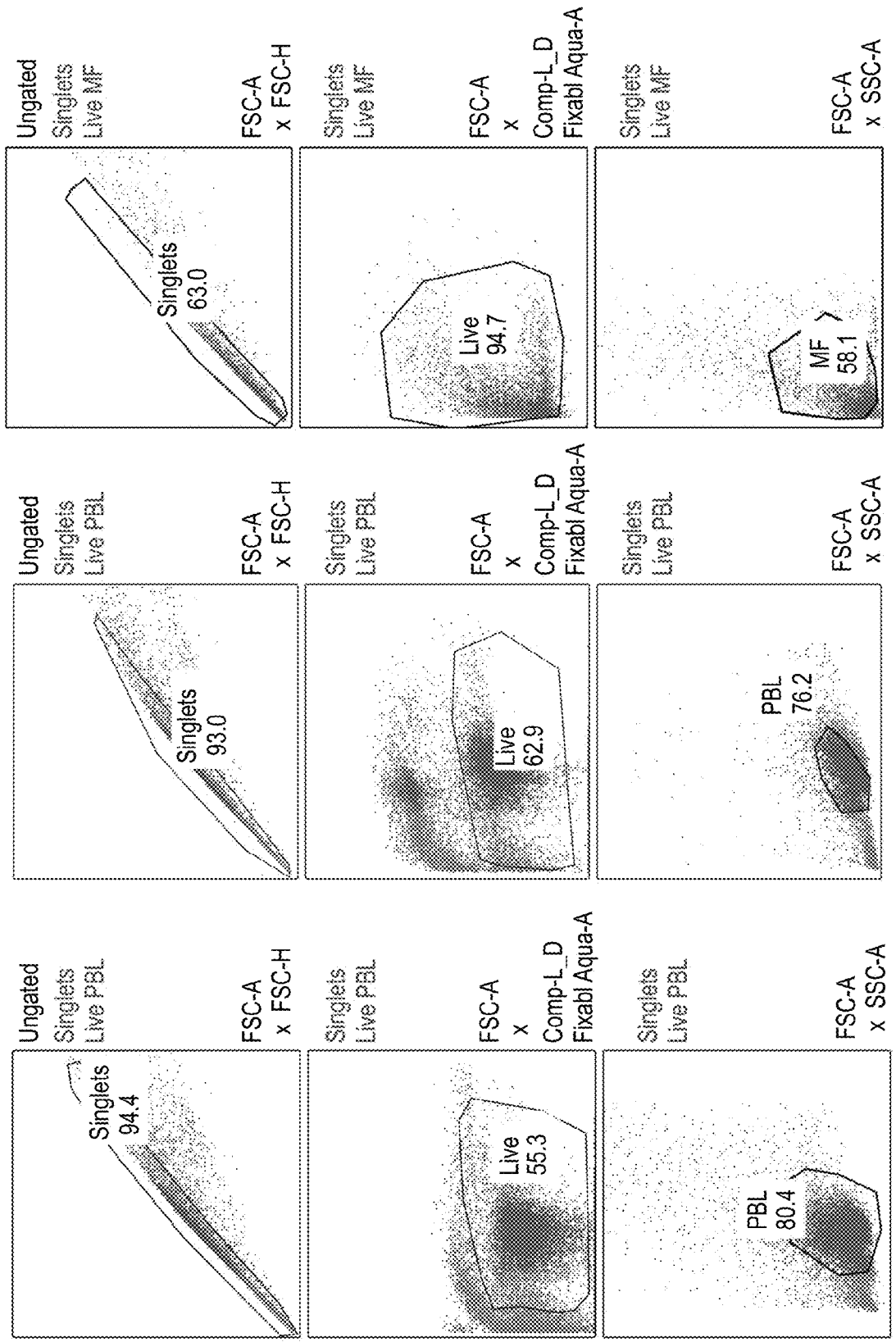
FIG. 8A-C illustrate flow cytometry data showing the gating strategy for FIG. 2.

FIG. 8, or S3. Gating strategy for FIG. 2. A—gating for unactivated PBL (FIG. 2A); B—gating for activated PBL (FIG. 2A); C—gating for MDM (FIG. 2C).

Figures 9A, 9B, 9C:
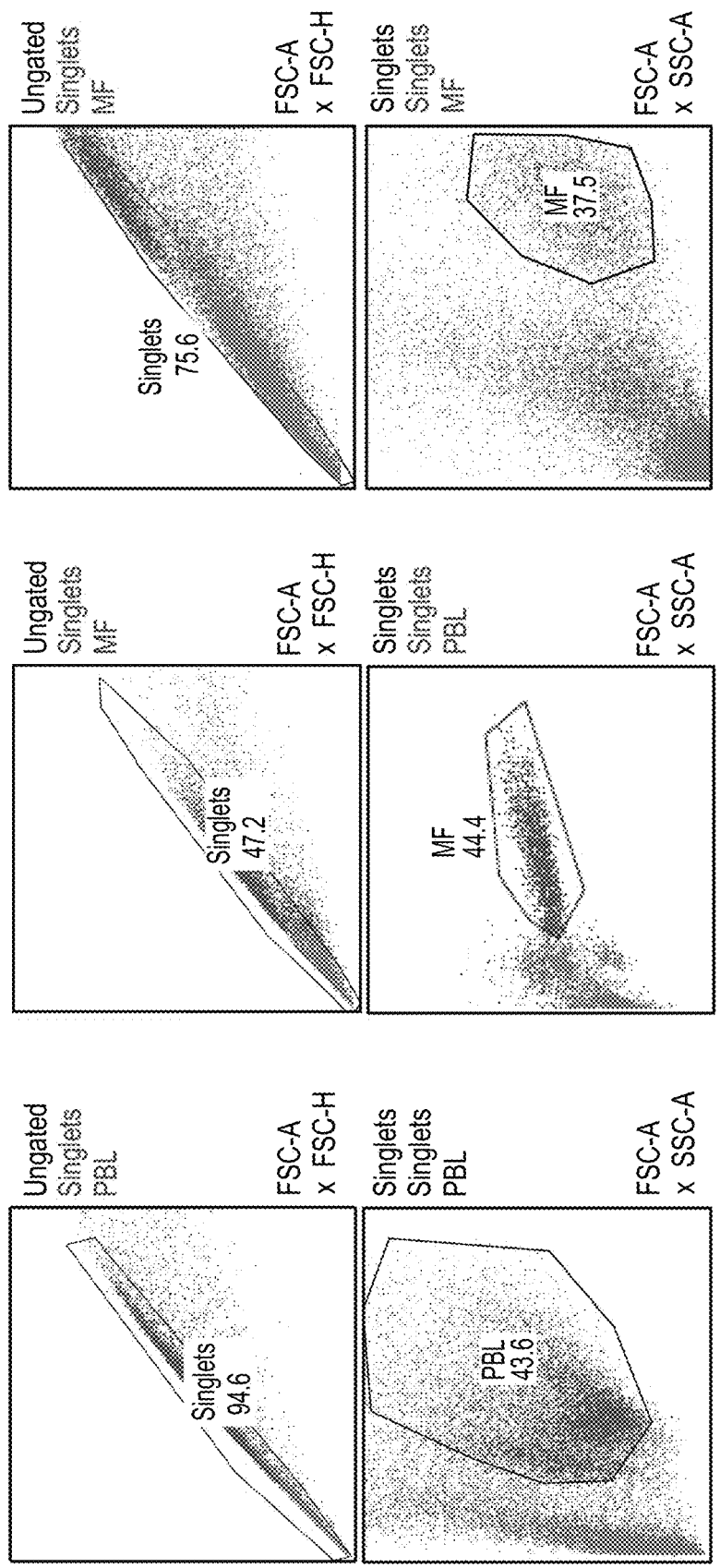
FIG. 9A-C illustrate flow cytometry data showing the gating strategy for FIG. 3.

FIG. 9, or S4. Gating strategy for FIG. 3. A—gating for PBL (FIG. 3A); B—gating for MDM (FIG. 3C); C—gating for MDM (FIG. 3F).

Figure 10A:
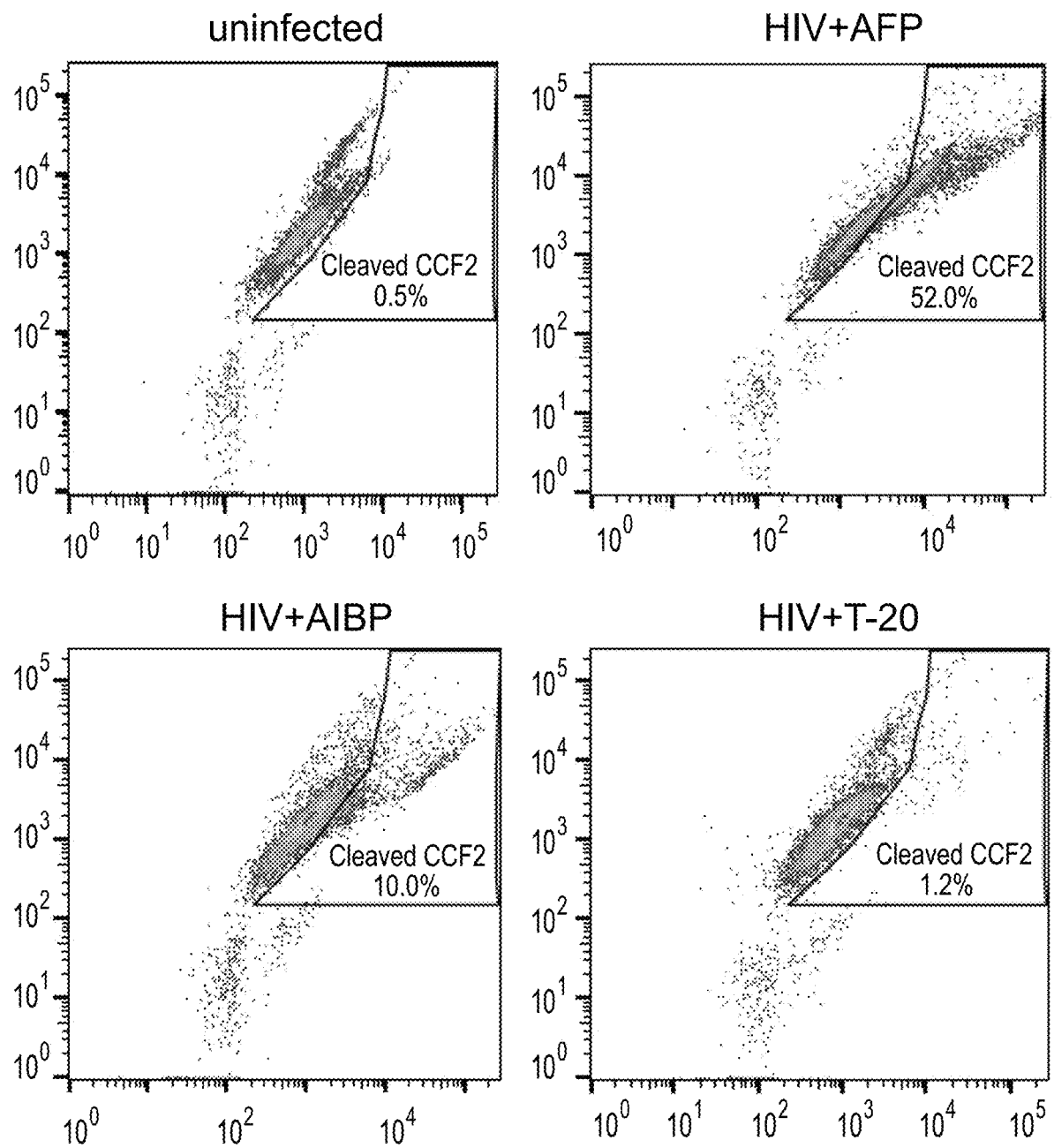
FIG. 10A-C illustrate data for the analysis of HIV fusion with MDM.
Figure 10B:
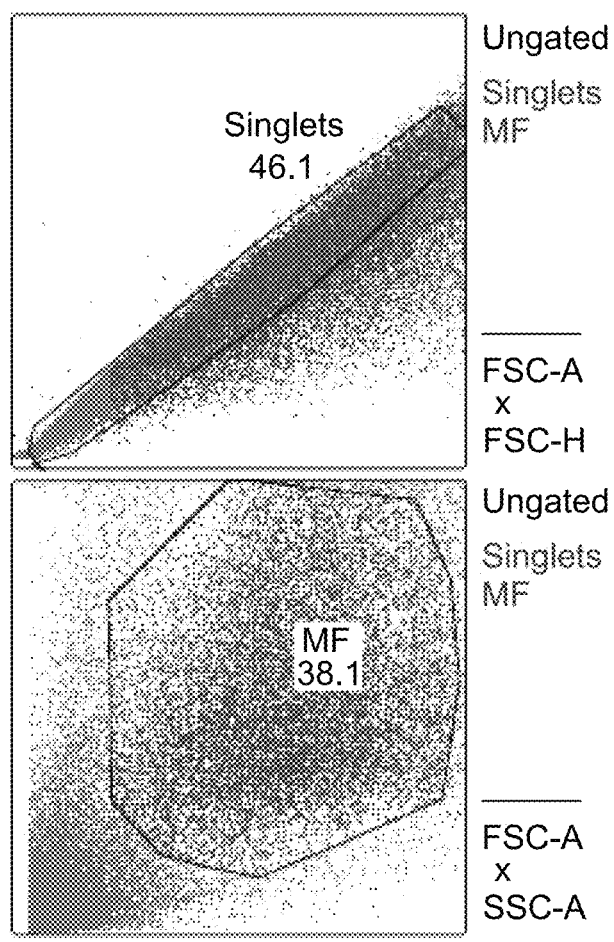
Figure 10C:
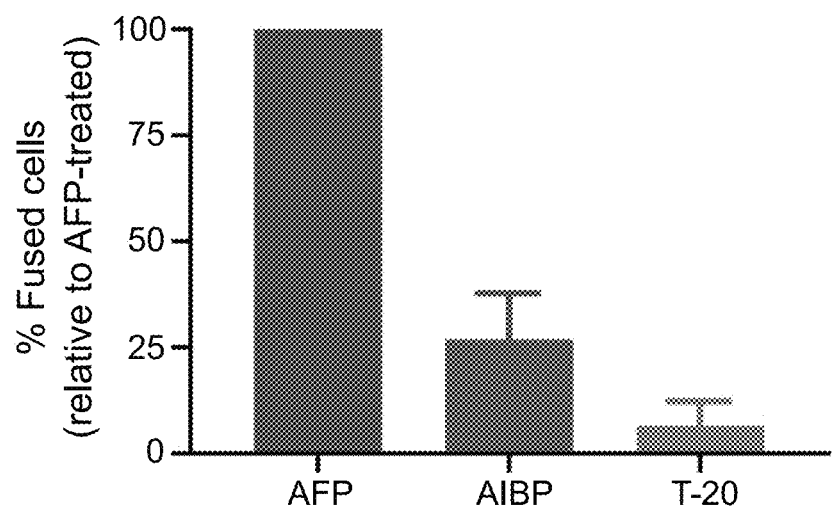

FIG. 10, or S5. Analysis of HIV fusion with MDM. A—MDM were treated with control exosomes for 48 h in the presence of 0.2 µm/ml recombinant AFP or AIBP (both proteins expressed from baculovirus vector) and then infected with BlaM-Vpr carrying HIV-1 NL(AD8) in the presence of AFP, AIBP, or 1 µg/ml T-20. Percentage of fused cells (cleaved CCF-2) was determined by flow cytometry. B—Gating strategy. C—Fusion analysis, performed as described in A, with MDMs from 3 donors. Results (mean±SD) are presented relative to HIV fusion with cells treated with AFP, taken as 100%.

Figure 11:
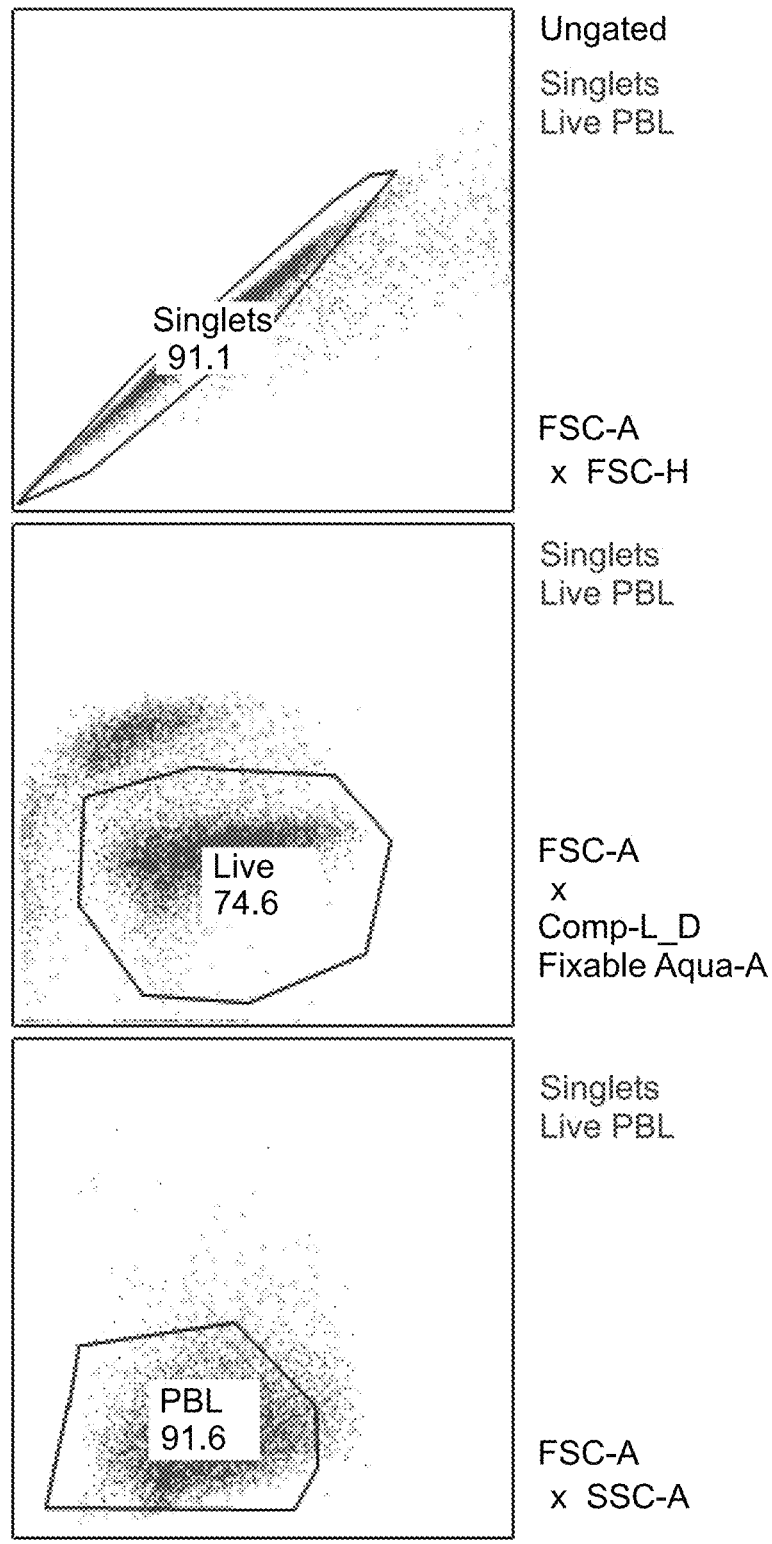
FIG. 11 illustrates flow cytometry gating strategy for FIG. 5E, as further discussed in Example 1, below.

FIG. 11, or S6: illustrates the gating strategy for FIG. 5E.

Example 2

Targeting Lipid Rafts—a Therapy for COVID-19

This example demonstrates that methods and compositions as provided herein using the exemplary embodiments are effective for treating coronaviruses such as COVID-19 and other viral infections.

COVID-19 is a global pandemic currently in an acute phase of rapid expansion. While public health measures remain the most effective protection strategy at this stage, when the peak passes, it will leave in its wake important health problems. Historically, very few viruses have ever been eradicated. Instead, the virus may persist in communities causing recurrent local outbreaks of the acute infection as well as several chronic diseases that may arise from the presence of a "suppressed" virus or as a consequence of the initial exposure. An ideal solution would be an anti-viral medication that (i) targets an early stage of the viral lifecycle, (ii) is insensitive to frequent changes of viral phenotype due to mutagenesis, (iii) has broad spectrum, (iv) is safe and (v) also targets co-morbidities of the infection.

Provided herein is a therapeutic approach that uses "lipid raft therapy". Lipid raft therapy is an approach aimed at reducing the abundance and structural modifications of host lipid rafts or at targeted delivery of therapeutics to the rafts. Lipid rafts are the sites of the initial binding, activation, internalization and cell-to-cell transmission of SARS-CoV-2. They also are key regulators of immune and inflammatory responses, dysregulation of which is characteristic to COVID-19 infection. Lipid raft therapy was successful in targeting many viral infections and inflammatory disorders and can be highly effective for treatment of COVID-19.

Lipid Rafts and Viral Infections

Lipid rafts are solid domains of plasma membrane embedded into predominantly fluid membrane (Lingwood and Simons, 2010). Proteins that work together (for example in multiunit receptors or endocytosis machinery) are usually located in lipid rafts preventing these molecules from drifting apart, instead keeping them in proximity to each other. Lipid rafts host many receptors involved in immune and inflammatory responses and play a key role in regulation of inflammation (Sorci-Thomas and Thomas, 2016), an important attribute given the role of unique pattern of immune and inflammatory responses in the clinical manifestations of COVID-19 (Giamarellos-Bourboulis et al., 2020; Ong et al., 2020). At the same time, numerous viruses, for example HIV and Influenza virus, use host lipid rafts as a "point of entry", owing to rafts harboring high concentration of receptors utilized to bind and guide pathogen as well as affiliated endocytosis machinery ready to take an obligate intracellular parasite inside. Lipid rafts also serve as a platform for pathogen's assembly (for example HIV) and as a "point of exit" (Ebola virus, HIV and HBV (Bukrinsky et al., 2020). Furthermore, viruses often exploit host raft-associated pathways and modify lipid rafts through binding to rafts and/or releasing raft-modifying factors to further promote their infection cycle. The list of viruses where disruption of rafts was shown to inhibit virus infectivity is long and includes HIV, HCV, Influenza A, Ebola and Marburg and many other viruses (for review see (Bagam et al., 2017; Bukrinsky et al., 2020)). SARS-CoV-2 may also be one of such viruses.

Lipid Rafts and Pathogenesis of SARS-Co-2

Molecular pathogenesis of SARS-CoV-2 is schematically presented in FIG. 1. SARS-CoV-2 is very similar to its close relative SARS-CoV and pathogenic pathways of both viruses interact with pathways of cellular cholesterol metabolism (Ballout et al., 2020). Both viruses carry a spike (S) protein in their envelope, which is essential for entry into the host cells (Hoffmann et al., 2020). The S protein docks the viral particle onto angiotensin-converting enzyme 2 (ACE2) (Hofmann and Pohlmann, 2004; Hoffmann et al., 2020), a membrane protein particularly abundant in the plasma membrane of type II pneumocytes, nasal goblet secretory cells and enterocytes (Hoffmann et al., 2020; Ziegler et al., 2020). ACE2 is a lipid raft protein; disruption of lipid rafts prevents its correct exposure making it impossible for the virus to dock (Glende et al., 2008; Lu et al., 2008). After binding to ACE2, the S protein must undergo enzymatic conversion (activation) by either the transmembrane serine protease 2, TMPRSS2, or furin (Hoffmann et al., 2020). The exact location of these proteases on the plasma membrane is unknown, however, TMPRSS2 co-localizes with ACE2 and is potentially palmitoylated (Shulla et al., 2011), indicating likely lipid raft localization. Cleavage-induced conformational change in the S protein and ACE2 allows the host cell membrane to invaginate, which is essential for initiating endocytic viral entry. Endocytic pathway used by SARS-CoV to enter the cell relies on a lipid raft-specific machinery and lipid-raft localization is essential for it to function (Wang et al., 2008). After internalization, the virus undergoes intracellular trafficking within endosomes, which eventually fuse with mature lysosomes. Within the lysosome, the S protein undergoes another series of enzymatic cleavages and modifications, followed by release of the viral RNA genome into the host cytoplasm (Wang et al., 2008). Furthermore, an important feature of both SARS-CoV (Li et al., 2003) and SARS-CoV-2 (Musarrat et al., 2020) is an ability for cell-to-cell transmission, which allows the virus to escape contact with antibody. Cell-to-cell transmission through formation of channels or syncytia requires intact lipid rafts (Niyogi and Hildreth, 2001). Thus, at least four stages of SARS-CoV-2 lifecycle, initial binding, activation, internalization and cell-to-cell transmission, require intact host rafts to proceed (FIG. 1). It follows that targeting host lipid rafts may be an effective strategy to reduce infectivity of SARS-CoV-2, and this was experimentally shown in vitro for SARS-CoV (Li et al., 2007).

Raft Therapies

Targeting lipid rafts for treatment of various diseases, from neurodegeneration and neuropathic pain to cancer, infections and atherosclerosis, is a rapidly growing therapeutic approach, as described in detail in our recent review (Sviridov et al., 2020). Fundamentally, there are two ways to utilize lipid rafts for anti-viral therapy, either to directly disrupt these domains, or to use lipid raft for targeted delivery of anti-viral therapeutics. As only approaches involving lipid raft disruption have been investigated in the context of SARS-CoV-2 pathogenesis (FIG. 1), we will primarily focus on this mechanism.

One approach is to reduce abundance of lipid rafts by depleting them of lipids responsible for their stability, cholesterol or sphingomyelin. For example, cholesterol can be physically removed from rafts by sequestrants, such as cyclodextrins. β-Cyclodextrin is used as a food additive and is proven to be safe for consumption (Mortensen et al., 2016), it inhibits entry of another enveloped virus, HIV, into host cells (Carter et al., 2009) and has anti-inflammatory properties (Zimmer et al., 2016). Another option is stimulation of physiological pathways responsible for the efflux of cholesterol, such as stimulation of the expression of ATP-binding cassette transporters A1 and G1, using LXR agonists or heterologous over-expression of these transporters. Further, elevation of the levels of natural acceptors of cholesterol, high-density lipoprotein (HDL) and apolipoprotein A-I (apoA-I), or infusion of HDL and apoA-I mimetics also reduces the abundance of lipid rafts. The third option is to reduce cholesterol and sphingolipid supply using inhibitors of their biosynthesis, for example statins and Miglustat, respectively. Given the proven safety record of statins, drugs widely used to treat hypercholesterolaemia, they are a good candidate for immediate testing for this application. Finally, recently discovered modulator of lipid rafts, apoA-I Binding Protein (AIBP), may be an especially beneficial "lipid raft therapy" compound to treat COVID-19. AIBP stimulates cholesterol efflux and reduces the abundance of lipid rafts in various tissues (Schneider et al., 2018; Woller et al., 2018; Fang and Miller, 2019), it effectively reduces inflammation (Fang and Miller, 2019) and was recently shown to have an anti-HIV activity (Dubrovsky et al., 2020). Importantly, AIBP targets only cells activated with LPS, cholesterol-loaded or infected, reducing the abundance of lipid rafts to the "healthy level", but not below (Woller et al., 2018; Dubrovsky et al., 2020), a selectivity beneficial for avoiding adverse side-effects. Another advantage of AIBP is that it remains active when administered directly to lungs via inhalation (Choi et al., 2018), an application especially relevant to COVID-19.

Second approach takes advantage of unique partitioning of various receptor assemblies to the lipid rafts allowing for an effective targeting of therapeutic agents specifically to these domains. Lipid-coated nanoparticles (Partlow et al., 2008) or liposomes carrying a vector (for example antibody to ACE2 or another raft protein) can carry anti-viral therapies, such as Irbesartan, an ACE2 antagonist, Camostat mesylate, a TMPRSS2 inhibitor, or heparin, which breaks down proteoglycans essential for the SARS-CoV-2 binding to the cell, thus increasing the treatment efficiency and reducing the effective drug concentration and toxicity. Finally, β-cyclodextrin (Lee et al., 2018) and synthetic HDL (Sabnis et al., 2017; Panja and Jana, 2020) particles can also be used to deliver to cells compounds with limited solubility, such as Remdesivir.

Lipid Rafts and Co-Morbidities of COVID-19

One of the puzzling features of COVID-19 infection is abnormal immune response (Giamarellos-Bourboulis et al., 2020) and severe inflammation resembling autoimmune vasculitis (Verdoni et al., 2020; Zhou et al., 2020) or sepsis (Li et al., 2020). The exact pathogenesis of dysregulation of the immune and inflammatory responses in COVID-19 is unknown and emergency response relies on general anti-inflammatory medications or inhibitors of inflammatory cytokines. These approaches in most cases are effective in mitigating the acute phase, but, if sepsis and autoimmune vasculitis are a guide, heightened chronic inflammation will persist for a long time causing multiple chronic co-morbidities. Lipid rafts play a key role in immunity and inflammation (Sorci-Thomas and Thomas, 2016) and targeting lipid rafts to reduce inflammation is a promising therapeutic approach that can reduce both acute and inflammatory responses (Sviridov et al., 2020). Another common co-morbidity of COVID-19 is coagulopathy (Miesbach and Makris, 2020). Lipid rafts are involved in regulation of platelet function, and lipid raft therapy was effective in attenuating platelet function (Calkin et al., 2009). Thus, therapeutic approaches targeting lipid rafts may mitigate both COVID-19 infection itself and its acute and chronic co-morbidities.

Discussion

Use of "lipid raft therapy" approach has important advantages over other strategies. First, it targets the element of pathogenesis common to both acute and residual infection, as well as the most likely co-morbidities of COVID-19. Second, involvement of lipid rafts in pathogenesis of viral infection is common to many viruses and the proposed treatment may be applicable for both current and future pandemics. Third, it utilises medications that are currently used or being tested for treatment of other diseases, where therapeutic doses were proven to be safe and have high degree of hemocompatibility promising a rapid repurposing for treatment of COVID-19. Finally, it can be used both as a stand-alone therapy and in combination with other therapeutic approaches.

Lipid raft therapy also has some limitations. Agents of lipid raft therapy may induce immune response dangerously combining with the immune response to the SARS-CoV-2. Although no adverse immune reaction to any of the lipid raft therapy agents has been described so far (even to large multiprotein complexes such as HDL), such reaction in the context of COVID-19 infection cannot be a priori dismissed. Conversely, disruption of rafts reduces immune responses, which may have a negative effect on resistance to the virus. However, several lines of evidence suggest that suppressed immunity is not detrimental, but could be even beneficial for the anti-COVID-19 therapy. Immunosuppression and chemotherapy do not have a negative effect on severity of COVID-19 (Koker et al., 2020; Robilotti et al., 2020). Asymptomatic patients have lower level of virus-specific antibody than those with severe disease manifestation (Long et al., 2020). In humans, ACE2, a receptor for SARS-CoV-2, is stimulated by interferon, a key element of anti-viral immune response (Ziegler et al., 2020). Collectively, these findings suggest that SARS-CoV-2 is hijacking immune responses, and mitigation of immune response, perhaps counterintuitively, may be beneficial. Another limitation is that, given that lipid rafts are a central element of numerous signalling pathways, their disruption may have unintended negative consequences for functionality of these pathways. However, this complication is more of a theoretical nature: while phenotype of excessive raft abundance has well-described manifestations, very little is known of phenotype of lipid raft deficiency (Sviridov et al., 2020), most likely due to a high level of redundancy in regulation of lipid raft originating pathways. Furthermore, some therapeutic approaches, such as AIBP, allows "fine tuning" of the rafts, reducing the overabundant lipid rafts to the "normal" level, but not below (Woller et al., 2018; Dubrovsky et al., 2020). Finally, some agents of lipid raft therapy may have side-effects seemingly unrelated to their activity toward lipid rafts. For example, high doses of hydroxypropyl-β-cyclodextrin had unexpected impact on renal and systemic hemodynamics (Rosseels et al., 2013). These potential toxicities should be carefully considered when designing therapeutic regimens.

Figure 12:
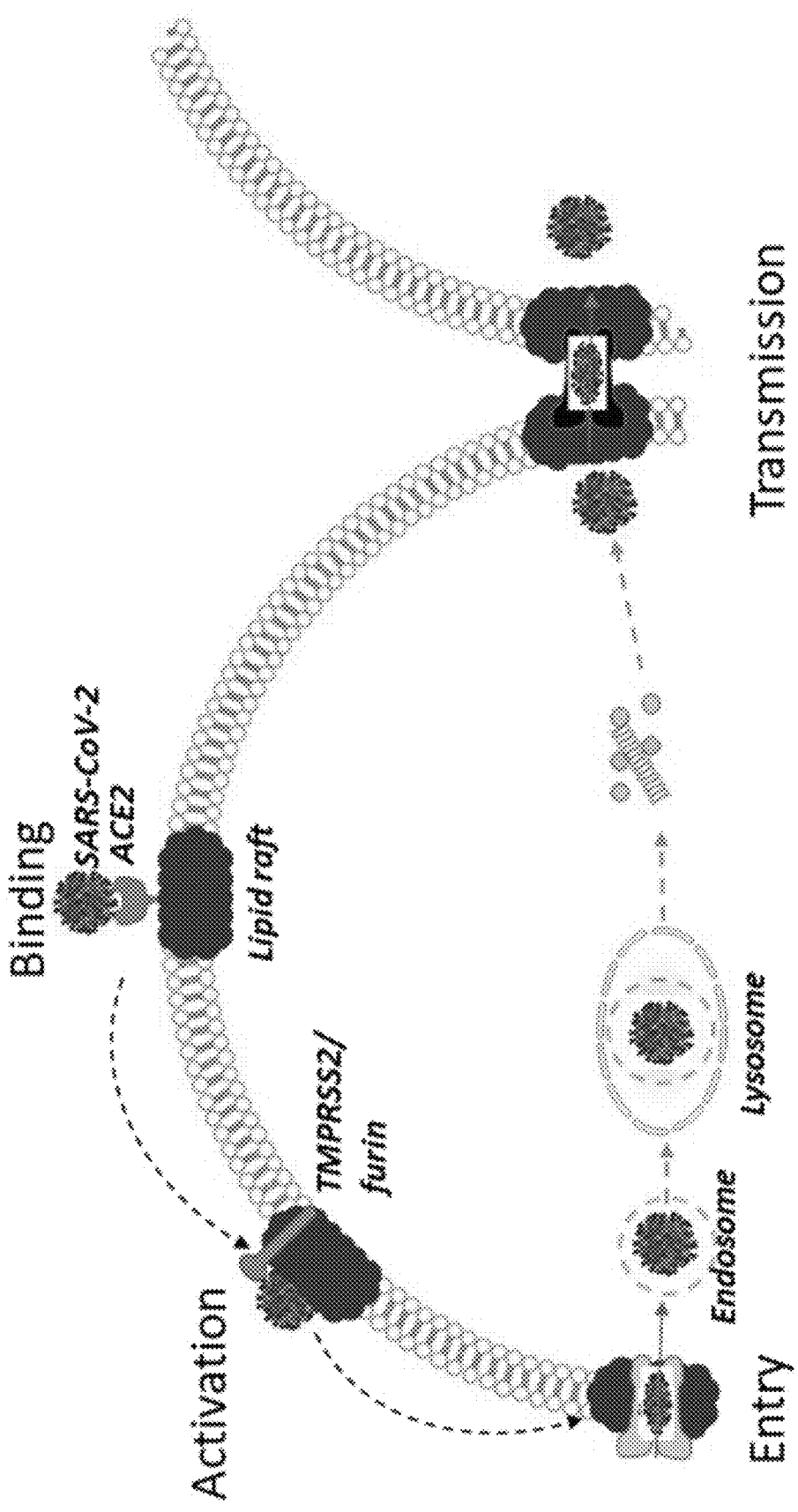
FIG. 12 schematically illustrates the relationship between lipid rafts and the pathogenesis of SARS-CoV-2 (or the coronavirus COVID), as further discussed in Example 1, below Like reference symbols in the various drawings indicate like elements.

Figure Legend Example 2:

FIG. 12. Lipid Rafts and Pathogenesis of SARS-CoV-2

SARS-CoV-2 docks onto ACE2, which is a lipid raft protein. After binding to ACE2 the S protein in the viral envelope undergoes enzymatic activation by TMPRSS2 or furin, which are likely located in lipid rafts. Subsequent endocytosis of SARS-CoV-2 occurs using raft-dependent endocytic pathway. After internalization SARS-CoV-2 undergoes intracellular trafficking within endosomes, fuses with mature lysosomes and releases its viral RNA genome into the host cytoplasm. One of the pathways of virus transmission, cell-to-cell transmission, occurs through formation of intercellular channels or syncytia and also requires intact lipid rafts. Thus, at least four stages of SARS-CoV-2 lifecycle, initial binding, activation, internalization and cell-to-cell transmission, require intact host rafts to proceed and, if other viruses are a guide, disruption of lipid rafts using lipid raft therapy mitigates the infection.

References—Example 1

1. Ritter M, et al. 2002. Cloning and characterization of a novel apolipoprotein A-I binding protein, AI-BP, secreted by cells of the kidney proximal tubules in response to HDL or ApoA-I. Genomics 79:693-702.
2. Marbaix A Y, et al. 2011. Extremely conserved ATP- or ADP-dependent enzymatic system for nicotinamide nucleotide repair. J Biol Chem 286:41246-52.
3. Niehaus T D, Elbadawi-Sidhu M, Huang L, Prunetti L, Gregory J F, 3rd, de Crecy-Lagard V, Fiehn O, Hanson A D. 2018. Evidence that the metabolite repair enzyme NAD(P)HX epimerase has a moonlighting function. Biosci Rep 38:BSR20180223.
4. Gu Q, et al. 2019. AIBP-mediated cholesterol efflux instructs hematopoietic stem and progenitor cell fate. Science 363:1085-1088.
5. Fang L, Choi S H, Baek J S, Liu C, Almazan F, Ulrich F, Wiesner P, Taleb A, Deer E, Pattison J, Torres-Vazquez J, Li A C, Miller Y I. 2013. Control of angiogenesis by AIBP-mediated cholesterol efflux. Nature 498:118-22.
6. Schneider D A, Choi S H, Agatisa-Boyle C, Zhu L, Kim J, Pattison J, Sears D D, Gordts P, Fang L, Miller Y I. 2018. AIBP protects against metabolic abnormalities and atherosclerosis. J Lipid Res 59:854-863.
7. Woller S A, Choi S H, An E J, Low H, Schneider D A, Ramachandran R, Kim J, Bae Y S, Sviridov D, Corr M, Yaksh T L, Miller Y I. 2018. Inhibition of Neuroinflammation by AIBP: Spinal Effects upon Facilitated Pain States. Cell Rep 23:2667-2677.
8. Choi S H, Wallace A M, Schneider D A, Burg E, Kim J, Alekseeva E, Ubags N D, Cool C D, Fang L, Suratt B T, Miller Y I. 2018. AIBP augments cholesterol efflux from alveolar macrophages to surfactant and reduces acute lung inflammation. JCI Insight 3:e120519.
9. Zhang M, Li L, Xie W, Wu J F, Yao F, Tan Y L, Xia X D, Liu X Y, Liu D, Lan G, Zeng M Y, Gong D, Cheng H P, Huang C, Zhao Z W, Zheng X L, Tang C K. 2016. Apolipoprotein A-1 binding protein promotes macrophage cholesterol efflux by facilitating apolipoprotein A-1 binding to ABCA1 and preventing ABCA1 degradation. Atherosclerosis 248:149-159.
10. Ono A. 2010. Relationships between plasma membrane microdomains and HIV-1 assembly. Biol Cell 102:335-50.
11. Manes S, del Real G, Lacalle R A, Lucas P, Gomez-Mouton C, Sanchez-Palomino S, Delgado R, Alcami J, Mira E, Martinez A C. 2000. Membrane raft microdomains mediate lateral assemblies required for HIV-1 infection. EMBO Rep 1:190-6.
12. Nguyen D H, Hildreth J E. 2000. Evidence for budding of human immunodeficiency virus type 1 selectively from glycolipid-enriched membrane lipid rafts. J Virol 74:3264-72.
13. Mujawar Z, Rose H, Morrow M P, Pushkarsky T, Dubrovsky L, Mukhamedova N, Fu Y, Dart A, Orenstein J M, Bobryshev Y V, Bukrinsky M, Sviridov D. 2006. Human immunodeficiency virus impairs reverse cholesterol transport from macrophages. PLoS Biol 4:e365.
14. Zheng Y H, Plemenitas A, Fielding C J, Peterlin B M. 2003. Nef increases the synthesis of and transports cholesterol to lipid rafts and HIV-1 progeny virions. Proc Natl Acad Sci USA 100:8460-5.
15. van't Wout A B, Swain J V, Schindler M, Rao U, Pathmajeyan M S, Mullins J I, Kirchhoff F. 2005. Nef induces multiple genes involved in cholesterol synthesis and uptake in human immunodeficiency virus type 1-infected T cells. J Virol 79:10053-10058.
16. Zheng Y H, Plemenitas A, Linnemann T, Fackler O T, Peterlin B M. 2001. Nef increases infectivity of HIV via lipid rafts. Curr Biol 11:875-9.
17. Cui H L, Grant A, Mukhamedova N, Pushkarsky T, Jennelle L, Dubrovsky L, Gaus K, Fitzgerald M L, Sviridov D, Bukrinsky M. 2012. HIV-1 Nef mobilizes lipid rafts in macrophages through a pathway that competes with ABCA1-dependent cholesterol efflux. J Lipid Res 53:696-708.
18. Asztalos B F, Mujawar Z, Morrow M P, Grant A, Pushkarsky T, Wanke C, Shannon R, Geyer M, Kirchhoff F, Sviridov D, Fitzgerald M L, Bukrinsky M, Mansfield K G. 2010. Circulating Nef induces dyslipidemia in simian immunodeficiency virus-infected macaques by suppressing cholesterol efflux. J Infect Dis 202:614-23.
19. Cui H L, Ditiatkovski M, Kesani R, Bobryshev Y V, Liu Y, Geyer M, Mukhamedova N, Bukrinsky M, Sviridov D. 2014. HIV protein Nef causes dyslipidemia and formation of foam cells in mouse models of atherosclerosis. FASEB J 28:2828-39.
20. McNamara R P, Costantini L M, Myers T A, Schouest B, Maness N J, Griffith J D, Damania B A, MacLean A G, Dittmer D P. 2018. Nef secretion into extracellular vesicles or exosomes is conserved across Human and Simian Immunodeficiency Viruses. MBio 9:e02344-17.
21. Lenassi M, Cagney G, Liao M, Vaupotic T, Bartholomeeusen K, Cheng Y, Krogan N J, Plemenitas A, Peterlin B 21. M. 2010. HIV Nef is secreted in exosomes and triggers apoptosis in bystander CD4+ T cells. Traffic 11:110-22.
22. Guyader M, Kiyokawa E, Abrami L, Turelli P, Trono D. 2002. Role for human immunodeficiency virus type 1 membrane cholesterol in viral internalization. J Virol 76:10356-64.
23. Ono A, Freed E O. 2001. Plasma membrane rafts play a critical role in HIV-1 assembly and release. Proc Natl Acad Sci USA 98:13925-30.
24. Khanna K V, Whaley K J, Zeitlin L, Moench T R, Mehrazar K, Cone R A, Liao Z, Hildreth J E, Hoen T E, Shultz L, Markham R B. 2002. Vaginal transmission of cell-associated HIV-1 in the mouse is blocked by a topical, membrane-modifying agent. J Clin Invest 109:205-211.
25. Maziere J C, Landureau J C, Giral P, Auclair M, Fall L, Lachgar A, Achour A, Zagury D. 1994. Lovastatin inhibits HIV-1 expression in H9 human T lymphocytes cultured in cholesterol-poor medium. Biomed Pharmacother 48:63-67.
26. del Real G, et al. 2004. Statins inhibit HIV-1 infection by down-regulating Rho activity. J Exp Med 200:541-7.
27. Ramezani A, et al. 2015. Stimulation of Liver X Receptor Has Potent Anti-HIV Effects in a Humanized Mouse Model of HIV Infection. J Pharmacol Exp Ther 354:376-83.
28. Morrow M P, et al. 2010. Stimulation of the liver X receptor pathway inhibits HIV-1 replication via induction of ATP-binding cassette transporter A1. Mol Pharmacol 78:215-25.
29. Schmidtmayerova H, Nuovo G J, Bukrinsky M. 1997. Cell proliferation is not required for productive HIV-1 infection of macrophages. Virology 232:379-384.
30. Ochsenbauer C, et al. 2012. Generation of transmitted/founder HIV-1 infectious molecular clones and characterization of their replication capacity in CD4 T lymphocytes and monocyte-derived macrophages. J Virol 86:2715-28.
31. Livshits M A, Khomyakova E, Evtushenko E G, Lazarev V N, Kulemin N A, Semina S E, Generozov E V, Govorun V M. 2015. Isolation of exosomes by differential centrifugation: Theoretical analysis of a commonly used protocol. Sci Rep 5:17319.
32. Raposo G, Stoorvogel W. 2013. Extracellular vesicles: exosomes, microvesicles, and friends. J Cell Biol 200:373-83.
33. Cavrois M, de Noronha C, Greene W C. 2002. A sensitive and specific enzyme-based assay detecting HIV-1 virion fusion in primary T lymphocytes. Nat Biotechnol 20:1151-1154.
34. Freed E O, Englund G, Martin M A. 1995. Role of the basic domain of human immunodeficiency virus type 1 matrix in macrophage infection. J Virol 69:3949-3954.
35. Papkalla A, Munch J, Otto C, Kirchhoff F. 2002. Nef enhances human immunodeficiency virus type 1 infectivity and replication independently of viral coreceptor tropism. J Virol 76:8455-8459.
36. Huang X, Hartley A V, Yin Y, Herskowitz J H, Lah J J, Ressler K J. 2013. AAV2 production with optimized N/P ratio and PEI-mediated transfection results in low toxicity and high titer for in vitro and in vivo applications. J Virol Methods 193:270-7.
37. Shugars D C, Smith M S, Glueck D H, Nantermet P V, Seillier-Moiseiwitsch F, Swanstrom R. 1993. Analysis of human immunodeficiency virus type 1 nef gene sequences present in vivo. J Virol 67:4639-4650.
38. Simm M, Shahabuddin M, Chao W, Allan J S, Volsky D J. 1995. Aberrant Gag protein composition of a human immunodeficiency virus type 1 vif mutant produced in primary lymphocytes. J Virol 69:4582-4586.
39. Cillo A R, Vagratian D, Bedison M A, Anderson E M, Kearney M F, Fyne E, Koontz D, Coffin J M, Piatak M, Jr., Mellors J W. 2014. Improved single-copy assays for quantification of persistent HIV-1 viremia in patients on suppressive antiretroviral therapy. J Clin Microbiol 52:3944-51.
40. Parrish N F, et al. 2013. Phenotypic properties of transmitted founder HIV-1. Proc Natl Acad Sci USA 110:6626-33.
41. Li H, Chen B K. 2019. Variable infectivity and conserved engagement in cell-to-cell viral transfer by HIV-1 Env from Clade B transmitted founder clones. Virology 526:189-202.
42. Li Q, et al. 2009. Glycerol monolaurate prevents mucosal SIV transmission. Nature 458:1034-8.
43. Yang S T, Kiessling V, Simmons J A, White J M, Tamm L K. 2015. HIV gp41-mediated membrane fusion occurs at edges of cholesterol-rich lipid domains. Nat Chem Biol 11:424-31.
44. Nichols B J. 2003. GM1-containing lipid rafts are depleted within clathrin-coated pits. Curr Biol 13:686-90.
45. Gonzalez Porras M A, et al. 2019. Frequency-dependent lipid raft uptake at rat diaphragm muscle axon terminals. Muscle Nerve 59:611-618.
46. Danielsen E M, Hansen G H. 2013. Generation of stable lipid raft microdomains in the enterocyte brush border by selective endocytic removal of non-raft membrane. PLoS One 8:e76661.
47. Mrowczynska L, Salzer U, Perutkova S, Iglic A, Hagerstrand H. 2010. Echinophilic proteins stomatin, sorcin, and synexin locate outside gangliosideM1 (GM1) patches in the erythrocyte membrane. Biochem Biophys Res Commun 401:396-400.
48. Tuosto L, Parolini I, Schroder S, Sargiacomo M, Lanzavecchia A, Viola A. 2001. Organization of plasma membrane functional rafts upon T cell activation. Eur J Immunol 31:345-9.
49. Tani-ichi S, et al. 2005. Structure and function of lipid rafts in human activated T cells. Int Immunol 17:749-58.
50. Franchin G, et al. 2000. Lipopolysaccharide inhibits HIV-1 infection of monocyte-derived macrophages through direct and sustained down-regulation of CC chemokine receptor S. J Immunol 164:2592-601.
51. Pushkarsky T, Dubrovsky L, Bukrinsky M. 2001. Lipopolysaccharide stimulates HIV-1 entry and degradation in human macrophages. J Endotoxin Res 7:271-6.
52. Mukhamedova N, et al. 2019. Exosomes containing HIV protein Nef reorganize lipid rafts potentiating inflammatory response in bystander cells. PLoS Pathog 15:e1007907.
53. Pegtel D M, Gould S J. 2019. Exosomes. Annu Rev Biochem 88:487-514.
54. Thery C, et al. 2018. Minimal information for studies of extracellular vesicles 2018 (MISEV2018): a position statement of the International Society for Extracellular Vesicles and update of the MISEV2014 guidelines. J Extracell Vesicles 7:1535750.
55. Arakelyan A, Fitzgerald W, Zicari S, Vanpouille C, Margolis L. 2017. Extracellular Vesicles Carry HIV Env and Facilitate Hiv Infection of Human Lymphoid Tissue. Sci Rep 7:1695.

56. Nolte-'t Hoen E, Cremer T, Gallo R C, Margolis L B. 2016. Extracellular vesicles and viruses: Are they close relatives? Proc Natl Acad Sci USA 113:9155-61.
57. Cavrois M, Neidleman J, Yonemoto W, Fenard D, Greene W C. 2004. HIV-1 virion fusion assay: uncoating not required and no effect of Nef on fusion. Virology 328:36-44.
58. Tobiume M, Lineberger J E, Lundquist C A, Miller M D, Aiken C. 2003. Nef does not affect the efficiency of human immunodeficiency virus type 1 fusion with target cells. J Virol 77:10645-10650.
59. Grivel J C, Shattock R J, Margolis L B. 2011. Selective transmission of R5 HIV-1 variants: where is the gatekeeper? J Transl Med 9 Suppl 1:S6.
60. Grimm D, Lee J S, Wang L, Desai T, Akache B, Storm T A, Kay M A. 2008. In vitro and in vivo gene therapy vector evolution via multispecies interbreeding and retargeting of adeno-associated viruses. J Virol 82:5887-911.
61. McLaren P J, Carrington M. 2015. The impact of host genetic variation on infection with HIV-1. Nat Immunol 16:577-83.
62. Carrington M, Nelson G W, Martin M P, Kissner T, Vlahov D, Goedert J J, Kaslow R, Buchbinder S, Hoots K, O'Brien S J. 1999. HLA and HIV-1: heterozygote advantage and B*35-Cw*04 disadvantage. Science 283:1748-52.
63. Gao X, Nelson G W, Karacki P, Martin M P, Phair J, Kaslow R, Goedert J J, Buchbinder S, Hoots K, Vlahov D, O'Brien S J, Carrington M. 2001. Effect of a single amino acid change in MHC class I molecules on the rate of progression to AIDS. N Engl J Med 344:1668-75.
64. Kaslow R A, Carrington M, Apple R, Park L, Munoz A, Saah A J, Goedert J J, Winkler C, O'Brien S J, Rinaldo C, Detels R, Blattner W, Phair J, Erlich H, Mann D L. 1996. Influence of combinations of human major histocompatibility complex genes on the course of HIV-1 infection. Nat Med 2:405-11.
65. Martin M P, Carrington M. 2013. Immunogenetics of HIV disease. Immunol Rev 254:245-64.
66. Migueles S A, Sabbaghian M S, Shupert W L, Bettinotti M P, Marincola F M, Martino L, Hallahan C W, Selig S M, Schwartz D, Sullivan J, Connors M. 2000. HLA B*5701 is highly associated with restriction of virus replication in a subgroup of HIV-infected long term nonprogressors. Proc Natl Acad Sci USA 97:2709-14.
67. International HIVCS, Pereyra F, et al. 2010. The major genetic determinants of HIV-1 control affect HLA class I peptide presentation. Science 330:1551-7.
68. Vereb G, Matko J, Vamosi G, Ibrahim S M, Magyar E, Varga S, Szollosi J, Jenei A, Gaspar R, Jr., Waldmann T A, Damjanovich S. 2000. Cholesterol-dependent clustering of IL-2Ralpha and its colocalization with HLA and CD48 on T lymphoma cells suggest their functional association with lipid rafts. Proc Natl Acad Sci USA 97:6013-8.
69. Zhang M, Zhao G J, Yao F, Xia X D, Gong D, Zhao Z W, Chen L Y, Zheng X L, Tang X E, Tang C K. 2018. AIBP reduces atherosclerosis by promoting reverse cholesterol transport and ameliorating inflammation in apoE (−/−) mice. Atherosclerosis 273:122-130.
70. Lee J H, Schierer S, Blume K, Dindorf J, Wittki S, Xiang W, Ostalecki C, Koliha N, Wild S, Schuler G, Fackler O T, Saksela K, Harrer T, Baur A S. 2016. HIV-Nef and ADAM17-Containing Plasma Extracellular Vesicles Induce and Correlate with Immune Pathogenesis in Chronic HIV Infection. EBioMedicine 6:103-113.
71. Ferdin J, Goricar K, Dolzan V, Plemenitas A, Martin J N, Peterlin B M, Deeks S G, Lenassi M. 2018. Viral protein Nef is detected in plasma of half of HIV-infected adults with undetectable plasma HIV RNA. PLoS One 13:e0191613.
72. Joseph A M, Kumar M, Mitra D. 2005. Nef: "necessary and enforcing factor" in HIV infection. Curr HIV Res 3:87-94.
73. Kestler H W, III, Ringler D J, Mori K, Panicali D L, Sehgal P K, Daniel M D, Desrosiers R C. 1991. Importance of the nef gene for maintenance of high virus loads and for development of AIDS. Cell 65:651-662.
74. Learmont J C, Geczy A F, Mills J, Ashton L J, Raynes-Greenow C H, Garsia R J, Dyer W B, McIntyre L, Oelrichs R B, Rhodes D I, Deacon N J, Sullivan J S. 1999. Immunologic and virologic status after 14 to 18 years of infection with an attenuated strain of HIV-1. A report from the Sydney Blood Bank Cohort. N Engl J Med 340:1715-22.
75. Collins K L, Baltimore D. 1999. HIV's evasion of the cellular immune response. Immunol Rev 168:65-74.
76. Lundquist C A, Tobiume M, Zhou J, Unutmaz D, Aiken C. 2002. Nef-mediated downregulation of CD4 enhances human immunodeficiency virus type 1 replication in primary T lymphocytes. J Virol 76:4625-33.
77. Usami Y, Wu Y, Gottlinger H G. 2015. SERINC3 and SERINC5 restrict HIV-1 infectivity and are counteracted by Nef. Nature 526:218-223.
78. Rosa A, Chande A, Ziglio S, De Sanctis V, Bertorelli R, Goh S L, McCauley S M, Nowosielska A, Antonarakis S E, Luban J, Santoni F A, Pizzato M. 2015. HIV-1 Nef promotes infection by excluding SERINC5 from virion incorporation. Nature 526:212-217.
79. Sood C, Marin M, Chande A, Pizzato M, Melikyan G B. 2017. SERINC5 protein inhibits HIV-1 fusion pore formation by promoting functional inactivation of envelope glycoproteins. J Biol Chem 292:6014-6026.
80. Tedbury P R, Sarafianos S G. 2017. Exposing HIV's weaknesses. J Biol Chem 292:6027-6028.
81. Buchner S M, Sliva K, Bonig H, Volker I, Waibler Z, Kirberg J, Schnierle B S. 2013. Delayed onset of graft-versus-host disease in immunodeficent human leucocyte antigen-DQ8 transgenic, murine major histocompatibility complex class II-deficient mice repopulated by human peripheral blood mononuclear cells. Clin Exp Immunol 173:355-64.
82. Campbell J H, Hearps A C, Martin G E, Williams K C, Crowe S M. 2014. The importance of monocytes and macrophages in HIV pathogenesis, treatment, and cure. AIDS 28:2175-87.
83. Brichacek B, Darwish C, Popratiloff A, Dubrovsky L, Bukrinsky M. 2014. HIV-1 Infection of Macrophages Induces Retention of Cholesterol Transporter ABCA1 in the Endoplasmic Reticulum. AIDS Res Hum Retroviruses 30:947-948.
84. Bukrinsky M I, Mukhamedova N, Sviridov D. 2019. Lipid Rafts and Pathogens: The Art of Deception and Exploitation. J Lipid Res doi:10.1194/jlr.TR119000391.

References Example 2

Altman, M. O., Angeletti, D., and Yewdell, J. W. (2018). Antibody Immunodominance: The Key to Understanding Influenza Virus Antigenic Drift. *Viral Immunol* 31, 142-149.

Bagam, P., Singh, D. P., Inda, M. E., and Batra, S. (2017). Unraveling the role of membrane microdomains during microbial infections. *Cell Biol Toxicol.*

Ballout, R. A., Sviridov, D., Bukrinsky, M. I., and Remaley, A. T. (2020). The lysosome: A potential juncture between SARS-CoV-2 infectivity and Niemann-Pick disease type C, with therapeutic implications. *Faseb j* 34, 7253-7264.

Bukrinsky, M. I., Mukhamedova, N., and Sviridov, D. (2020). Lipid rafts and pathogens: the art of deception and exploitation. *J Lipid Res* 61, 601-610.

Calkin, A. C., Drew, B. G., Ono, A., Duffy, S. J., Gordon, M. V., Schoenwaelder, S. M., et al. (2009). Reconstituted High-Density Lipoprotein Attenuates Platelet Function in Individuals With Type 2 Diabetes Mellitus by Promoting Cholesterol Efflux. *Circulation* 120, 2095-2104.

Carter, G. C., Bernstone, L., Sangani, D., Bee, J. W., Harder, T., and James, W. (2009). HIV entry in macrophages is dependent on intact lipid rafts. *Virology* 386, 192-202.

Choi, S.-H., Wallace, A. M., Schneider, D. A., Burg, E., Kim, J., Alekseeva, E., et al. (2018). AIBP augments cholesterol efflux from alveolar macrophages to surfactant and reduces acute lung inflammation. *JCI Insight* 3.

Diamond, M. S., and Pierson, T. C. (2020). The Challenges of Vaccine Development against a New Virus during a Pandemic. *Cell Host & Microbe* 27, 699-703.

Dubrovsky, L., Ward, A., Choi, S.-H., Pushkarsky, T., Brichacek, B., Vanpouille, C., et al. (2020). Inhibition of HIV Replication by Apolipoprotein A-I Binding Protein Targeting the Lipid Rafts. *mBio* 11, e02956-02919.

Fang, L., and Miller, Y. I. (2019). Regulation of lipid rafts, angiogenesis and inflammation by AIBP. *Curr Opin Lipidol* 30, 218-223.

Giamarellos-Bourboulis, E. J., Netea, M. G., Rovina, N., Akinosoglou, K., Antoniadou, A., Antonakos, N., et al. (2020). Complex Immune Dysregulation in COVID-19 Patients with Severe Respiratory Failure. *Cell Host & Microbe* 27, 992-1000.e1003.

Glende, J., Schwegmann-Wessels, C., Al-Falah, M., Pfefferle, S., Qu, X., Deng, H., et al. (2008). Importance of cholesterol-rich membrane microdomains in the interaction of the S protein of SARS-coronavirus with the cellular receptor angiotensin-converting enzyme 2. *Virology* 381, 215-221.

He, Y., Wang, J., Li, F., and Shi, Y. (2020). Main Clinical Features of COVID-19 and Potential Prognostic and Therapeutic Value of the Microbiota in SARS-CoV-2 Infections. *Frontiers in Microbiology* 11.

Hoffmann, M., Kleine-Weber, H., Schroeder, S., Kruger, N., Herrler, T., Erichsen, S., et al. (2020). SARS-CoV-2 Cell Entry Depends on ACE2 and TMPRSS2 and Is Blocked by a Clinically Proven Protease Inhibitor. *Cell* 181, 271-280.e278.

Hofmann, H., and Pohlmann, S. (2004). Cellular entry of the SARS coronavirus. *Trends Microbiol* 12, 466-472.

Koker, O., Demirkan, F. G., Kayaalp, G., Cakmak, F., Tanatar, A., Karadag, S. G., et al. (2020). Does immunosuppressive treatment entail an additional risk for children with rheumatic diseases? A survey-based study in the era of COVID-19. *Rheumatol Int*, 1-11.

Lee, S. Y., Ko, S. H., Shim, J. S., Kim, D. D., and Cho, H. J. (2018). Tumor Targeting and Lipid Rafts Disrupting Hyaluronic Acid-Cyclodextrin-Based Nanoassembled Structure for Cancer Therapy. *ACS Appl Mater Interfaces* 10, 36628-36640.

Li, G. M., Li, Y. G., Yamate, M., Li, S. M., and Ikuta, K. (2007). Lipid rafts play an important role in the early stage of severe acute respiratory syndrome-coronavirus life cycle. *Microbes Infect* 9, 96-102.

Li, H., Liu, L., Zhang, D., Xu, J., Dai, H., Tang, N., et al. (2020). SARS-CoV-2 and viral sepsis: observations and hypotheses. *Lancet* 395, 1517-1520.

Li, W., Moore, M. J., Vasilieva, N., Sui, J., Wong, S. K., Berne, M. A., et al. (2003). Angiotensin-converting enzyme 2 is a functional receptor for the SARS coronavirus. *Nature* 426, 450-454.

Lingwood, D., and Simons, K. (2010). Lipid Rafts As a Membrane-Organizing Principle. *Science* 327, 46-50.

Long, Q.-X., Tang, X.-J., Shi, Q.-L., Li, Q., Deng, H.-J., Yuan, J., et al. (2020). Clinical and immunological assessment of asymptomatic SARS-CoV-2 infections. *Nature Medicine* 26, 1200-1204.

Lu, Y., Liu, D. X., and Tam, J. P. (2008). Lipid rafts are involved in SARS-CoV entry into Vero E6 cells. *Biochem Biophys Res Commun* 369, 344-349.

Miesbach, W., and Makris, M. (2020). COVID-19: Coagulopathy, Risk of Thrombosis, and the Rationale for Anticoagulation. *Clin Appl Thromb Hemost* 26, 1076029620938149.

Mortensen, A., et al. (2016). Re-evaluation of β-cyclodextrin (E 459) as a food additive. *EFSA Journal* 14, e04628.

Musarrat, F., et al. (2020). The anti-HIV drug nelfinavir mesylate (Viracept) is a potent inhibitor of cell fusion caused by the SARSCoV-2 spike (S) glycoprotein warranting further evaluation as an antiviral against COVID-19 infections. *J Med Virol*.

Niyogi, K., and Hildreth, J. E. (2001). Characterization of new syncytium-inhibiting monoclonal antibodies implicates lipid rafts in human T-cell leukemia virus type 1 syncytium formation. *J Virol* 75, 7351-7361.

Omsland, M., et al. (2018). Inhibition of Tunneling Nanotube (TNT) Formation and Human T-cell Leukemia Virus Type 1 (HTLV-1) Transmission by Cytarabine. *Sci Rep* 8, 11118.

Ong, E. Z., et al. (2020). A Dynamic Immune Response Shapes COVID-19 Progression. *Cell Host & Microbe* 27, 879-882.e872.

Panja, P., and Jana, N. R. (2020). Lipid-Raft-Mediated Direct Cytosolic Delivery of Polymer-Coated Soft Nanoparticles. *J Phys Chem B* 124, 5323-5333.

Partlow, K. C., et al. (2008). Exploiting lipid raft transport with membrane targeted nanoparticles: a strategy for cytosolic drug delivery. *Biomaterials* 29, 3367-3375.

Robilotti, E. V., et al. (2020). Determinants of COVID-19 disease severity in patients with cancer. *Nature Medicine* 26, 1218-1223.

Rosseels, M. L., et al. (2013). Hydroxypropyl-β-cyclodextrin impacts renal and systemic hemodynamics in the anesthetized dog. *Regul Toxicol Pharmacol* 67, 351-359.

Sabnis, S., et al. (2017). Superparamagnetic reconstituted high-density lipoprotein nanocarriers for magnetically guided drug delivery. *Int J Nanomedicine* 12, 1453-1464.

Schneider, D. A., et al. (2018). AIBP protects against metabolic abnormalities and atherosclerosis. *Journal of Lipid Research* 59, 854-863.

Shulla, A., et al. (2011). A transmembrane serine protease is linked to the severe acute respiratory syndrome coronavirus receptor and activates virus entry. *J Virol* 85, 873-882.

Sorci-Thomas, M. G., and Thomas, M. J. (2016). Microdomains, Inflammation, and Atherosclerosis. *Circ Res* 118, 679-691.

Sviridov, D., et al. (2020). Lipid rafts as a therapeutic target. *J Lipid Res* 61, 687-695.

Verdoni, L., et al. (2020). An outbreak of severe Kawasaki-like disease at the Italian epicentre of the SARS-CoV-2 epidemic: an observational cohort study. *Lancet*.

Wang, H., et al. (2008). SARS coronavirus entry into host cells through a novel clathrin- and caveolae-independent endocytic pathway. *Cell Research* 18, 290-301.

Woller, S. A., et al., Ramachandran, R., et al. (2018). Inhibition of Neuroinflammation by AIBP: Spinal Effects upon Facilitated Pain States. *Cell Reports* 23, 2667-2677.

Zhou, Z., et al. (2020). Heightened Innate Immune Responses in the Respiratory Tract of COVID-19 Patients. *Cell Host Microbe*.

Ziegler, C. G. K., et al. (2020). SARS-CoV-2 Receptor ACE2 Is an Interferon-Stimulated Gene in Human Airway Epithelial Cells and Is Detected in Specific Cell Subsets across Tissues. *Cell* 181, 1016-1035 e1019.

Zimmer, S., et al. (2016). Cyclodextrin promotes atherosclerosis regression via macrophage reprogramming. *Sci Transl Med* 8, 333ra350.

A number of embodiments of the invention have been described. Nevertheless, it can be understood that various modifications may be made without departing from the spirit and scope of the invention. Accordingly, other embodiments are within the scope of the following claims.

What is claimed is:

1. A method for inhibiting, or slowing the rate of human immunodeficiency virus (HIV) replication in vivo,
the method comprising:
(a) providing or having provided a recombinant protein having Apolipoprotein A-I binding protein (AIBP) activity or a composition comprising the recombinant protein having Apolipoprotein A-I binding protein (AIBP) activity,
wherein the recombinant protein is encoded by a nucleic acid comprising a sequence as set forth in SEQ ID NO:10, and
(b) administering to an individual in need thereof the recombinant protein or the composition.

2. The method of claim 1, wherein the individual in need is an HIV-infected human.

3. The method of claim 1, wherein the recombinant protein or the composition is formulated
for administration in vitro or in vivo.

4. The method of claim 1, wherein the recombinant protein or the composition is formulated as or in a nanoparticle, a nanolipoparticle, a vesicle or a liposomal membrane.

5. The method of claim 1, wherein the recombinant protein is encoded by a nucleic acid consisting essentially of a sequence as set forth in SEQ ID NO: 10.

6. The method of claim 5, wherein the protein or the composition having Apolipoprotein A-I binding protein (AIBP) activity is encoded by a nucleic acid consisting of a sequence as set forth in SEQ ID NO:10.

7. The method of claim 1, wherein the recombinant protein is administered at a daily amount of between about 0.1 to 0.5 to about 20 more ug per kilogram of body weight per day; or, is administered in dosages from about 1 mg to about 4 mg per kg of body weight per patient per day.

8. The method of claim 3, wherein the sterile solution comprises: an injectable solution or buffered saline solution.

9. The method of claim 8, wherein the injectable solution comprises an injectable saline.

10. The method of claim 7, wherein the recombinant protein is administered at a daily amount of about 50 or more ug per kilogram of body weight per day.

11. The method of claim 10, wherein the recombinant protein is administered at a daily amount of about 100 or more ug per kilogram of body weight per day.

12. The method of claim 11, wherein the recombinant protein is administered at a daily amount of about 1000 or more ug per kilogram of body weight per day.

13. The method of claim 3, wherein the recombinant protein or the composition is formulated for enteral or parenteral administration.

14. The method of claim 3, wherein the recombinant protein or the composition is formulated as a liposome, a nanoparticle, or a nanoliposome.

15. The method of claim 3, wherein the recombinant protein or the composition is formulated as a tablet, a pill, a capsule, a gel, a hydrogel, a geltab, a liquid, a powder, an emulsion, a lotion, an aerosol, a spray, a lozenge, a sterile solution, an eye drop, or an implant.

16. The method of claim 3, wherein the recombinant protein or the composition is formulated for intravenous injection, subcutaneous injection, intramuscular injection, inhalation, or intravitreal injection.

* * * * *

UNITED STATES PATENT AND TRADEMARK OFFICE
CERTIFICATE OF CORRECTION

PATENT NO. : 12,227,562 B2
APPLICATION NO. : 17/544416
DATED : December 7, 2021
INVENTOR(S) : Yury Miller et al.

It is certified that error appears in the above-identified patent and that said Letters Patent is hereby corrected as shown below:

In the Specification

Column 1, Lines 9-13, under "GOVERNMENT RIGHTS", please delete:
"This invention was made with government support under HL135737, HL131473, P30 AI117970, P30 AI055019, NS102432, HL136275, NS104769, awarded by the National Institutes of Health. The government has certain rights in the invention."

And replace with:
"This invention was made with government support under HL135737 and HL131473 awarded by the National Institutes of Health. The government has certain rights in the invention."

Signed and Sealed this
Twenty-fifth Day of November, 2025

John A. Squires
*Director of the United States Patent and Trademark Office*

SEQUENCE LISTING

```
<160> NUMBER OF SEQ ID NOS: 11

<210> SEQ ID NO 1
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 1
cgaguguguc uaucgucug                                                  19

<210> SEQ ID NO 2
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 2
ugacgauuga ugaacugua                                                  19

<210> SEQ ID NO 3
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 3
cuacuguccu ggucaucug                                                  19

<210> SEQ ID NO 4
<211> LENGTH: 19
<212> TYPE: RNA
<213> ORGANISM: artificial sequence
<220> FEATURE:
<223> OTHER INFORMATION: synthetic oligonucleotide

<400> SEQUENCE: 4
ucagcgugga ccaacuuau                                                  19

<210> SEQ ID NO 5
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 5
tttggaaagg accagcaaa                                                  19
```

```
<210> SEQ ID NO 6
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 6
cctgccatct gttttcca                                                 18

<210> SEQ ID NO 7
<211> LENGTH: 31
<212> TYPE: DNA
<213> ORGANISM: artificial sequence
<220> FEATURE:
<223> OTHER INFORMATION: synthetic oligonucleotide

<400> SEQUENCE: 7
aaaggtgaag gggcagtagt aatacatamr a                                  31

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
ccctacaatc cccaaagtca                                               20

<210> SEQ ID NO 9
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 9
cacaatcatc acctgccatc                                               20

<210> SEQ ID NO 10
<211> LENGTH: 1121
<212> TYPE: DNA
<213> ORGANISM: homo sapiens

<400> SEQUENCE: 10
gggccgggcc gggccggggg cgcgcgctct gcgagctgga tgtccaggct gcgggcgctg    60
ctgggcctcg gctgctggt tgcgggctcg cgcgtgccgc ggatcaaaag ccagaccatc    120
gcctgtcgct cgggacccac ctggtgggga ccgcagcggc tgaactcggg tggccgctgg    180
gactcagagg tcatggcgag cacggtggtg aagtacctga ccaggagga gcccaggcc     240 gtggaccagg agctatttaa cgaataccag ttcagcgtgg accaacttat ggaactggcc    300
gggctgagct gtgctacagc catcgccaag gcatatcccc ccacgtccat gtccaggagc    360 cccccctactg tcctggtcat ctgtggcccg gggaataatg gaggagatgg tctggtctgt    420
gctcgacacc tcaaactctt tggctacgag ccaaccatct attacccaa aaggcctaac    480 aagcccctct tcactgcatt ggtgaccag tgtcagaaaa tggacatccc tttccttggg    540
gaaatgcccg cagagcccat gacgattgat gaactgtatg agctggtggt ggatgccatc    600
tttggcttca gcttcaaggg cgatgttcgg gaaccgttcc acagcatcct gagtgtcctg    660
aagggactca ctgtgcccat tgccagcatc gacattccct caggatggga cgtggagaag    720
```

-continued

```
ggaaatgctg gagggatcca gccagacttg ctcatatccc tcacagcccc caaaaaatct    780
gcaacccagt ttaccggtcg ctaccattac ctgggggggtc gttttgtgcc acctgctctg    840
gagaagaagt accagctgaa cctgccaccc taccctgaca ccgagtgtgt ctatcgtctg    900
cagtgaggga aggtgggtgg gtattcttcc aataaaagac ttagagcccc tctcttccag    960
aactgtggat tcctgggagc tcctctggca ataaaagtca gtgaatggtg gaagtcagag    1020
accaaccctg gggattgggt gccatctctc tagggggtaac acaaagggca agaggttgct    1080
atggtatttg gaaacaatga aaatggactg ttagatgcca a    1121
```

<210> SEQ ID NO 11
<211> LENGTH: 288
<212> TYPE: PRT
<213> ORGANISM: homo sapiens

<400> SEQUENCE: 11

```
Met Ser Arg Leu Arg Ala Leu Leu Gly Leu Gly Leu Leu Val Ala Gly
1               5                   10                  15

Ser Arg Val Pro Arg Ile Lys Ser Gln Thr Ile Ala Cys Arg Ser Gly
                20                  25                  30

Pro Thr Trp Trp Gly Pro Gln Arg Leu Asn Ser Gly Gly Arg Trp Asp
            35                  40                  45

Ser Glu Val Met Ala Ser Thr Val Val Lys Tyr Leu Ser Gln Glu Glu
        50                  55                  60

Ala Gln Ala Val Asp Gln Glu Leu Phe Asn Glu Tyr Gln Phe Ser Val
65                  70                  75                  80

Asp Gln Leu Met Glu Leu Ala Gly Leu Ser Cys Ala Thr Ala Ile Ala
                85                  90                  95

Lys Ala Tyr Pro Pro Thr Ser Met Ser Arg Ser Pro Pro Thr Val Leu
            100                 105                 110

Val Ile Cys Gly Pro Gly Asn Asn Gly Gly Asp Gly Leu Val Cys Ala
        115                 120                 125

Arg His Leu Lys Leu Phe Gly Tyr Glu Pro Thr Ile Tyr Tyr Pro Lys
130                 135                 140

Arg Pro Asn Lys Pro Leu Phe Thr Ala Leu Val Thr Gln Cys Gln Lys
145                 150                 155                 160

Met Asp Ile Pro Phe Leu Gly Glu Met Pro Ala Glu Pro Met Thr Ile
                165                 170                 175

Asp Glu Leu Tyr Glu Leu Val Val Asp Ala Ile Phe Gly Phe Ser Phe
            180                 185                 190

Lys Gly Asp Val Arg Glu Pro Phe His Ser Ile Leu Ser Val Leu Lys
        195                 200                 205

Gly Leu Thr Val Pro Ile Ala Ser Ile Asp Ile Pro Ser Gly Trp Asp
210                 215                 220

Val Glu Lys Gly Asn Ala Gly Gly Ile Gln Pro Asp Leu Leu Ile Ser
225                 230                 235                 240

Leu Thr Ala Pro Lys Lys Ser Ala Thr Gln Phe Thr Gly Arg Tyr His
                245                 250                 255

Tyr Leu Gly Gly Arg Phe Val Pro Ala Leu Glu Lys Lys Tyr Gln
            260                 265                 270

Leu Asn Leu Pro Pro Tyr Pro Asp Thr Glu Cys Val Tyr Arg Leu Gln
        275                 280                 285
```